United States Patent
Schnepp et al.

(10) Patent No.: US 11,684,680 B2
(45) Date of Patent: *Jun. 27, 2023

(54) SYNTHETIC DNA VECTORS AND METHODS OF USE

(71) Applicant: Intergalactic Therapeutics, Inc., Cambridge, MA (US)

(72) Inventors: Bruce C. Schnepp, Havertown, PA (US); Philip R. Johnson, Bryn Mawr, PA (US)

(73) Assignee: INTERGALACTIC THERAPEUTICS, INC., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/057,032

(22) Filed: Nov. 18, 2022

(65) Prior Publication Data
US 2023/0089543 A1 Mar. 23, 2023

Related U.S. Application Data

(63) Continuation of application No. 17/675,899, filed on Feb. 18, 2022, which is a continuation of application No. 17/365,808, filed on Jul. 1, 2021, now Pat. No. 11,324,839, which is a continuation of application No. PCT/US2020/051507, filed on Sep. 18, 2020.

(60) Provisional application No. 62/902,084, filed on Sep. 18, 2019.

(51) Int. Cl.
*A61K 48/00* (2006.01)
*C12N 15/64* (2006.01)
*C12N 15/86* (2006.01)

(52) U.S. Cl.
CPC ...... *A61K 48/0066* (2013.01); *A61K 48/0058* (2013.01); *C12N 15/64* (2013.01); *C12N 15/86* (2013.01); *C12N 2320/32* (2013.01); *C12N 2750/14143* (2013.01); *C12N 2830/50* (2013.01)

(58) Field of Classification Search
None
See application file for complete search history.

(56) References Cited

U.S. PATENT DOCUMENTS

| | | | |
|---|---|---|---|
| 5,994,104 A | 11/1999 | Anderson et al. | |
| 6,027,722 A | 2/2000 | Hodgson | |
| 6,143,530 A | 11/2000 | Crouzet et al. | |
| 7,030,098 B2 | 4/2006 | Steinman et al. | |
| 7,595,303 B1 | 9/2009 | Mohapatra et al. | |
| 7,622,252 B2 | 11/2009 | Zechiedrich et al. | |
| 7,629,322 B2 | 12/2009 | Kleinschmidt et al. | |
| 8,802,643 B1 | 8/2014 | Heller et al. | |
| 8,945,885 B2 | 2/2015 | Chen et al. | |
| 9,045,759 B2 | 6/2015 | Williams | |
| 9,233,174 B2 | 1/2016 | Chen et al. | |
| 9,499,847 B2 | 11/2016 | Porter et al. | |
| 9,506,082 B2 | 11/2016 | Williams | |
| 9,701,981 B2 | 7/2017 | Lu et al. | |
| 10,280,425 B2 | 5/2019 | Chen et al. | |
| 11,066,679 B2 | 7/2021 | Kotin et al. | |
| 11,324,839 B2* | 5/2022 | Schnepp | C12N 15/86 |
| 2003/0032092 A1 | 2/2003 | Blanche et al. | |
| 2003/0082559 A1 | 5/2003 | Beach et al. | |
| 2004/0028653 A1 | 2/2004 | Seed et al. | |
| 2004/0219677 A1 | 11/2004 | Drocourt et al. | |
| 2005/0069991 A1 | 3/2005 | Hyman | |
| 2007/0196838 A1 | 8/2007 | Chesnut et al. | |
| 2013/0203121 A1 | 8/2013 | Rehberger et al. | |
| 2014/0107186 A1 | 4/2014 | Garcia et al. | |
| 2014/0350087 A9 | 11/2014 | Frost et al. | |
| 2015/0217000 A1 | 8/2015 | Chen et al. | |
| 2018/0296699 A1 | 10/2018 | Xie | |
| 2018/0305701 A1 | 10/2018 | Zechiedrich et al. | |
| 2019/0169637 A1 | 6/2019 | Hudecek et al. | |
| 2020/0048716 A1 | 2/2020 | Zechiedrich et al. | |
| 2020/0115727 A1 | 4/2020 | Su'Etsugu et al. | |
| 2020/0208188 A1 | 7/2020 | Liu et al. | |

(Continued)

FOREIGN PATENT DOCUMENTS

| | | |
|---|---|---|
| CA | 3005474 A1 | 5/2017 |
| JP | H08504102 A | 5/1996 |

(Continued)

OTHER PUBLICATIONS

Aranyi, et al. (2013) "Transcriptional regulation of the ABCC6 gene and the background of impaired function of missense disease-causing mutations", frontiers in Genetics, 4, article 27, 7 pages long. (Year: 2013).*
Oct. 26, 2022 Notice of Allowance U.S. Appl. No. 17/675,899.
Nov. 23, 2022 Corrected Notice of Allowance U.S. Appl. No. 17/675,899.
Feb. 16, 2022 Notice of Allowance U.S. Appl. No. 17/365,808.
Mar. 24, 2022 Corrected Notice of Allowability U.S. Appl. No. 17/365,808.
Apr. 18, 2022 Final Office Action U.S. Appl. No. 17/365,805.
Jun. 8, 2022 Non-Final Office Action U.S. Appl. No. 17/675,899.
Aug. 17, 2022 Notice of Allowance U.S. Appl. No. 17/675,899.
Sep. 8, 2022 Advisory Action U.S. Appl. No. 17/365,805.

(Continued)

*Primary Examiner* — Robert M Kelly
(74) *Attorney, Agent, or Firm* — Wilson Sonsini Goodrich & Rosati

(57) ABSTRACT

Provided herein are isolated DNA vectors comprising a heterologous gene, wherein the DNA vector is devoid of bacterial plasmid DNA and/or bacterial signatures, which can abrogate persistence in vivo. The invention also features pharmaceutical compositions (non-immunogenic pharmaceutical compositions) including the DNA vectors of the invention, which can be used for induction of long-term, episomal expression of a heterologous gene in a subject. The invention involves methods of treating a subject by administering the DNA vectors of the invention, including methods of treating disorders associated with a defect in a target gene.

17 Claims, 37 Drawing Sheets
Specification includes a Sequence Listing.

(56) References Cited

U.S. PATENT DOCUMENTS

| | | |
|---|---|---|
| 2020/0283794 A1 | 9/2020 | Kotin et al. |
| 2021/0002667 A1 | 7/2021 | Schnepp et al. |
| 2021/0322576 A1 | 10/2021 | Schnepp et al. |
| 2021/0322579 A1 | 10/2021 | Schnepp et al. |
| 2021/0330817 A1 | 10/2021 | Schnepp et al. |
| 2022/0168451 A1 | 6/2022 | Schneep et al. |

FOREIGN PATENT DOCUMENTS

| | | |
|---|---|---|
| JP | 2011516049 A | 5/2011 |
| JP | 2016518142 A | 6/2016 |
| WO | WO-9413788 A1 | 6/1994 |
| WO | WO-0073318 A1 | 12/2000 |
| WO | WO-2004099420 A1 | 11/2004 |
| WO | WO-2006023546 A2 | 3/2006 |
| WO | WO-2004020605 A3 | 10/2006 |
| WO | WO-2006063355 A3 | 10/2006 |
| WO | WO-2007018744 A2 | 2/2007 |
| WO | WO-2007089873 B1 | 11/2008 |
| WO | WO-2008153733 A3 | 5/2009 |
| WO | WO-2009121536 A1 | 10/2009 |
| WO | WO-2009025690 A3 | 11/2009 |
| WO | WO-2010026099 A1 | 3/2010 |
| WO | WO-2010086626 A1 | 8/2010 |
| WO | WO-2011047318 A2 | 4/2011 |
| WO | WO-2012045722 A1 | 4/2012 |
| WO | WO-2013090296 A1 | 6/2013 |
| WO | WO-2013181440 A1 | 12/2013 |
| WO | WO-2014077863 A1 | 5/2014 |
| WO | WO-2014077866 A1 | 5/2014 |
| WO | WO-2014093894 A3 | 7/2014 |
| WO | WO-2014170238 A1 | 10/2014 |
| WO | WO-2014182700 A1 | 11/2014 |
| WO | WO-2013119371 A3 | 6/2015 |
| WO | WO-2016094639 A1 | 6/2016 |
| WO | WO-2016126987 A1 | 8/2016 |
| WO | WO-2016154473 A1 | 9/2016 |
| WO | WO-2016183422 A1 | 11/2016 |
| WO | WO-2017087900 A1 | 5/2017 |
| WO | WO-2017106795 A1 | 6/2017 |
| WO | WO-2017137461 A1 | 8/2017 |
| WO | WO-2017152149 A1 | 9/2017 |
| WO | WO-2017191007 A1 | 11/2017 |
| WO | WO-2018111914 A1 | 6/2018 |
| WO | WO-2018172961 A1 | 9/2018 |
| WO | WO-2018187552 A1 | 10/2018 |
| WO | WO-2018229226 A1 | 12/2018 |
| WO | WO-2018229696 A1 | 12/2018 |
| WO | WO-2019051255 A1 | 3/2019 |
| WO | WO-2019057774 A1 | 3/2019 |
| WO | WO-2019060253 A1 | 3/2019 |
| WO | WO-2019178500 A1 | 9/2019 |
| WO | WO-2019183248 A1 | 9/2019 |
| WO | WO-2019226650 A1 | 11/2019 |
| WO | WO-2020077159 A1 | 4/2020 |
| WO | WO-2020081768 A1 | 4/2020 |
| WO | WO-2020088365 A1 | 5/2020 |
| WO | WO-2020101828 A2 | 5/2020 |
| WO | WO-2020112987 A1 | 6/2020 |
| WO | WO-2020150293 A1 | 7/2020 |
| WO | WO-2020174079 A1 | 9/2020 |
| WO | WO-2020214796 A1 | 10/2020 |
| WO | WO-2020214797 A1 | 10/2020 |
| WO | WO-2020214809 A2 | 10/2020 |
| WO | WO-2021042944 A1 | 3/2021 |
| WO | WO-2021042947 A1 | 3/2021 |
| WO | WO-2021055760 A1 | 3/2021 |

OTHER PUBLICATIONS

Alhaji, et al., "Silencing of transgene expression in mammalian cells by DNA methylation and histone modifications in gene therapy perspective." (2018) Biotechnology and Genetic Engineering Reviews, DOI: 10.1080/02648725.2018.1551594.

Alves, et al., "Minicircle Biopharmaceuticals—An overview of purification strategies." (2021) Front. Chem. Eng. 2.612594. DOI: 10.3389/fceng.2020.612594.

Argyros, et al., "Development of S/MAR minicircles for enhanced and persistent transgene expression in the mouse liver." (2011) J. Mol. Med. 89(5):515-529.

Catanese, et al., "Supercoiled Minivector DNA resists shear forces associated with gene therapy delivery" (2012) Gene Therapy, vol. 19, pp. 94-100.

Charters, Lynda "Ocular gene therapy offers hope for inherited retinal diseases", Ophthalmology Times, 45(18):42 (2020).

Schmeer, et al., "Pharmaceutical Grade Large-Scale Plasmid DNA Manufacturing Process." (2014) Monica Rinaldi et al. (eds.), DNA Vaccines: Methods and Protocols, Methods in Molecular Biology, vol. 1143, DOI 10.1007/978-1-4939-0410-5_14.

Schneep, et al., "Recombinant Adeno-Associated Virus Vector Genomes Take the Form of Long-Lived, Transcriptionally competent Episomes in Human Muscle" )2016) Human Gene Therapy, 27(1):32-42.

Dean, et al., "Rapid Amplification of Plasmid and Phage DNA Using Phi29 DNA Polymerase and Multiply-Primed Rolling Circle Amplification." (2001) Genome Research. 11: 1095-1099.

Esteban, et. al., "Fidelity of Phi29 DNA Polymerase." (1993) The Journal of Biological Chemistry vol. 268, No. 4, pp. 2719-2726.

Hacobian, et al., "Pushing the right buttons: Improving efficacy of therapeutic DNA vectors." (2018). Tissue Engineering, DOI: 10.1089/ten.TEB.2017.0353.

International Preliminary Report on Patentability for PCT Application No. PCT/US2019/022511 dated Sep. 15, 2020.

International Preliminary Report on Patentability for PCT Application No. PCT/US2020/051507 dated Mar. 15, 2022.

International Search Report and Written Opinion for corresponding PCT Application No. PCT/US2019/0225121 dated Jun. 10, 2019.

International Search Report and Written Opinion for PCT Application No. PCT/US2019/022511 dated Jun. 10, 2019.

International Search Report and Written Opinion for PCT Application No. PCT/US2020/051507 dated Feb. 22, 2021.

Johne, et al., "Rolling-circle amplification of viral DNA genomes using phi29 polymerase" (2009) Trends in Microbiology. vol. 17, No. 5, pp. 205-211.

Laengle-Rouault, et al., "GATC sequence and mismatch repair in *Escherichia coli*" (1986) The EMBO Journal, vol. 5, No. 8, pp. 2009-2013.

Lu, et al., "A mini-intronic plasmid (MIP): A novel robust transgene expression vector in vivo and in vitro." (2013) Molecular Therapy, vol. 21, No. 5, pp. 954-963.

Lu, et al., "Sequence-Modified Antibiotic Resistance Genes Provide Sustained Plasmid-Mediated Transgene Expression in Mammals" (2017) Molecular Therapy, vol. 25, No. 5, pp. 1187-1198.

Lu, et al., "The extragenic spacer length between the 5' and 3' ends of the transgene expression cassette affects transgene silencing from plasmid-based vectors" (2012) Molecular Therapy, vol. 20, No. 11, pp. 2111-2119.

Mayrhofer, "Coordinating the in vivo processes for minicircle production—a novel approach to large scale manufacturing" (Apr. 15, 2018) bioRxiv.

Monjezi, et al., "Enhanced CAR T-cell engineering using non-viral Sleeping Beauty transposition from minicircle vectors." (2016) Leukemia, 1-9.

Ren, et. al., "Cloning of linear DNAs in vivo by overexpressed T4 DNA ligase: construction of a T4 phage hoc gene display vector." (1997), Gene 195, pp. 303-311.

Schneep, et al. "Recombinant Adeno-Associated Virus Vector Genomes Take the form of Long-Lived, Transcriptionally Competent Episomes in Human Muscle", Human Gene Therapy, 27(1): 32-42 (2016).

Toscano, et al., "Physiological and tissue-specific vectors for treatment of inherited diseases" (2011) Gene Therapy, 18, 117-127.

Toualbi, et al., "The Landscape of Non-Viral Gene Augmentation Strategies for Inherited Retinal Diseases." (2021) Int. J. Mol. Sci. 22, 2318; doi.org/10.3390/ijms22052318.

Trapani et al. "Vector platforms for gene therapy of inherited retinopathies" (2014) Progress In Retinal Eye Research 43:108-128.

(56) References Cited

OTHER PUBLICATIONS

U.S. Office Action for U.S. Appl. No. 17/365,805 dated Nov. 23, 2021.
U.S. Office Action for U.S. Appl. No. 17/365,808 dated Nov. 1, 2021.
U.S. Office Action for U.S. Appl. No. 17/365,846 dated Jan. 5, 2022.
U.S. Office Action for U.S. Appl. No. 17/365,846 dated Nov. 4, 2022.
Wang, et al., "In Vivo Electroporation of Minicircle DNA as a Novel Method of Vaccine Delivery To Enhance HIV-1-Specific Immune Responses," (2014) Journal of Virology, vol. 88, No. 4, pp. 1924-1934.
Wong, et al., "Non-viral S/MAR vectors replicate episomally in vivo when provided with a selective advantage." (2011) Gene Therapy, 18 pp. 82-87.
Xiao, et al., "A Novel 165-Base-Pair Terminal Repeat Sequence Is the Side Cis Requirement For The Adeno-Associated Virus Life Cycle" Journal of Virology (1997) vol. 71, pp. 941-948.
Zhang, W. et al., "Gene Therapy Using a miniCEP290 Fragment Delays Photoreceptor Degeneration in a Mouse Model of Leber Congenital Amaurosis", Human Gene Therapy, 2018, 29(1): 42-50.
U.S. Notice of Allowance for U.S. Appl. No. 17/365,846 dated Feb. 22, 2023.

\* cited by examiner

SEQ ID NO: 33

Start (0)  Eael  MscI                                          End (40)   SEQ ID NO: 43

5' cagagaggagtgtggccaactccatcactagggtagcgcg 3'
   ||||||||||||||||||||||||||||||||||||||||      40
3' gtctctcctcaccggttgaggtagtgatcccatcgcgc 5' partial A                                      D

FIG. 21

Start (0)  EaeI  MscI                                          End (41) SEQ ID NO: 44

5' cagagaggagtggccaactccatcactaggggtaatcgcg 3'  41
3' gtctctcctcaccggttgaggtagtgatcccattagcgc 5' partial A                                                      D

FIG. 6A

Start (0)

AGGAACCCTAGTGATGGAGTTGGCCAGTTCCTCAGTGAGCCGAGAGAGGAGTCCGAGGGTGCAAAGCCAGGCCGGGCTCGGGA

TCCTTGGGATCACTACCTCAACCGGTGAGCCGGTCGCTCTCTGGGGCTCGCCTGCTCAGTGAGCCGAGAGAGGAGTCCGAGGGGGCTCGGGACCCGCCGCGGGCTGCCGGGCTCGGGAGCCCT

AhdI

CCTTTGGTCGCCCGGCCCTCAGTGAGCGGCCAACTCCCATCAGTAGGGTTCCT       End (165)  3'  SEQ ID NO: 9
                                                                             165
GGAAACCAGCGGGCCGGGAGTCACTCGCCGGTTGAGGTAGTCATCCCAAGGA                     5'

SEQ ID NO: 12

FIG. 6E

Start (0)

AGGAGCCCTAGTGATGGAGTTGGCCACTCCCTCTGTGCCTCCTCGTCACTGAGGGAGCGCTCAGGAGA
TCCTTGGGATCACTACCTCAACCGTGAGGAGACGGACGGBCAGTCACTCGGGAGTCACTCGGTCGGCTCCGGAGAGA...

End (122)

GGGAGTGGCCAACTGCATCACTAGGGTTCCT  3' SEQ ID NO: 13
CCCTCACCGGTTGAGGTAGTGATCCCCAAGGA  122
                                  5'

FIG. 6F

Start (0) ──────────────── End (40)

5'-AGGAACCCCTAGTGATGGAGCTCCATCACTAGGGGTTCCT-3' SEQ ID NO: 14
3'-TCCTTGGGGATCACTACCTCGAGGTAGTGATCCCCAAGGA-5' 40

FIG. 6G

*Start (0)*

...aggaacctaatcatgagttgaccaatccctctactcgctcgatcactgagcccagacccaggagagagcgagtg

*End (115)*  3'  SEQ ID NO: 15 gccaactccatcctagggctcct
cggttgagtagtgatccccaagga  5'  115

Deleted A

FIG. 6H

*Start* (0)

ggnaaccctagtagtggctgactcctccctctgccgtcactgcgtcagtcctgccgagggccgagcggcccgaggcccggcgcccggaggccggccgagtccgctgagcgaccgatgcgac tcctgggaatcactggccaaccacctgctgtgaggagagagacgcgcgcggagtgactcggagagcgggtcaggtggcggagctcacggaaggcggcgtggtacgctcgctgcctgcgtcgca

*End* (129)

cgagagaggagtgctggccaacttcatcactaggggtcct 3' cgtctctcctcacgaccgtcgagtagtcatgtgatcccaagga 5'

SEQ ID NO: 16

Start (0)      End (73)

AGGAACCCCTAGTGATGAGTTGGCCAACTCCCTCGGCAGAGAGGAGTGGCCAACTCCATCACTAGGGTTCCT 3' SEQ ID NO: 17
TCCTTGGGGATCACTACGTCAACCGGTCAAGGAGCGTCTCCTCACCGGTTGAGGTAGTGATCCCAAGGA 5'   73

FIG. 6J

Start (0)

aggaaccctagtgatggagtgccactccctctcttcggctcgctgctcatgaggccgcgaggccgcagggaggagggaggtggccaactc tccttgggatcactacctcaaccgatgaggacggagacgcagaccgagactactccgagtcgccgtctcccttcccgtccaccggttgag End (107)    SEQ ID NO: 18

3'                107 catcactaggggttcct gtagtgatccccaagga    5'

US 11,684,680 B2

SYNTHETIC DNA VECTORS AND METHODS OF USE

CROSS REFERENCE

This application is a continuation application of U.S. application Ser. No. 17/675,899, filed Feb. 18, 2022 which is a continuation of U.S. application Ser. No. 17/365,808, filed Jul. 1, 2021, now U.S. Pat. No. 11,324,839, issued May 10, 2022 which is continuation of International Application No. PCT/US2020/051507, filed Sep. 18, 2020 which claims benefit to U.S. Provisional Application No. 62/902,084, filed Sep. 18, 2019, each of which is entirely incorporated herein by reference for all purposes.

SEQUENCE LISTING

The instant application contains a Sequence Listing which has been submitted electronically in XML format and is hereby incorporated by reference in its entirety. Said XML copy, created on Nov. 18, 2022, is named 61211-702.305 Sequence Listing.xml and is 57,946 bytes in size.

FIELD OF THE INVENTION

In general, the invention features synthetic DNA vectors.

BACKGROUND

Gene therapy involves transduction of heterologous genes into target cells to correct a genetic defect underlying a disorder in a subject. A variety of transduction approaches have been developed for use in gene therapy over the past several decades. For example, traditional bacterial plasmid DNA vectors represent a versatile tool in gene delivery but can present limitations owing to their bacterial origin. Plasmid DNA vectors include bacterial genes, such as antibiotic resistance genes and origins of replication. Additionally, plasmid DNA vectors include bacterial signatures, such as CpG motifs. In addition, the use of bacterial expression systems for producing plasmid DNA vectors involves the risk of introducing contaminating impurities from the bacterial host, such as endotoxins or bacterial genomic DNA and RNA, which can lead to loss of gene expression in vivo, e.g., by transcriptional silencing.

Recombinant adeno-associated viral (rAAV) vectors have an established record of high-efficiency gene transfer in a variety of model systems and are now being tested as therapeutic modalities in a wide range of human diseases. Genomes of rAAV vectors can persist in vivo (e.g., in post-mitotic cells) as circular episomes. After infection, single-stranded rAAV DNA is converted to double stranded circular DNA in the cell nucleus and persists in an episomal form for the life of the cell. Thus, a substantial benefit of AAV vector systems is the ability to persist long term in a target cell. On the other hand, AAV vectors can involve additional drawbacks, such as a limited packaging capacity of about 4.5 Kb, immunogenicity of viral proteins, and manufacturing difficulties.

Thus, there is a need in the field for versatile and efficient methods to enhance long-term persistence of gene expression, such as that provided by rAAV, while enabling large payloads and reducing the risk of adverse effects (e.g., inflammation).

SUMMARY

The present invention provides non-viral, circular DNA vectors that replicate the in vivo persistence of rAAV vectors. The present DNA vectors are non-immunogenic and are not limited to the AAV packaging capacity (about 4.5 Kb). The invention also features methods of producing the circular DNA vector (e.g., using cell-free methods providing improved manufacturing efficiencies over conventional bacterial-based syntheses), pharmaceutical compositions including the circular DNA vector, and methods of using the vectors described herein, e.g., for inducing persistent episomal expression of a heterologous gene and for treating a disease associated with a defective gene.

In one aspect, the invention provides an isolated circular DNA vector including one or more heterologous genes encoding a therapeutic replacement protein, wherein the DNA vector lacks: (a) an origin of replication (e.g., a bacterial original of replication) and/or a drug resistance gene; and (b) a recombination site. For example, in some embodiments, the DNA vector lacks an origin of replication, a drug resistance gene, and a recombination site. The therapeutic replacement protein may be, e.g., an enzyme, a growth factor, a hormone, an interleukin, an interferon, a cytokine, an anti-apoptosis factor, an anti-diabetic factor, a coagulation factor, an anti-tumor factor, a liver-secreted protein, or a neuroprotective factor. In some embodiments, the enzyme is an epigenetic regulator. In some embodiments, the epigenetic regulator is a histone methyltransferase, a histone demethylase, a histone acetylase, a DNA methyltransferase, or a DNA demethylase.

In another aspect, the invention provides an isolated circular DNA vector including one or more heterologous genes encoding an antigen-binding protein. In some embodiments, the DNA vector lacks: (a) an origin of replication (e.g., a bacterial original of replication) and/or a drug resistance gene; and (b) a recombination site. For example, in some embodiments, the DNA vector lacks an origin of replication, a drug resistance gene, and a recombination site. The antigen-binding protein may be an antibody or an antigen-binding fragment thereof. The antigen-binding protein may bind a cytokine, a growth factor, or a cell-surface protein (e.g., a tumor-associated antigen). In some embodiments, the antigen-binding protein binds TNF, LT, IFN-α, IFN-γ, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-21, EMAP-II, GM-CSF, EGF, HER2, HER3, FGF, PDGF, BDNF, CNTF, CSF, G-CSF, NGF, PEDF, TGF, VEGF, gonadotropin, insulin-like growth factor, CD2, CD3, CD4, CD8, CD19, CD20, CD25, CD28, CD30, CD40, CD45, CD69, CD80, CD86, CD90, PD-1, PD-L1, amyloid beta, alkaline phosphatase, amyloid protein A, CCR4, folate receptor, mucin 5AC, PCSK-9, phosphatidyl-serine, or sclerostin. The antigen-binding protein may be a monoclonal antibody, a polyclonal antibody, a multispecific antibody (e.g., a bispecific antibody), and/or an antigen-binding fragment (e.g., Fab, scFv, scFab, etc.).

In another aspect, the invention provides an isolated circular DNA vector including one or more heterologous genes encoding an enzyme, a growth factor, a hormone, an interleukin, an interferon, a cytokine, an anti-apoptosis factor, an anti-diabetic factor, a coagulation factor, an anti-tumor factor, a liver-secreted protein, or a neuroprotective factor, wherein the DNA vector lacks: (a) an origin of replication (e.g., a bacterial original of replication) and/or a drug resistance gene; and (b) a recombination site. The growth factor may be brain-derived neurotrophic factor (BDNF), ciliary neurotrophic factor (CNTF), colony stimulating factor (CSF), epidermal growth factor (EGF), fibroblast growth factor (FGF), granulocyte-colony stimulating factor (G-SCF), macrophage-colony stimulating factor (M-CSF), granulocyte-macrophage colony stimulating factor (GM-CSF), nerve growth factor (NGF), platelet-derived growth factor (PDGF), pigment epithelium-derived factor (PEDF), transforming growth factor (TGF; e.g., TGF-β), vascular endothelial growth factor (VEGF), gonadotropin, or an insulin-like growth factor. The interleukin (IL) may be IL-1 (e.g., IL-1β), IL-2, IL-3, IL-4, IL-5, IL-6, IL-7, IL-8, IL-9, IL-10, IL-11, IL-12, IL-13, IL-14, IL-15, IL-16, IL-17, IL-18, or IL-21. The interferon (IFN) may be IFN-α or IFN-γ. The coagulation factor may be factor V, factor VII, factor VIII, factor IX, factor X, factor XI, factor XII, factor XIII, or von Willebrand factor. The neuroprotective factor may be selected from the group consisting of a neurotrophin (NT, e.g., NGF, BDNF, NT-3, NT-4, or CNTF), Kifap3, Bcl-xl, Crmp1, Chk.beta., CALM2, Caly, NPG11, NPT1, Eef1a1, Dhps, Cd151, Morf412, CTGF, LDH-A, Atl1, NPT2, Ehd3, Cox5b, Tuba1a, gamma-actin, Rpsa, NPG3, NPG4, NPG5, NPG6, NPG7, NPG8, NPG9, and NPG10.

In another aspect, the invention provides an isolated circular DNA vector including one or more heterologous genes associated with a disorder selected from the group consisting of an ocular disorder, a liver disorder, a neurological disorder, an immune disorder, a cancer, a cardiovascular disorder, a blood coagulation disorder, a lysosomal storage disorder, or type 2 diabetes, wherein the DNA vector lacks: (a) an origin of replication (e.g., a bacterial original of replication) and/or a drug resistance gene; and (b) a recombination site. For example, in some embodiments, the DNA vector lacks an origin of replication, a drug resistance gene, and a recombination site.

The disorder may be an ocular disorder that is a retinal dystrophy (e.g., a Mendelian-heritable retinal dystrophy). The retinal dystrophy may be selected from the group consisting of leber's congenital amaurosis (LCA), Stargardt Disease, pseudoxanthoma elasticum, rod cone dystrophy, exudative vitreoretinopathy, Joubert Syndrome, congenital stationary night blindness, type 1C (CSNB-1C), age-related macular degeneration, retinitis pigmentosa, stickler syndrome, microcephaly and chorioretinopathy, retinitis pigmentosa, CSNB 2, Usher syndrome, and Wagner syndrome. In some embodiments, the disorder is a cancer and the heterologous gene is CD40, CD40L, CD46, XCL1, MDA-7, IL-12, IL-24, or OPCML (opioid binding protein/cell adhesion molecule). The disorder may, in some instances, be a cancer and the heterologous gene is a tumor suppressor gene. The tumor suppressor gene may be a gene encoding an intracellular protein. The tumor suppressor gene may be a gene encoding a receptor or signal transducer for a secreted hormone or developmental signal that inhibits cell proliferation. The tumor suppressor gene also may be a gene that encodes a checkpoint control protein. The tumor suppressor gene may be a gene that encodes a pro-apoptotic protein. The tumor suppressor gene may be a gene that encodes a DNA repair protein.

In some embodiments, the disorder is a coagulation disorder, such as hemophilia (e.g., hemophilia A or hemophilia B), von Willebrand's disease, factor XI deficiency, a fibrinogen disorder, or a vitamin K deficiency. The coagulation disorder may be characterized by a mutation in a gene encoding for fibrinogen, prothrombin, factor V, factor VII, factor VIII, factor X, factor XI, factor XIII, or an enzyme involved in posttranslational modifications thereof, or an enzyme involved in vitamin K metabolism. In some embodiments, the coagulation disorder is characterized by a mutation in a one or more of the following genes: fibrinogen alpha (FGA), fibrinogen beta (FGB), fibrinogen gamma (FGG), factor (F) F2, F5, F7, F10, F11, F13A, F13B, lectin mannose binding 1 (LMAN1), multiple coagulation factor deficiency 2 (MCFD2), gamma glutamyl carboxylase (GGCX), or vitamin K epoxide reductase complex subunit 1 (VKORC1).

The disorder may be a neurological disorder, e.g., a neurodegenerative disease. The neurodegenerative disease may be selected from the group consisting of Alzheimer's disease, Parkinson's disease, or multiple sclerosis. The neurodegenerative disease may be an autoimmune disease of the central nervous system (CNS), such as multiple sclerosis, encephalomyelitis, a paraneoplastic syndrome, autoimmune inner ear disease, or opsoclonus myoclonus syndrome. The neurological disorder may be a cerebral infarction, spinal cord injury, central nervous system disorder, a neuropsychiatric disorder, or a channelopathy (e.g., epilepsy or migraine). The neurological disorder may be an anxiety disorder, a mood disorder, a childhood disorder, a cognitive disorder, schizophrenia, a substance related disorders, or an eating disorders. In some embodiments, the neurological disorder is a symptom of a cerebral infarction, stroke, traumatic brain injury, or spinal cord injury.

In some embodiments, the disorder is a lysosomal storage disorder, such as Tay-Sachs disease, Gaucher disease, Fabry disease, Pompe disease, Niemann-Pick disease, or mucopolysaccharidosis (MPS).

In some embodiments, the disorder is a cardiovascular disorder, such as a degenerative heart disease, a coronary artery disease, an ischemia, angina pectoris, an acute coronary syndrome, a peripheral vascular disease, a peripheral arterial disease, a cerebrovascular disease, or atherosclerosis. The cardiovascular disorder may be a degenerative heart disease selected from the group consisting of an ischemic cardiomyopathy, a conduction disease, and a congenital defect.

The disorder may be an immune disorder, e.g., an autoimmune disorder. The autoimmune disorder may be type 1 diabetes, multiple sclerosis, rheumatoid arthritis, lupus, encephalomyelitis, a paraneoplastic syndrome, autoimmune inner ear disease, or opsoclonus myoclonus syndrome, autoimmune hepatitis, uveitis, autoimmune retinopathy, neuromyelitis optica, psoriatic arthritis, psoriasis, myasthenia gravis, chronic Lyme disease, celiac disease, chronic inflammatory demyelinating polyneuropathy, peripheral neuropathy, fibromyalgia, Hashimoto's thyroiditis, ulcerative colitis, or Kawasaki disease.

The disorder may be a liver disease, e.g., a liver disease selected from the group consisting of hepatitis, Alagille syndrome, biliary atresia, liver cancer, cirrhosis, a cystic disease, Caroli's syndrome, congenital hepatic fibrosis, fatty liver, galactosemia, primary sclerosing cholangitis, tyrosinemia, glycogen storage disease, Wilson's disease, and an endocrine deficiency. The liver disease may be a liver cancer selected from the group consisting of a hepatocellular hyperplasia, a hepatocellular adenomas, a focal nodular hyperplasia, or a hepatocellular carcinoma.

In some embodiments, the disorder is a cancer, such as a blood cancer (e.g., acute lymphoblastic leukemia, acute myeloblastic leukemia, chromic myelogenous leukemia, Hodgkin's disease, multiple myeloma, and non-Hodgkin's lymphoma) or a solid tissue cancer (e.g., liver cancer, kidney cancer, a breast cancer, a prostate cancer, a gastric cancer, an esophageal cancer, a stomach cancer, an intestinal cancer, a colorectal cancer, a bladder cancer, a head and neck cancer, a skin cancer, or a brain cancer). In some embodiments, the heterologous gene encodes a transcription factor, such as TSHZ2, HOXA2, MEIS2, HOXA3, HAND2, HOXA5, TBX18, PEG3, GLI2, CLOCK, HNF4A, VHL/HIF, WT-1, GSK-3, SPINT2, SMAD2, SMAD3, or SMAD4.

In some embodiments, the disorder is a recessively inherited disorder. In some embodiments, the disorder is a Mendelian-inherited disorder.

In some embodiments of any of the above aspects, the heterologous gene is expressible in a target cell selected from the group consisting of a liver cell, a retinal cell, a stem cell, a neural cell, a muscle cell, or a blood cell. The target cell may be a post-mitotic cell. In some embodiments, the target cell may be a neural cell selected from the group consisting of a neuron, an astrocyte, an oligodendrocyte, and a Schwann cell.

In some embodiments of any of the above aspects, the therapeutic protein is secreted into blood (e.g., when endogenously expressed, the protein normally secreted into the blood).

In some embodiments of any of the above aspects, the DNA vector includes a terminal repeat sequence ((e.g., one or more inverted terminal repeat (ITR) sequences (e.g., two ITR sequences) or portion thereof (e.g., two A elements, B elements, C elements, or D elements), or long terminal repeat (LTR) sequences (e.g., two LTR sequences)). In some embodiments, the terminal repeat sequence is at least 10 base pairs (bp) in length (e.g., from 10 bp to 500 bp, from 12 bp to 400 bp, from 14 bp to 300 bp, from 16 bp to 250 bp, from 18 bp to 200 bp, from 20 bp to 180 bp, from 25 bp to 170 bp, from 30 bp to 160 bp, or from 50 bp to 150 bp, e.g., from 10 bp to 15 bp, from 15 bp to 20 bp, from 20 bp to 25 bp, from 25 bp to 30 bp, from 30 bp to 35 bp, from 35 bp to 40 bp, from 40 bp to 45 bp, from 45 bp to 50 bp, from 50 bp to 55 bp, from 55 bp to 60 bp, from 60 bp to 65 bp, from 65 bp to 70 bp, from 70 bp to 80 bp, from 80 bp to 90 bp, from 90 bp to 100 bp, from 100 bp to 150 bp, from 150 bp to 200 bp, from 200 bp to 300 bp, from 300 bp to 400 bp, or from 400 bp to 500 bp, e.g., 10 bp, 11 bp, 12 bp, 13 bp, 14 bp, 15 bp, 16 bp, 17 bp, 18 bp, 19 bp, 20 bp, 21 bp, 22 bp, 23 bp, 24 bp, 25 bp, 26 bp, 27 bp, 28 bp, 29 bp, 30 bp, 31 bp, 32 bp, 33 bp, 34 bp, 35 bp, 36 bp, 37 bp, 38 bp, 39 bp, 40 bp, 41 bp, 42 bp, 43 bp, 44 bp, 45 bp, 46 bp, 47 bp, 48 bp, 49 bp, 50 bp, 51 bp, 52 bp, 53 bp, 54 bp, 55 bp, 56 bp, 57 bp, 58 bp, 59 bp, 60 bp, 61 bp, 62 bp, 63 bp, 64 bp, 65 bp, 66 bp, 67 bp, 68 bp, 69 bp, 70 bp, 71 bp, 72 bp, 73 bp, 74 bp, 75 bp, 76 bp, 77 bp, 78 bp, 79 bp, 80 bp, 81 bp, 82 bp, 83 bp, 84 bp, 85 bp, 86 bp, 87 bp, 88 bp, 89 bp, 90 bp, 91 bp, 92 bp, 93 bp, 94 bp, 95 bp, 96 bp, 97 bp, 98 bp, 99 bp, 100 bp, 101 bp, 102 bp, 103 bp, 104 bp, 105 bp, 106 bp, 107 bp, 108 bp, 109 bp, 110 bp, 111 bp, 112 bp, 113 bp, 114 bp, 115 bp, 116 bp, 117 bp, 118 bp, 119 bp, 120 bp, 121 bp, 122 bp, 123 bp, 124 bp, 125 bp, 126 bp, 127 bp, 128 bp, 129 bp, 130 bp, 131 bp, 132 bp, 133 bp, 134 bp, 135 bp, 136 bp, 137 bp, 138 bp, 139 bp, 140 bp, 141 bp, 142 bp, 143 bp, 144 bp, 145 bp, 146 bp, 147 bp, 148 bp, 149 bp, 150 bp, or more). In some embodiments, the DNA vector includes a DD element.

In some embodiments of any of the above aspects, the DNA vector includes a promoter sequence upstream of the one or more heterologous genes.

In some embodiments of any of the above aspects, the DNA vector includes a polyadenylation site downstream of the one or more heterologous genes.

In some embodiments of any of the above aspects, the one or more heterologous genes includes a trans-splicing molecule or a portion thereof (e.g., a binding domain).

In another aspect, the invention provides an isolated circular DNA vector having one or more therapeutic nucleic acids. Such an isolated circular DNA vector lacks an origin of replication and/or a drug resistance gene; lacks a recombination site; and comprises a terminal repeat sequence (e.g., a DD element). In some embodiments, the therapeutic nucleic acid is an siRNA, an shRNA, an miRNA, or a CRISPRi molecule. In some embodiments, the terminal repeat sequence (e.g., DD element) is at least 10 bp in length.

In some embodiments of any of the above aspects, the vector includes a suicide gene. In some embodiments of any of the above aspects, the DNA vector lacks bacterial plasmid DNA. In some embodiments, the DNA vector includes one or more unmethylated GATC sequences, one or more unmethylated CCAGG sequences, and/or one or more CCTGG sequences. Additionally or alternatively, the DNA vector may (a) lacks an immunogenic bacterial signature; (b) lack an RNA polymerase arrest site; and/or (c) be substantially devoid of CpG islands.

In some embodiments of any of the above aspects, the heterologous gene is greater than 4.5 Kb in length (e.g., the one or more heterologous genes, together or each alone, are from 4.5 Kb to 25 Kb, from 4.6 Kb to 24 Kb, from 4.7 Kb to 23 Kb, from 4.8 Kb to 22 Kb, from 4.9 Kb to 21 Kb, from 5.0 Kb to 20 Kb, from 5.5 Kb to 18 Kb, from 6.0 Kb to 17 Kb, from 6.5 Kb to 16 Kb, from 7.0 Kb to 15 Kb, from 7.5 Kb to 14 Kb, from 8.0 Kb to 13 Kb, from 8.5 Kb to 12.5 Kb, from 9.0 Kb to 12.0 Kb, from 9.5 Kb to 11.5 Kb, or from 10.0 Kb to 11.0 Kb in length, e.g., from 4.5 Kb to 8 Kb, from 8 Kb to 10 Kb, from 10 Kb to 15 Kb, from 15 Kb to 20 Kb in length, or greater, e.g., from 4.5 Kb to 5.0 Kb, from 5.0 Kb to 5.5 Kb, from 5.5 Kb to 6.0 Kb, from 6.0 Kb to 6.5 Kb, from 6.5 Kb to 7.0 Kb, from 7.0 Kb to 7.5 Kb, from 7.5 Kb to 8.0 Kb, from 8.0 Kb to 8.5 Kb, from 8.5 Kb to 9.0 Kb, from 9.0 Kb to 9.5 Kb, from 9.5 Kb to 10 Kb, from 10 Kb to 10.5 Kb, from 10.5 Kb to 11 Kb, from 11 Kb to 11.5 Kb, from 11.5 Kb to 12 Kb, from 12 Kb to 12.5 Kb, from 12.5 Kb to 13 Kb, from 13 Kb to 13.5 Kb, from 13.5 Kb to 14 Kb, from 14 Kb to 14.5 Kb, from 14.5 Kb to 15 Kb, from 15 Kb to 15.5 Kb, from 15.5 Kb to 16 Kb, from 16 Kb to 16.5 Kb, from 16.5 Kb to 17 Kb, from 17 Kb to 17.5 Kb, from 17.5 Kb to 18 Kb, from 18 Kb to 18.5 Kb, from 18.5 Kb to 19 Kb, from 19 Kb to 19.5 Kb, from 19.5 Kb to 20 Kb, from 20 Kb to 21 Kb, from 21 Kb to 22 Kb, from 22 Kb to 23 Kb, from 23 Kb to 24 Kb, from 24 Kb to 25 Kb in length, or greater, e.g., about 4.5 Kb, about 5.0 Kb, about 5.5 Kb, about 6.0 Kb, about 6.5 Kb, about 7.0 Kb, about 7.5 Kb, about 8.0 Kb, about 8.5 Kb, about 9.0 Kb, about 9.5 Kb, about 10 Kb, about 11 Kb, about 12 Kb, about 13 Kb, about 14 Kb, about 15 Kb, about 16 Kb, about 17 Kb, about 18 Kb, about 19 Kb, about 20 Kb in length, or greater).

In some embodiments of any of the above aspects, the DNA vector is double stranded. Additionally or alternatively, the double stranded vector may be monomeric and/or supercoiled.

In some embodiments, the DNA vector is covalently closed.

In another aspect, the invention provides a composition (e.g., a pharmaceutical composition) comprising a plurality of the DNA vectors of any of the preceding aspects. In some embodiments, at least 50% of the plurality of the DNA vectors of the composition (e.g., pharmaceutical composition) includes one or more unmethylated GATC sequences, one or more unmethylated CCAGG sequences, and/or one or more CCTGG sequences.

In another aspect, the invention provides an isolated linear DNA molecule including a plurality of identical amplicons (e.g., a concatamer), wherein each of the plurality of identical amplicons includes a heterologous gene encoding a therapeutic replacement protein. The DNA molecule lacks: (a) an origin of replication (e.g., a bacterial original of replication) and/or a drug resistance gene; and (b) a recombination site. For example, in some embodiments, the isolated linear DNA molecule lacks an origin of replication, a drug resistance gene, and a recombination site. In some embodiments, the isolated linear DNA molecule includes restriction enzyme sites, e.g., wherein each restriction enzyme site is positioned between the heterologous gene and a terminal repeat sequence. The therapeutic replacement protein may be, e.g., an enzyme, a growth factor, a hormone, an interleukin, an interferon, a cytokine, an anti-apoptosis factor, an anti-diabetic factor, a coagulation factor, an anti-tumor factor, a liver-secreted protein, or a neuroprotective factor.

In another aspect, the invention provides an isolated linear DNA molecule including a plurality of identical amplicons, wherein each of the plurality of identical amplicons includes one or more heterologous genes encoding an antigen-binding protein, wherein the DNA vector lacks: (a) an origin of replication (e.g., a bacterial original of replication) and/or a drug resistance gene; and (b) a recombination site. For example, in some embodiments, the isolated linear DNA molecule lacks an origin of replication, a drug resistance gene, and a recombination site. In some embodiments, the isolated linear DNA molecule includes restriction enzyme sites, e.g., wherein each restriction enzyme site is positioned between the heterologous gene and a terminal repeat sequence.

In some embodiments, the antigen-binding protein is an antibody or an antigen-binding fragment thereof. The antigen-binding protein may bind a cytokine, a growth factor, or a cell-surface protein (e.g., a tumor-associated antigen). In some embodiments, the antigen-binding protein binds tumor necrosis factor (TNF), large T antigen (LT), IFN-α, IFN-γ, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-21, endothelial-monocyte-activating polypeptide II (EMAP-II), GM-CSF, EGF, human epidermal growth factor 2 (HER2), HER3, FGF, PDGF, BDNF, CNTF, CSF, G-CSF, NGF, PEDF, TGF, VEGF, gonadotropin, insulin-like growth factor, CD2, CD3, CD4, CD8, CD19, CD20, CD25, CD28, CD30, CD40, CD45, CD69, CD80, CD86, CD90, programmed death-1 (PD-1), programmed death-ligand 1 (PD-L1), amyloid beta, alkaline phosphatase, amyloid protein A, CC chemokine receptor 4 (CCR4), folate receptor, mucin 5AC, proprotein convertase subtilisin/kexin type 9 (PCSK-9), phosphatidyl-serine, or sclerostin. The antigen-binding protein may be a monoclonal antibody, a polyclonal antibody, a multispecific antibody (e.g., a bispecific antibody), and/or an antigen-binding fragment (e.g., Fab, scFv, scFab, etc.).

In another aspect, the invention provides an isolated linear DNA molecule including a plurality of identical amplicons, wherein each of the plurality of identical amplicons includes one or more heterologous genes encoding an enzyme, a growth factor, a hormone, an interleukin, an interferon, a cytokine, an anti-apoptosis factor, an anti-diabetic factor, a coagulation factor, an anti-tumor factor, a liver-secreted protein, or a neuroprotective factor, wherein the DNA molecule lacks: (a) an origin of replication (e.g., a bacterial original of replication) and/or a drug resistance gene; and (b) a recombination site. For example, in some embodiments, the isolated linear DNA molecule lacks an origin of replication, a drug resistance gene, and a recombination site. In some embodiments, the isolated linear DNA molecule includes restriction enzyme sites, e.g., wherein each restriction enzyme site is positioned between the heterologous gene and a terminal repeat sequence.

The growth factor may be BDNF, CNTF, CSF, EGF, FGF, G-SCF, M-CSF, GM-CSF, NGF, PDGF, PEDF, TGF, VEGF, gonadotropin, or an insulin-like growth factor. The interleukin may be is IL-1 (e.g., IL-1β), IL-2, IL-3, IL-4, IL-5, IL-6, IL-7, IL-8, IL-9, IL-10, IL-11, IL-12, IL-13, IL-14, IL-15, IL-16, IL-17, IL-18, or IL-21. The interferon may be IFN-α or IFN-γ. The coagulation factor may be factor V, factor VII, factor VIII, factor IX, factor X, factor XI, factor XII, factor XIII, or von Willebrand factor. The neuroprotective factor may be selected from the group consisting of a neurotrophin, Kifap3, Bcl-xl, Crmp1, Chk.beta., CALM2, Caly, NPG11, NPT1, Eef1a1, Dhps, Cd151, Morf412, CTGF, LDH-A, Atl1, NPT2, Ehd3, Cox5b, Tuba1a, gamma-actin, Rpsa, NPG3, NPG4, NPG5, NPG6, NPG7, NPG8, NPG9, and NPG10. The neurotrophin may be selected from the group consisting of NGF, BDNF, NT-3, NT-4, and CNTF.

In another aspect, the invention provides an isolated linear DNA molecule including a plurality of identical amplicons, wherein each of the plurality of identical amplicons includes one or more heterologous genes associated with a disorder selected from the group consisting of an ocular disorder, a liver disorder, a neurological disorder, an immune disorder, a cancer, a cardiovascular disorder, a blood coagulation disorder, a lysosomal storage disorder, or type 2 diabetes, wherein the DNA molecule lacks: (a) an origin of replication (e.g., a bacterial original of replication) and/or a drug resistance gene; and (b) a recombination site. For example, in some embodiments, the isolated linear DNA molecule lacks an origin of replication, a drug resistance gene, and a recombination site. In some embodiments, the isolated linear DNA molecule includes restriction enzyme sites, e.g., wherein each restriction enzyme site is positioned between the heterologous gene and a terminal repeat sequence.

The disorder may be an ocular disorder that is a retinal dystrophy (e.g., a Mendelian-heritable retinal dystrophy). The retinal dystrophy may be selected from the group consisting of leber's congenital amaurosis (LCA), Stargardt Disease, pseudoxanthoma elasticum, rod cone dystrophy, exudative vitreoretinopathy, Joubert Syndrome, CSNB-1C, age-related macular degeneration, retinitis pigmentosa, stickler syndrome, microcephaly and chorioretinopathy, retinitis pigmentosa, CSNB 2, Usher syndrome, and Wagner syndrome.

In some embodiments, the disorder is a coagulation disorder, such as hemophilia (e.g., hemophilia A or hemophilia B), von Willebrand's disease, factor XI deficiency, a fibrinogen disorder, or a vitamin K deficiency. The coagulation disorder may be characterized by a mutation in a gene encoding for fibrinogen, prothrombin, factor V, factor VII, factor VIII, factor X, factor XI, factor XIII, or an enzyme involved in posttranslational modifications thereof, or an enzyme involved in vitamin K metabolism. In some embodiments, the coagulation disorder is characterized by a mutation in FGA, FGB, FGG, F2, F5, F7, F10, F11, F13A, F13B, LMAN1, MCFD2, GGCX, or VKORC1.

The disorder may be a neurological disorder, e.g., a neurodegenerative disease. The neurodegenerative disease may be selected from the group consisting of Alzheimer's disease, Parkinson's disease, or multiple sclerosis. The neurodegenerative disease may be an autoimmune disease of the central nervous system (CNS), such as multiple sclerosis, encephalomyelitis, a paraneoplastic syndrome, autoimmune inner ear disease, or opsoclonus myoclonus syndrome. The neurological disorder may be a cerebral infarction, spinal cord injury, central nervous system disorder, a neuropsychiatric disorder, or a channelopathy (e.g., epilepsy or migraine). The neurological disorder may be an anxiety disorder, a mood disorder, a childhood disorder, a cognitive disorder, schizophrenia, a substance related disorders, or an eating disorders. In some embodiments, the neurological disorder is a symptom of a cerebral infarction, stroke, traumatic brain injury, or spinal cord injury.

In some embodiments, the disorder is a lysosomal storage disorder, such as Tay-Sachs disease, Gaucher disease, Fabry disease, Pompe disease, Niemann-Pick disease, or mucopolysaccharidosis (MPS).

In some embodiments, the disorder is a cardiovascular disorder, such as a degenerative heart disease, a coronary artery disease, an ischemia, angina pectoris, an acute coronary syndrome, a peripheral vascular disease, a peripheral arterial disease, a cerebrovascular disease, or atherosclerosis. The cardiovascular disorder may be a degenerative heart disease selected from the group consisting of an ischemic cardiomyopathy, a conduction disease, and a congenital defect.

The disorder may be an immune disorder, e.g., an autoimmune disorder. The autoimmune disorder may be type 1 diabetes, multiple sclerosis, rheumatoid arthritis, lupus, encephalomyelitis, a paraneoplastic syndrome, autoimmune inner ear disease, or opsoclonus myoclonus syndrome, autoimmune hepatitis, uveitis, autoimmune retinopathy, neuromyelitis optica, psoriatic arthritis, psoriasis, myasthenia gravis, chronic Lyme disease, celiac disease, chronic inflammatory demyelinating polyneuropathy, peripheral neuropathy, fibromyalgia, Hashimoto's thyroiditis, ulcerative colitis, or Kawasaki disease.

The disorder may be a liver disease, e.g., a liver disease selected from the group consisting of hepatitis, Alagille syndrome, biliary atresia, liver cancer, cirrhosis, a cystic disease, Caroli's syndrome, congenital hepatic fibrosis, fatty liver, galactosemia, primary sclerosing cholangitis, tyrosinemia, glycogen storage disease, Wilson's disease, and an endocrine deficiency. The liver disease may be a liver cancer selected from the group consisting of a hepatocellular hyperplasia, a hepatocellular adenomas, a focal nodular hyperplasia, or a hepatocellular carcinoma.

In some embodiments, the disorder is a cancer, such as a blood cancer (e.g., acute lymphoblastic leukemia, acute myeloblastic leukemia, chromic myelogenous leukemia, Hodgkin's disease, multiple myeloma, and non-Hodgkin's lymphoma) or a solid tissue cancer (e.g., liver cancer, kidney cancer, a breast cancer, a prostate cancer, a gastric cancer, an esophageal cancer, a stomach cancer, an intestinal cancer, a colorectal cancer, a bladder cancer, a head and neck cancer, a skin cancer, or a brain cancer).

In some embodiments, the disorder is a recessively inherited disorder. In some embodiments, the disorder is a Mendelian-inherited disorder.

In another aspect, the invention provides an isolated linear DNA molecule having a plurality of identical amplicons, wherein each of the plurality of identical amplicons includes one or more therapeutic nucleic acids. In some embodiments, the DNA molecule (a) lacks an origin of replication and/or a drug resistance gene; (b) lacks a recombination site; and (c) comprises a terminal repeat sequence. For example, in some embodiments, the isolated linear DNA molecule lacks an origin of replication, a drug resistance gene, and a recombination site. In some embodiments, the isolated linear DNA molecule includes restriction enzyme sites, e.g., wherein each restriction enzyme site is positioned between the heterologous gene and a terminal repeat sequence.

In some embodiments, the isolated linear DNA molecule includes a terminal repeat sequence (e.g., one or more inverted terminal repeat (ITR) sequences (e.g., two ITR sequences) or portion thereof (e.g., two A elements, B elements, C elements, or D elements), or long terminal repeat (LTR) sequences (e.g., two LTR sequences)). In some embodiments, the terminal repeat sequence is at least 10 base pairs (bp) in length (e.g., from 10 bp to 500 bp, from 12 bp to 400 bp, from 14 bp to 300 bp, from 16 bp to 250 bp, from 18 bp to 200 bp, from 20 bp to 180 bp, from 25 bp to 170 bp, from 30 bp to 160 bp, or from 50 bp to 150 bp, e.g., from 10 bp to 15 bp, from 15 bp to 20 bp, from 20 bp to 25 bp, from 25 bp to 30 bp, from 30 bp to 35 bp, from 35 bp to 40 bp, from 40 bp to 45 bp, from 45 bp to 50 bp, from 50 bp to 55 bp, from 55 bp to 60 bp, from 60 bp to 65 bp, from 65 bp to 70 bp, from 70 bp to 80 bp, from 80 bp to 90 bp, from 90 bp to 100 bp, from 100 bp to 150 bp, from 150 bp to 200 bp, from 200 bp to 300 bp, from 300 bp to 400 bp, or from 400 bp to 500 bp, e.g., 10 bp, 11 bp, 12 bp, 13 bp, 14 bp, 15 bp, 16 bp, 17 bp, 18 bp, 19 bp, 20 bp, 21 bp, 22 bp, 23 bp, 24 bp, 25 bp, 26 bp, 27 bp, 28 bp, 29 bp, 30 bp, 31 bp, 32 bp, 33 bp, 34 bp, 35 bp, 36 bp, 37 bp, 38 bp, 39 bp, 40 bp, 41 bp, 42 bp, 43 bp, 44 bp, 45 bp, 46 bp, 47 bp, 48 bp, 49 bp, 50 bp, 51 bp, 52 bp, 53 bp, 54 bp, 55 bp, 56 bp, 57 bp, 58 bp, 59 bp, 60 bp, 61 bp, 62 bp, 63 bp, 64 bp, 65 bp, 66 bp, 67 bp, 68 bp, 69 bp, 70 bp, 71 bp, 72 bp, 73 bp, 74 bp, 75 bp, 76 bp, 77 bp, 78 bp, 79 bp, 80 bp, 81 bp, 82 bp, 83 bp, 84 bp, 85 bp, 86 bp, 87 bp, 88 bp, 89 bp, 90 bp, 91 bp, 92 bp, 93 bp, 94 bp, 95 bp, 96 bp, 97 bp, 98 bp, 99 bp, 100 bp, 101 bp, 102 bp, 103 bp, 104 bp, 105 bp, 106 bp, 107 bp, 108 bp, 109 bp, 110 bp, 111 bp, 112 bp, 113 bp, 114 bp, 115 bp, 116 bp, 117 bp, 118 bp, 119 bp, 120 bp, 121 bp, 122 bp, 123 bp, 124 bp, 125 bp, 126 bp, 127 bp, 128 bp, 129 bp, 130 bp, 131 bp, 132 bp, 133 bp, 134 bp, 135 bp, 136 bp, 137 bp, 138 bp, 139 bp, 140 bp, 141 bp, 142 bp, 143 bp, 144 bp, 145 bp, 146 bp, 147 bp, 148 bp, 149 bp, 150 bp, or more). In some embodiments, isolated linear DNA molecule includes a DD element. In some embodiments, the isolated linear DNA molecule includes a promoter sequence upstream of the one or more heterologous genes. In some embodiments, the isolated DNA molecule includes a polyadenylation site downstream of the one or more heterologous genes. In some embodiments, the one or more heterologous genes includes a trans-splicing molecule or a portion thereof (e.g., a binding domain).

In another aspect, the invention provides a method of producing the isolated DNA vector of any of the embodiments by: (i) providing a sample including a circular DNA vector including an AAV genome, wherein the AAV genome includes the heterologous gene; (ii) amplifying the AAV genome using polymerase-mediated rolling-circle amplification to generate a linear concatamer; (iii) digesting the concatamer using a restriction enzyme to generate multiple AAV genomes; and (iv) allowing each of the multiple AAV genomes to self-ligate to produce an isolated DNA vector including the heterologous gene.

In another aspect, the invention provides a method of producing the isolated DNA vector of any one of the above embodiments by: (i) providing a sample including a circular DNA vector including an AAV genome, wherein the AAV genome includes the heterologous gene and a terminal repeat sequence; (ii) amplifying the AAV genome using a first polymerase-mediated rolling-circle amplification to generate a first linear concatamer; (iii) digesting the first linear concatamer using a restriction enzyme to generate a first AAV genome; (iv) cloning the first AAV genome into a plasmid vector; (v) identifying a plasmid clone including a terminal repeat sequence; (vi) digesting the plasmid clone including the terminal repeat sequence to generate a second AAV genome; (vii) allowing the second AAV genome to self-ligate to produce a circular DNA template; (viii) amplifying the circular DNA template using second polymerase-mediated rolling-circle amplification to generate a second linear concatamer; (ix) digesting the second linear concatamer using a restriction enzyme to generate a third AAV genome; and (x) allowing the third AAV genome to self-ligate to produce an isolated DNA vector including the heterologous gene and the terminal repeat sequence.

In another aspect, the invention provides a cell-free method of producing the isolated DNA vector of any of the above embodiments by: (i) providing a sample including a circular DNA vector including an AAV genome, wherein the AAV genome includes the heterologous gene; (ii) amplifying the AAV genome using polymerase-mediated rolling-circle amplification to generate a linear concatamer; (iii) digesting the concatamer using a restriction enzyme to generate an AAV genome; and (iv) allowing the AAV genome to self-ligate to produce the isolated DNA vector including the heterologous gene. In some embodiments, the method further includes column purifying the isolated DNA vector including the heterologous gene to purify supercoiled DNA from the isolated DNA vector.

In another aspect, the invention provides a method of producing the isolated DNA vector of any of the above embodiments by: (i) providing a sample including a circular DNA vector including an AAV genome, wherein the AAV genome includes the heterologous gene and a DD element; (ii) amplifying the AAV genome using polymerase-mediated rolling-circle amplification to generate a linear concatamer; (iii) digesting the concatamer using a restriction enzyme to generate multiple AAV genomes; and (iv) allowing each of the multiple AAV genomes to self-ligate to produce an isolated DNA vector including the heterologous gene and the DD element.

In another aspect, the invention provides a method of producing the isolated DNA vector of any one of the above embodiments by: (i) providing a sample including a circular DNA vector including an AAV genome, wherein the AAV genome includes the heterologous gene and a DD element; (ii) amplifying the AAV genome using a first polymerase-mediated rolling-circle amplification to generate a first linear concatamer; (iii) digesting the first linear concatamer using a restriction enzyme to generate a first AAV genome; (iv) cloning the first AAV genome into a plasmid vector; (v) identifying a plasmid clone including a DD element; (vi) digesting the plasmid clone including the DD element to generate a second AAV genome; (vii) allowing the second AAV genome to self-ligate to produce a circular DNA template; (viii) amplifying the circular DNA template using second polymerase-mediated rolling-circle amplification to generate a second linear concatamer; (ix) digesting the second linear concatamer using a restriction enzyme to generate a third AAV genome; and (x) allowing the third AAV genome to self-ligate to produce an isolated DNA vector including the heterologous gene and the DD element.

In another aspect, the invention provides a cell-free method of producing the isolated DNA vector of the above embodiments by: (i) providing a sample including a circular DNA vector including an AAV genome, wherein the AAV genome includes the heterologous gene and a DD element; (ii) amplifying the AAV genome using polymerase-mediated rolling-circle amplification to generate a linear concatamer; (iii) digesting the concatamer using a restriction enzyme to generate an AAV genome; and (iv) allowing the AAV genome to self-ligate to produce a therapeutic DNA vector including the heterologous gene and the DD element.

In some embodiments of any of the aforementioned methods of producing the isolated DNA vector, the AAV genome includes a terminal repeat sequence (e.g., one or more inverted terminal repeat (ITR) sequences (e.g., two ITR sequences) or portion thereof (e.g., two A elements, B elements, C elements, or D elements), or long terminal repeat (LTR) sequences (e.g., two LTR sequences)). In some embodiments, the terminal repeat sequence is at least 10 base pairs (bp) in length (e.g., from 10 bp to 500 bp, from 12 bp to 400 bp, from 14 bp to 300 bp, from 16 bp to 250 bp, from 18 bp to 200 bp, from 20 bp to 180 bp, from 25 bp to 170 bp, from 30 bp to 160 bp, or from 50 bp to 150 bp, e.g., from 10 bp to 15 bp, from 15 bp to 20 bp, from 20 bp to 25 bp, from 25 bp to 30 bp, from 30 bp to 35 bp, from 35 bp to 40 bp, from 40 bp to 45 bp, from 45 bp to 50 bp, from 50 bp to 55 bp, from 55 bp to 60 bp, from 60 bp to 65 bp, from 65 bp to 70 bp, from 70 bp to 80 bp, from 80 bp to 90 bp, from 90 bp to 100 bp, from 100 bp to 150 bp, from 150 bp to 200 bp, from 200 bp to 300 bp, from 300 bp to 400 bp, or from 400 bp to 500 bp, e.g., 10 bp, 11 bp, 12 bp, 13 bp, 14 bp, 15 bp, 16 bp, 17 bp, 18 bp, 19 bp, 20 bp, 21 bp, 22 bp, 23 bp, 24 bp, 25 bp, 26 bp, 27 bp, 28 bp, 29 bp, 30 bp, 31 bp, 32 bp, 33 bp, 34 bp, 35 bp, 36 bp, 37 bp, 38 bp, 39 bp, 40 bp, 41 bp, 42 bp, 43 bp, 44 bp, 45 bp, 46 bp, 47 bp, 48 bp, 49 bp, 50 bp, 51 bp, 52 bp, 53 bp, 54 bp, 55 bp, 56 bp, 57 bp, 58 bp, 59 bp, 60 bp, 61 bp, 62 bp, 63 bp, 64 bp, 65 bp, 66 bp, 67 bp, 68 bp, 69 bp, 70 bp, 71 bp, 72 bp, 73 bp, 74 bp, 75 bp, 76 bp, 77 bp, 78 bp, 79 bp, 80 bp, 81 bp, 82 bp, 83 bp, 84 bp, 85 bp, 86 bp, 87 bp, 88 bp, 89 bp, 90 bp, 91 bp, 92 bp, 93 bp, 94 bp, 95 bp, 96 bp, 97 bp, 98 bp, 99 bp, 100 bp, 101 bp, 102 bp, 103 bp, 104 bp, 105 bp, 106 bp, 107 bp, 108 bp, 109 bp, 110 bp, 111 bp, 112 bp, 113 bp, 114 bp, 115 bp, 116 bp, 117 bp, 118 bp, 119 bp, 120 bp, 121 bp, 122 bp, 123 bp, 124 bp, 125 bp, 126 bp, 127 bp, 128 bp, 129 bp, 130 bp, 131 bp, 132 bp, 133 bp, 134 bp, 135 bp, 136 bp, 137 bp, 138 bp, 139 bp, 140 bp, 141 bp, 142 bp, 143 bp, 144 bp, 145 bp, 146 bp, 147 bp, 148 bp, 149 bp, 150 bp, or more). In some embodiments, the terminal repeat sequence includes a DD element. In some embodiments, the method further includes column purifying the isolated DNA vector including the heterologous gene to purify supercoiled DNA from the isolated DNA vector.

In some embodiments of any of the above methods, the polymerase-mediated rolling-circle amplification is isothermal rolling-circle amplification. The polymerase may be Phi29 DNA polymerase.

In another aspect, the invention features a pharmaceutical composition including the DNA vector of any of the above embodiments and a pharmaceutically acceptable carrier. The pharmaceutical composition may be non-immunogenic.

In another aspect, the invention features a method of inducing episomal expression (e.g., persistent episomal expression) of a heterologous gene in a subject in need thereof by administering to the subject the isolated DNA vector or composition (e.g., pharmaceutical composition) of any of the above embodiments.

In another aspect, the invention features a method of treating a disorder in a subject by administering to the subject the isolated DNA vector or composition (e.g., pharmaceutical composition) of any of the above embodiments in a therapeutically effective amount.

The isolated DNA vector or composition thereof may be administered repeatedly. The isolated DNA vector or the composition may be administered systemically. The isolated DNA vector or the composition may be administered intravenously. The isolated DNA vector or the pharmaceutical composition may be administered locally. The isolated DNA vector or the pharmaceutical composition may be administered intravitreally. In some embodiments, the disorder is an ocular disorder. The ocular disorder may be a Mendelian-heritable retinal dystrophy. The ocular disorder may be LCA, Stargardt Disease, pseudoxanthoma elasticum, rod cone dystrophy, exudative vitreoretinopathy, Joubert Syndrome, CSNB-1C, age-related macular degeneration, retinitis pigmentosa, stickler syndrome, microcephaly and chorioretinopathy, retinitis pigmentosa, CSNB 2, Usher syndrome, or Wagner syndrome.

In some embodiments, the isolated DNA vector or composition thereof is administered systemically. In some embodiments, the disorder is a coagulation disorder (e.g., hemophilia (e.g., hemophilia A or hemophilia B), von Willebrand's disease, factor XI deficiency, a fibrinogen disorder, or a vitamin K deficiency).

In another aspect, the invention provides an isolated circular DNA vector including one or more heterologous genes, wherein the DNA vector lacks an origin of replication (e.g., a bacterial origin of replication) and/or a drug-resistance gene (e.g., as part of a bacterial plasmid). For example, an isolated circular DNA vector including one or more heterologous genes may lack an origin of replication (e.g., a bacterial origin of replication). Additionally, or alternatively, an isolated circular DNA vector including one or more heterologous genes may lack a drug-resistance gene (e.g., as part of a bacterial plasmid). In some embodiments, an isolated circular DNA vector including one or more heterologous genes may lack an origin of replication (e.g., a bacterial origin of replication) and a drug-resistance gene (e.g., as part of a bacterial plasmid). In some embodiments, the DNA molecule lacks bacterial plasmid DNA. In some embodiments, the DNA vector lacks an immunogenic bacterial signature (e.g., one or more bacterial-associated CpG motifs, e.g., unmethylated CpG motifs, e.g., CpG islands). In some embodiments, the DNA vector lacks an RNA polymerase arrest site (e.g., an RNA polymerase II (RNA-PII) arrest site).

In some embodiments, the isolated circular DNA vector includes one or more heterologous genes encoding a therapeutic protein configured to treat a Mendelian-heritable retinal dystrophy (e.g., Leber's congenital amaurosis (LCA), Stargardt Disease, pseudoxanthoma elasticum, rod cone dystrophy, exudative vitreoretinopathy, Joubert Syndrome, CSNB-1C, retinitis pigmentosa, stickler syndrome, microcephaly and chorioretinopathy, retinitis pigmentosa, CSNB 2, Usher syndrome, and Wagner syndrome). For example, the one or more heterologous genes can be ABCA4, CEP290, ABCC6, RIMS1, LRP5, CC2D2A, TRPM1, IFT-172, COL11A1, TUBGCP6, KIAA1549, CACNA1F, MYO7A, VCAN, USH2A, and HMCN1.

In another aspect, the invention provides an isolated circular DNA vector having one or more heterologous genes selected from the group consisting of ABCA4, CEP290, ABCC6, RIMS1, LRP5, CC2D2A, TRPM1, IFT-172, COL11A1, TUBGCP6, KIAA1549, CACNA1F, MYO7A, VCAN, USH2A, and HMCN1, wherein the DNA vector lacks an origin of replication and/or a drug resistance gene. In some embodiments, the one or more heterologous genes encode a therapeutic protein configured to treat a retinal dystrophy (e.g., a Mendelian-heritable retinal dystrophy, e.g., a retinal dystrophy selected from the group consisting of LCA, Stargardt Disease, pseudoxanthoma elasticum, rod cone dystrophy, exudative vitreoretinopathy, Joubert Syndrome, CSNB-1C, retinitis pigmentosa, stickler syndrome, microcephaly and chorioretinopathy, retinitis pigmentosa, CSNB 2, Usher syndrome, and Wagner syndrome).

In another aspect, provided herein is an isolated circular DNA vector having one or more heterologous genes encoding a therapeutic protein (e.g., an antibody or portion thereof, a growth factor, an interleukin, an interferon, an anti-apoptosis factor, a cytokine, or an anti-diabetic factor), wherein the DNA vector lacks an origin of replication and/or a drug resistance gene.

In another aspect, the invention provides an isolated circular DNA vector having one or more heterologous genes including a trans-splicing molecule or a portion thereof (e.g., a binding domain), wherein the DNA vector lacks an origin of replication and/or a drug resistance gene.

In another aspect, the invention provides an isolated circular DNA vector comprising one or more heterologous genes encoding a liver-secreted therapeutic protein, wherein the DNA vector lacks an origin of replication and/or a drug resistance gene. In some embodiments, the therapeutic protein is secreted into blood.

In another aspect, the invention provides an isolated circular DNA vector comprising one or more heterologous genes, wherein the DNA vector: (a) includes a terminal repeat sequence; and (b) lacks an origin of replication and/or a drug resistance gene.

In yet another aspect, the invention provides an isolated linear DNA molecule having a plurality of identical amplicons, wherein each of the plurality of identical amplicons comprises a heterologous gene encoding a therapeutic protein (e.g., a therapeutic protein configured to treat a retinal dystrophy, e.g., a Mendelian-heritable retinal dystrophy), wherein the DNA molecule lacks: (a) an origin of replication and/or a drug resistance gene; and (b) a recombination site. In some embodiments, the retinal dystrophy is selected from the group consisting of LCA, Stargardt Disease, pseudoxanthoma elasticum, rod cone dystrophy, exudative vitreoretinopathy, Joubert Syndrome, CSNB-1C, retinitis pigmentosa, age related macular degeneration (AMD), stickler syndrome, microcephaly and chorioretinopathy, retinitis pigmentosa, CSNB 2, Usher syndrome, and Wagner syndrome. In some embodiments, the one or more heterologous genes are selected from the group consisting of ABCA4, CEP290, ABCC6, RIMS1, LRP5, CC2D2A, TRPM1, IFT-172, C3, COL11A1, TUBGCP6, KIAA1549, CACNA1F, MYO7A, VCAN, USH2A, and HMCN1.

In another aspect, the invention provides an isolated linear DNA molecule having a plurality of identical amplicons, wherein each of the plurality of identical amplicons including a heterologous gene selected from the group consisting of ABCA4, CEP290, ABCC6, RIMS1, LRP5, CC2D2A, TRPM1, IFT-172, C3, COL11A1, TUBGCP6, KIAA1549, CACNA1F, MYO7A, VCAN, USH2A, and HMCN1, wherein the DNA molecule lacks: (a) an origin of replication and/or a drug resistance gene; and (b) a recombination site. In some embodiments, the heterologous gene encodes a therapeutic protein configured to treat a retinal dystrophy (e.g., a Mendelian-heritable retinal dystrophy, e.g., LCA, Stargardt Disease, pseudoxanthoma elasticum, rod cone dystrophy, exudative vitreoretinopathy, Joubert Syndrome, CSNB-1C, retinitis pigmentosa, AMD, stickler syndrome, microcephaly and chorioretinopathy, retinitis pigmentosa, CSNB 2, Usher syndrome, or Wagner syndrome).

In another aspect, provided herein is an isolated linear DNA molecule having a plurality of identical amplicons, wherein each of the plurality of identical amplicons includes a heterologous gene encoding antibody or portion thereof, a coagulation factor, an enzyme, a growth factor, a hormone, an interleukin, an interferon, an anti-apoptosis factor, an anti-tumor factor, a cytokine, and an anti-diabetic factor, wherein the DNA molecule lacks: (a) an origin of replication and/or a drug resistance gene; and (b) a recombination site.

In yet another aspect, the invention features an isolated linear DNA molecule having a plurality of identical amplicons, wherein each of the plurality of identical amplicons includes a heterologous gene comprising a trans-splicing molecule or a portion thereof (e.g., a binding domain), wherein the DNA molecule lacks: (a) an origin of replication and/or a drug resistance gene; and (b) a recombination site.

In another aspect, the invention provides an isolated linear DNA molecule having a plurality of identical amplicons, wherein each of the plurality of identical amplicons includes a heterologous gene encoding a liver-secreted therapeutic protein (e.g., a therapeutic protein secreted into blood), wherein the DNA molecule lacks an origin of replication and/or a drug resistance gene.

In some embodiments of any of the preceding aspects, the circular DNA vector or linear DNA molecule further includes one or more terminal repeat sequences (e.g., one or more inverted terminal repeat (ITR) sequences (e.g., two ITR sequences) or portion thereof (e.g., two A elements, B elements, C elements, or D elements), or long terminal repeat (LTR) sequences (e.g., two LTR sequences)). In some embodiments, the terminal repeat sequence is at least 10 base pairs (bp) in length (e.g., from 10 bp to 500 bp, from 12 bp to 400 bp, from 14 bp to 300 bp, from 16 bp to 250 bp, from 18 bp to 200 bp, from 20 bp to 180 bp, from 25 bp to 170 bp, from 30 bp to 160 bp, or from 50 bp to 150 bp, e.g., from 10 bp to 15 bp, from 15 bp to 20 bp, from 20 bp to 25 bp, from 25 bp to 30 bp, from 30 bp to 35 bp, from 35 bp to 40 bp, from 40 bp to 45 bp, from 45 bp to 50 bp, from 50 bp to 55 bp, from 55 bp to 60 bp, from 60 bp to 65 bp, from 65 bp to 70 bp, from 70 bp to 80 bp, from 80 bp to 90 bp, from 90 bp to 100 bp, from 100 bp to 150 bp, from 150 bp to 200 bp, from 200 bp to 300 bp, from 300 bp to 400 bp, or from 400 bp to 500 bp, e.g., 10 bp, 11 bp, 12 bp, 13 bp, 14 bp, 15 bp, 16 bp, 17 bp, 18 bp, 19 bp, 20 bp, 21 bp, 22 bp, 23 bp, 24 bp, 25 bp, 26 bp, 27 bp, 28 bp, 29 bp, 30 bp, 31 bp, 32 bp, 33 bp, 34 bp, 35 bp, 36 bp, 37 bp, 38 bp, 39 bp, 40 bp, 41 bp, 42 bp, 43 bp, 44 bp, 45 bp, 46 bp, 47 bp, 48 bp, 49 bp, 50 bp, 51 bp, 52 bp, 53 bp, 54 bp, 55 bp, 56 bp, 57 bp, 58 bp, 59 bp, 60 bp, 61 bp, 62 bp, 63 bp, 64 bp, 65 bp, 66 bp, 67 bp, 68 bp, 69 bp, 70 bp, 71 bp, 72 bp, 73 bp, 74 bp, 75 bp, 76 bp, 77 bp, 78 bp, 79 bp, 80 bp, 81 bp, 82 bp, 83 bp, 84 bp, 85 bp, 86 bp, 87 bp, 88 bp, 89 bp, 90 bp, 91 bp, 92 bp, 93 bp, 94 bp, 95 bp, 96 bp, 97 bp, 98 bp, 99 bp, 100 bp, 101 bp, 102 bp, 103 bp, 104 bp, 105 bp, 106 bp, 107 bp, 108 bp, 109 bp, 110 bp, 111 bp, 112 bp, 113 bp, 114 bp, 115 bp, 116 bp, 117 bp, 118 bp, 119 bp, 120 bp, 121 bp, 122 bp, 123 bp, 124 bp, 125 bp, 126 bp, 127 bp, 128 bp, 129 bp, 130 bp, 131 bp, 132 bp, 133 bp, 134 bp, 135 bp, 136 bp, 137 bp, 138 bp, 139 bp, 140 bp, 141 bp, 142 bp, 143 bp, 144 bp, 145 bp, 146 bp, 147 bp, 148 bp, 149 bp, 150 bp, or more). In some embodiments, the DNA vector includes a DD element).

In another aspect, the invention features an isolated linear DNA molecule including a plurality of identical amplicons, wherein each of the plurality of identical amplicons includes a heterologous gene, wherein the DNA molecule: (a) comprises a terminal repeat sequence (e.g., any of the aforementioned terminal repeat sequences); and (b) lacks an origin of replication and/or a drug resistance gene.

In some embodiments, the circular DNA vector further includes a heterologous gene (e.g., one or more heterologous genes). In some embodiments, the one or more heterologous genes are greater than 4.5 Kb in length (e.g., the one or more heterologous genes, together or each alone, are from 4.5 Kb to 25 Kb, from 4.6 Kb to 24 Kb, from 4.7 Kb to 23 Kb, from 4.8 Kb to 22 Kb, from 4.9 Kb to 21 Kb, from 5.0 Kb to 20 Kb, from 5.5 Kb to 18 Kb, from 6.0 Kb to 17 Kb, from 6.5 Kb to 16 Kb, from 7.0 Kb to 15 Kb, from 7.5 Kb to 14 Kb, from 8.0 Kb to 13 Kb, from 8.5 Kb to 12.5 Kb, from 9.0 Kb to 12.0 Kb, from 9.5 Kb to 11.5 Kb, or from 10.0 Kb to 11.0 Kb in length, e.g., from 4.5 Kb to 8 Kb, from 8 Kb to 10 Kb, from 10 Kb to 15 Kb, from 15 Kb to 20 Kb in length, or greater, e.g., from 4.5 Kb to 5.0 Kb, from 5.0 Kb to 5.5 Kb, from 5.5 Kb to 6.0 Kb, from 6.0 Kb to 6.5 Kb, from 6.5 Kb to 7.0 Kb, from 7.0 Kb to 7.5 Kb, from 7.5 Kb to 8.0 Kb, from 8.0 Kb to 8.5 Kb, from 8.5 Kb to 9.0 Kb, from 9.0 Kb to 9.5 Kb, from 9.5 Kb to 10 Kb, from 10 Kb to 10.5 Kb, from 10.5 Kb to 11 Kb, from 11 Kb to 11.5 Kb, from 11.5 Kb to 12 Kb, from 12 Kb to 12.5 Kb, from 12.5 Kb to 13 Kb, from 13 Kb to 13.5 Kb, from 13.5 Kb to 14 Kb, from 14 Kb to 14.5 Kb, from 14.5 Kb to 15 Kb, from 15 Kb to 15.5 Kb, from 15.5 Kb to 16 Kb, from 16 Kb to 16.5 Kb, from 16.5 Kb to 17 Kb, from 17 Kb to 17.5 Kb, from 17.5 Kb to 18 Kb, from 18 Kb to 18.5 Kb, from 18.5 Kb to 19 Kb, from 19 Kb to 19.5 Kb, from 19.5 Kb to 20 Kb, from 20 Kb to 21 Kb, from 21 Kb to 22 Kb, from 22 Kb to 23 Kb, from 23 Kb to 24 Kb, from 24 Kb to 25 Kb in length, or greater, e.g., about 4.5 Kb, about 5.0 Kb, about 5.5 Kb, about 6.0 Kb, about 6.5 Kb, about 7.0 Kb, about 7.5 Kb, about 8.0 Kb, about 8.5 Kb, about 9.0 Kb, about 9.5 Kb, about 10 Kb, about 11 Kb, about 12 Kb, about 13 Kb, about 14 Kb, about 15 Kb, about 16 Kb, about 17 Kb, about 18 Kb, about 19 Kb, about 20 Kb in length, or greater).

In embodiments of circular DNA vectors having two or more heterologous genes, the heterologous genes may be the same gene or different genes (e.g., they may encode peptides that interact functionally (e.g., as part of a signaling pathway) or structurally (e.g., through dimerization, e.g., a heavy and light chain of an antibody or fragment thereof)).

In some embodiments, the heterologous gene of the circular DNA vector includes one or more trans-splicing molecules or a portion thereof (e.g., a binding domain).

In some embodiments, the circular DNA vector is a monomeric circular vector, a dimeric circular vector, a trimeric circular vector, etc. In some embodiments, the DNA vector is a monomeric circular vector. In some embodiments, the circular DNA vector (e.g., monomeric circular vector) is double stranded. In some embodiments, the circular DNA vector is supercoiled (e.g., monomeric supercoiled).

In some embodiments, the circular DNA vector includes a promoter sequence upstream of the one or more heterologous genes. Additionally, or alternatively, the circular DNA vector can include a polyadenylation site downstream of the one or more heterologous genes. Thus, in some embodiments, the circular DNA vector includes the following elements, operatively linked from 5' to 3' or from 3' to 5': (i) a promoter sequence; (ii) one or more heterologous genes; (iii) a polyadenylation site; and (iv) a terminal repeat sequence (e.g., one or more terminal repeat sequences (e.g., one or more inverted terminal repeat (ITR) sequences (e.g., two ITR sequences) or long terminal repeat (LTR) sequences (e.g., two LTR sequences))).

In another aspect, the invention features methods of producing an isolated circular DNA vector (e.g., any of the circular DNA vectors described herein). The method includes: (i) providing a sample including a circular DNA molecule including an AAV genome (e.g., a recombinant AAV (rAAV) genome, e.g., an AAV episome), wherein the AAV genome includes a heterologous gene and a terminal repeat sequence (e.g., one or more terminal repeat sequences (e.g., one or more inverted terminal repeat (ITR) sequences (e.g., two ITR sequences) or long terminal repeat (LTR) sequences (e.g., two LTR sequences))); (ii) amplifying the AAV genome using polymerase (e.g., phage-polymerase)-mediated rolling-circle amplification (e.g., an isothermal polymerase (e.g., phage polymerase)-mediated rolling circle amplification) to generate a linear concatamer; (iii) digesting the concatamer using a restriction enzyme to generate an AAV genome; and (iv) allowing the AAV genome to self-ligate to produce an isolated DNA vector including the heterologous gene and the terminal repeat sequence. In some embodiments, the method further includes column purifying the isolated DNA vector to purify supercoiled DNA from the isolated DNA vector. The supercoiled DNA can be monomeric supercoiled DNA. In some embodiments, open relaxed circular DNA is separated from supercoiled DNA in the column purification and can be discarded. In some embodiments, the heterologous gene is any of the heterologous genes described in any previous aspect, e.g., a heterologous gene that encodes a therapeutic protein configured to treat a retinal dystrophy (e.g., a Mendelian-heritable retinal dystrophy, a retinal dystrophy selected from the group consisting of LCA, Stargardt Disease, pseudoxanthoma elasticum, rod cone dystrophy, exudative vitreoretinopathy, Joubert Syndrome, CSNB-1C, retinitis pigmentosa, age related macular degeneration (AMD), stickler syndrome, microcephaly and chorioretinopathy, retinitis pigmentosa, CSNB 2, Usher syndrome, and Wagner syndrome; a heterologous gene that includes one or more of the following: ABCA4, CEP290, ABCC6, RIMS1, LRP5, CC2D2A, TRPM1, IFT-172, C3, COL11A1, TUBGCP6, KIAA1549, CACNA1F, MYO7A, VCAN, USH2A, and HMCN1; a heterologous gene that encodes antibody or portion thereof, a coagulation factor, an enzyme, a growth factor, a hormone, an interleukin, an interferon, an anti-apoptosis factor, an anti-tumor factor, a cytokine, and an anti-diabetic factor; and/or a heterologous gene that is a trans-splicing molecule or a portion thereof (e.g., a binding domain).

The polymerase can be a thermophilic polymerase or a polymerase having high processivity through GC-rich residues (e.g., compared to a reference polymerase). In some embodiments, the polymerase is a phage polymerase. In some embodiments, the phage polymerase is Phi29 DNA polymerase.

In another aspect, the invention provides a method of producing an isolated circular DNA vector, the method including: (i) providing a sample including a circular DNA molecule including an AAV genome (e.g., an AAV episome), wherein the AAV genome includes a heterologous gene and a DD element; (ii) amplifying the AAV genome using a first polymerase-mediated rolling-circle amplification (e.g., an isothermal polymerase-mediated rolling circle amplification) to generate a first linear concatamer; (iii) digesting the first linear concatamer using a restriction enzyme to generate a first AAV genome; (iv) cloning the first AAV genome into a plasmid vector; (v) identifying a plasmid clone including a terminal repeat sequence (e.g., one or more terminal repeat sequences (e.g., one or more inverted terminal repeat (ITR) sequences (e.g., two ITR sequences) or long terminal repeat (LTR) sequences (e.g., two LTR sequences))); (vi) digesting the plasmid clone including the terminal repeat sequence to generate a second AAV genome; (vii) allowing the second AAV genome to self-ligate to produce a circular DNA template; (viii) amplifying the circular DNA template using second polymerase-mediated rolling-circle amplification (e.g., an isothermal polymerase-mediated rolling circle amplification) to generate a second linear concatamer; (ix) digesting the second linear concatamer using a restriction enzyme to generate a third AAV genome; and (x) allowing the third AAV genome to self-ligate to produce an isolated DNA vector including the heterologous gene and the terminal repeat sequence. In some embodiments, the polymerase used in the methods of producing circular DNA vectors is a phage polymerase (e.g., Phi29 DNA polymerase).

In another aspect, the invention features cell-free methods of producing a therapeutic circular DNA vector, the method including: (i) providing a sample including a circular DNA molecule including an AAV genome (e.g., a recombinant AAV (rAAV) genome, e.g., an AAV episome), wherein the AAV genome includes a heterologous gene and a terminal repeat sequence (e.g., one or more terminal repeat sequences (e.g., one or more inverted terminal repeat (ITR) sequences (e.g., two ITR sequences) or long terminal repeat (LTR) sequences (e.g., two LTR sequences))); (ii) amplifying the AAV genome using polymerase-mediated rolling-circle amplification (e.g., an isothermal polymerase-mediated rolling circle amplification) to generate a linear concatamer; (iii) digesting the concatamer using a restriction enzyme to generate an AAV genome; and (iv) allowing the AAV genome to self-ligate to produce an isolated circular DNA vector including the heterologous gene and the terminal repeat sequence. In some embodiments, the polymerase is a phage polymerase (e.g., Phi29 DNA polymerase). In some embodiments, the method further includes column purifying the isolated DNA vector to purify supercoiled DNA from the isolated DNA vector. The supercoiled DNA can be monomeric supercoiled DNA. In some embodiments, open relaxed circular DNA is separated from supercoiled DNA in the column purification and can be discarded.

In another aspect, provided herein is a pharmaceutical composition including any one or more of the aforementioned circular DNA vectors and a pharmaceutically acceptable carrier. In some embodiments, the pharmaceutical composition is non-immunogenic (e.g., substantially devoid of bacterial components, such as bacterial signatures, e.g., CpG motifs). In some embodiments, the pharmaceutical composition is substantially devoid of viral particles.

In another aspect, the invention features a method of inducing expression (e.g., episomal expression) of a heterologous gene in a subject in need thereof, the method including administering to the subject a pharmaceutical composition including any of the aforementioned circular DNA vectors and a pharmaceutically acceptable carrier (e.g., a non-immunogenic pharmaceutical composition).

In yet another aspect, the invention features methods of treatment using the circular DNA vectors and compositions described herein (e.g., any of the circular DNA vectors or compositions thereof of the preceding aspects). The invention includes a method of treating a disorder in a subject (e.g., an ocular disorder, e.g., a retinal dystrophy, e.g., a Mendelian-heritable retinal dystrophy), the method including administering to the subject a pharmaceutical composition of any of the preceding aspects in a therapeutically effective amount. In some embodiments, the pharmaceutical composition is administered repeatedly (e.g., about twice per day, about once per day, about five times per week, about four times per week, about three times per week, about twice per week, about once per week, about twice per month, about once per month, about once every six weeks, about once every two months, about once every three months, about once every four months, about twice per year, about once yearly, or less frequently).

In some embodiments, the pharmaceutical composition is administered locally (e.g., ocularly, (e.g., intravitreally), intrahepatic, intramuscular, by aerosolization, intradermal, transdermal, or subcutaneous). In some embodiments, the subject is being treated for leber's congenital amaurosis (LCA), Stargardt Disease, pseudoxanthoma elasticum, rod cone dystrophy, exudative vitreoretinopathy, Joubert Syndrome, CSNB-1C, age-related macular degeneration, retinitis pigmentosa, stickler syndrome, microcephaly and chorioretinopathy, retinitis pigmentosa, CSNB 2, Usher syndrome, or Wagner syndrome.

In another aspect, the invention features non-viral isolated DNA vectors that replicate the in vivo persistence of rAAV vectors by including a double D (DD) element in a DNA molecule that is devoid of bacterial plasmid DNA. Thus, the DNA vectors provided herein are non-immunogenic and are not limited to the AAV packaging capacity of about 4.5 Kb. The invention also features methods of producing the DD-containing DNA vector, pharmaceutical compositions including the DD-containing DNA vector, and methods of using the vectors described herein, e.g., for inducing episomal expression of a heterologous gene and for treating a disease associated with a defective gene.

In one aspect, the invention provides an isolated DNA vector including a DD element, wherein the DNA vector lacks an origin of replication (e.g., a bacterial origin of replication) and/or a drug-resistance gene (e.g., as part of a bacterial plasmid). For example, an isolated DNA vector including a DD element may lack an origin of replication (e.g., a bacterial origin of replication). Additionally, or alternatively, an isolated DNA vector including a DD element may lack a drug-resistance gene (e.g., as part of a bacterial plasmid). In some embodiments, an isolated DNA vector including a DD element may lack an origin of replication (e.g., a bacterial origin of replication) and a drug-resistance gene (e.g., as part of a bacterial plasmid). In some embodiments, the DNA molecule lacks bacterial plasmid DNA. In some embodiments, the DNA vector lacks an immunogenic bacterial signature (e.g., one or more bacterial-associated CpG motifs, e.g., unmethylated CpG motifs). In some embodiments, the DNA vector lacks an RNA polymerase arrest site (e.g., an RNA polymerase II (RNA-PII) arrest site).

In another aspect, the invention features an isolated DNA vector including a DD element and a bacterial origin of replication and/or a drug resistance gene (e.g., as part of a bacterial plasmid).

In some embodiments of either of the previous aspects, the DNA vector further includes a heterologous gene (e.g., one or more heterologous genes). In some embodiments, the one or more heterologous genes are greater than 4.5 Kb in length (e.g., the one or more heterologous genes, together or each alone, are from 4.5 Kb to 25 Kb, from 4.6 Kb to 24 Kb, from 4.7 Kb to 23 Kb, from 4.8 Kb to 22 Kb, from 4.9 Kb to 21 Kb, from 5.0 Kb to 20 Kb, from 5.5 Kb to 18 Kb, from 6.0 Kb to 17 Kb, from 6.5 Kb to 16 Kb, from 7.0 Kb to 15 Kb, from 7.5 Kb to 14 Kb, from 8.0 Kb to 13 Kb, from 8.5 Kb to 12.5 Kb, from 9.0 Kb to 12.0 Kb, from 9.5 Kb to 11.5 Kb, or from 10.0 Kb to 11.0 Kb in length, e.g., from 4.5 Kb to 8 Kb, from 8 Kb to 10 Kb, from 10 Kb to 15 Kb, from 15 Kb to 20 Kb in length, or greater, e.g., from 4.5 Kb to 5.0 Kb, from 5.0 Kb to 5.5 Kb, from 5.5 Kb to 6.0 Kb, from 6.0 Kb to 6.5 Kb, from 6.5 Kb to 7.0 Kb, from 7.0 Kb to 7.5 Kb, from 7.5 Kb to 8.0 Kb, from 8.0 Kb to 8.5 Kb, from 8.5 Kb to 9.0 Kb, from 9.0 Kb to 9.5 Kb, from 9.5 Kb to 10 Kb, from 10 Kb to 10.5 Kb, from 10.5 Kb to 11 Kb, from 11 Kb to 11.5 Kb, from 11.5 Kb to 12 Kb, from 12 Kb to 12.5 Kb, from 12.5 Kb to 13 Kb, from 13 Kb to 13.5 Kb, from 13.5 Kb to 14 Kb, from 14 Kb to 14.5 Kb, from 14.5 Kb to 15 Kb, from 15 Kb to 15.5 Kb, from 15.5 Kb to 16 Kb, from 16 Kb to 16.5 Kb, from 16.5 Kb to 17 Kb, from 17 Kb to 17.5 Kb, from 17.5 Kb to 18 Kb, from 18 Kb to 18.5 Kb, from 18.5 Kb to 19 Kb, from 19 Kb to 19.5 Kb, from 19.5 Kb to 20 Kb, from 20 Kb to 21 Kb, from 21 Kb to 22 Kb, from 22 Kb to 23 Kb, from 23 Kb to 24 Kb, from 24 Kb to 25 Kb in length, or greater, e.g., about 4.5 Kb, about 5.0 Kb, about 5.5 Kb, about 6.0 Kb, about 6.5 Kb, about 7.0 Kb, about 7.5 Kb, about 8.0 Kb, about 8.5 Kb, about 9.0 Kb, about 9.5 Kb, about 10 Kb, about 11 Kb, about 12 Kb, about 13 Kb, about 14 Kb, about 15 Kb, about 16 Kb, about 17 Kb, about 18 Kb, about 19 Kb, about 20 Kb in length, or greater).

In embodiments having two or more heterologous genes, the heterologous genes may be the same gene or different genes (e.g., they may encode peptides that interact functionally (e.g., as part of a signaling pathway) or structurally (e.g., through dimerization, e.g., a heavy and light chain of an antibody or fragment thereof)).

In some embodiments, the heterologous gene includes one or more trans-splicing molecules or portions thereof (e.g., a binding domain).

In some embodiments, the DNA vector is a circular vector (e.g., a monomeric circular vector, a dimeric circular vector, a trimeric circular vector, etc.). In some embodiments, the DNA vector is a monomeric circular vector.

In some embodiments, the DNA vector includes a promoter sequence upstream of the one or more heterologous genes. Additionally, or alternatively, the DNA vector can include a polyadenylation site downstream of the one or more heterologous genes. Thus, in some embodiments, the DNA vector includes the following elements, operatively linked from 5' to 3' or from 3' to 5': (i) a promoter sequence; (ii) one or more heterologous genes; (iii) a polyadenylation site; and (iv) a DD element.

In another aspect, the invention features methods of producing an isolated DNA vector (e.g., any of the DNA vectors described herein), the method including: (i) providing a sample including a circular DNA molecule including an AAV genome (e.g., a recombinant AAV (rAAV) genome, e.g., an AAV episome), wherein the AAV genome includes a heterologous gene and a DD element; (ii) amplifying the AAV genome using polymerase (e.g., phage-polymerase)-mediated rolling-circle amplification (e.g., an isothermal polymerase (e.g., phage polymerase)-mediated rolling circle amplification) to generate a linear concatamer; (iii) digesting the concatamer using a restriction enzyme to generate an AAV genome; and (iv) allowing the AAV genome to self-ligate to produce an isolated DNA vector including the heterologous gene and the DD element. The polymerase can be a thermophilic polymerase or a polymerase having high processivity through GC-rich residues (e.g., compared to a reference polymerase). In some embodiments, the polymerase is a phage polymerase. In some embodiments, the phage polymerase is Phi29 DNA polymerase.

In another aspect, the invention provides a method of producing an isolated DNA vector, the method including: (i) providing a sample including a circular DNA molecule including an AAV genome (e.g., an AAV episome), wherein the AAV genome includes a heterologous gene and a DD element; (ii) amplifying the AAV genome using a first polymerase-mediated rolling-circle amplification (e.g., an isothermal polymerase-mediated rolling circle amplification) to generate a first linear concatamer; (iii) digesting the first linear concatamer using a restriction enzyme to generate a first AAV genome; (iv) cloning the first AAV genome into a plasmid vector; (v) identifying a plasmid clone including a DD element; (vi) digesting the plasmid clone including the DD element to generate a second AAV genome; (vii) allowing the second AAV genome to self-ligate to produce a circular DNA template; (viii) amplifying the circular DNA template using second polymerase-mediated rolling-circle amplification (e.g., an isothermal polymerase-mediated rolling circle amplification) to generate a second linear concatamer; (ix) digesting the second linear concatamer using a restriction enzyme to generate a third AAV genome; and (x) allowing the third AAV genome to self-ligate to produce an isolated DNA vector including the heterologous gene and the DD element. In some embodiments, the polymerase is a phage polymerase (e.g., Phi29 DNA polymerase).

In another aspect, the invention features cell-free methods of producing a therapeutic DNA vector, the method including: (i) providing a sample including a circular DNA molecule including an AAV genome (e.g., a recombinant AAV (rAAV) genome, e.g., an AAV episome), wherein the AAV genome includes a heterologous gene and a DD element; (ii) amplifying the AAV genome using polymerase-mediated rolling-circle amplification (e.g., an isothermal polymerase-mediated rolling circle amplification) to generate a linear concatamer; (iii) digesting the concatamer using a restriction enzyme to generate an AAV genome; and (iv) allowing the AAV genome to self-ligate to produce an isolated DNA vector including the heterologous gene and the DD element. In some embodiments, the polymerase is a phage polymerase (e.g., Phi29 DNA polymerase).

In another aspect, provided herein is a pharmaceutical composition including the DNA vector of any of the preceding aspects and a pharmaceutically acceptable carrier. In some embodiments, the pharmaceutical composition is non-immunogenic (e.g., substantially devoid of immunogenic components, such as bacterial signatures, e.g., CpG motifs). In some embodiments, the pharmaceutical composition is substantially devoid of viral particles.

In another aspect, the invention features a method of inducing expression (e.g., episomal expression) of a heterologous gene in a subject in need thereof, the method including administering to the subject a pharmaceutical composition including the DNA vector of any of the preceding aspects and a pharmaceutically acceptable carrier (e.g., a non-immunogenic pharmaceutical composition). In some embodiments, the expression is induced in the liver of the subject. The liver can secrete a therapeutic protein encoded by the heterologous gene (e.g., into the blood).

In yet another aspect, the invention features methods of treatment using the DNA vectors and compositions described herein (e.g., any of the vectors or compositions of the preceding aspects). The invention includes a method of treating a disorder in a subject (e.g., an ocular disorder, e.g., a retinal dystrophy, e.g., a Mendelian-heritable retinal dystrophy), the method including administering to the subject a pharmaceutical composition of any of the preceding aspects in a therapeutically effective amount. In some embodiments, the pharmaceutical composition is administered repeatedly (e.g., about twice per day, about once per day, about five times per week, about four times per week, about three times per week, about twice per week, about once per week, about twice per month, about once per month, about once every six weeks, about once every two months, about once every three months, about once every four months, about twice per year, about once yearly, or less frequently).

In some embodiments, the pharmaceutical composition is administered locally (e.g., ocularly, (e.g., intravitreally), intrahepatic, intracerebral, intramuscular, by aerosolization, intradermal, transdermal, or subcutaneous). In other embodiments, the pharmaceutical composition is administered systemically (e.g., intravenously). In some embodiments, the subject is being treated for leber's congenital amaurosis (LCA), Stargardt Disease, pseudoxanthoma elasticum, rod cone dystrophy, exudative vitreoretinopathy, Joubert Syndrome, CSNB-1C, age-related macular degeneration, retinitis pigmentosa, stickler syndrome, microcephaly and chorioretinopathy, retinitis pigmentosa, CSNB 2, Usher syndrome, or Wagner syndrome.

BRIEF DESCRIPTION OF THE DRAWINGS

Figure 2A:
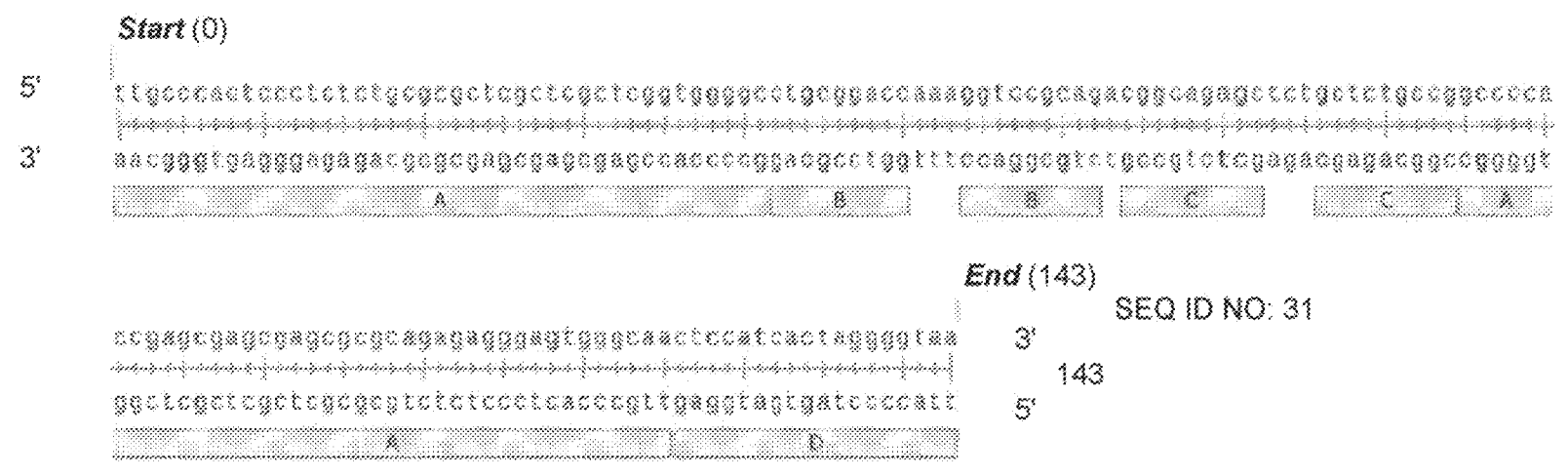
Figure 2B:
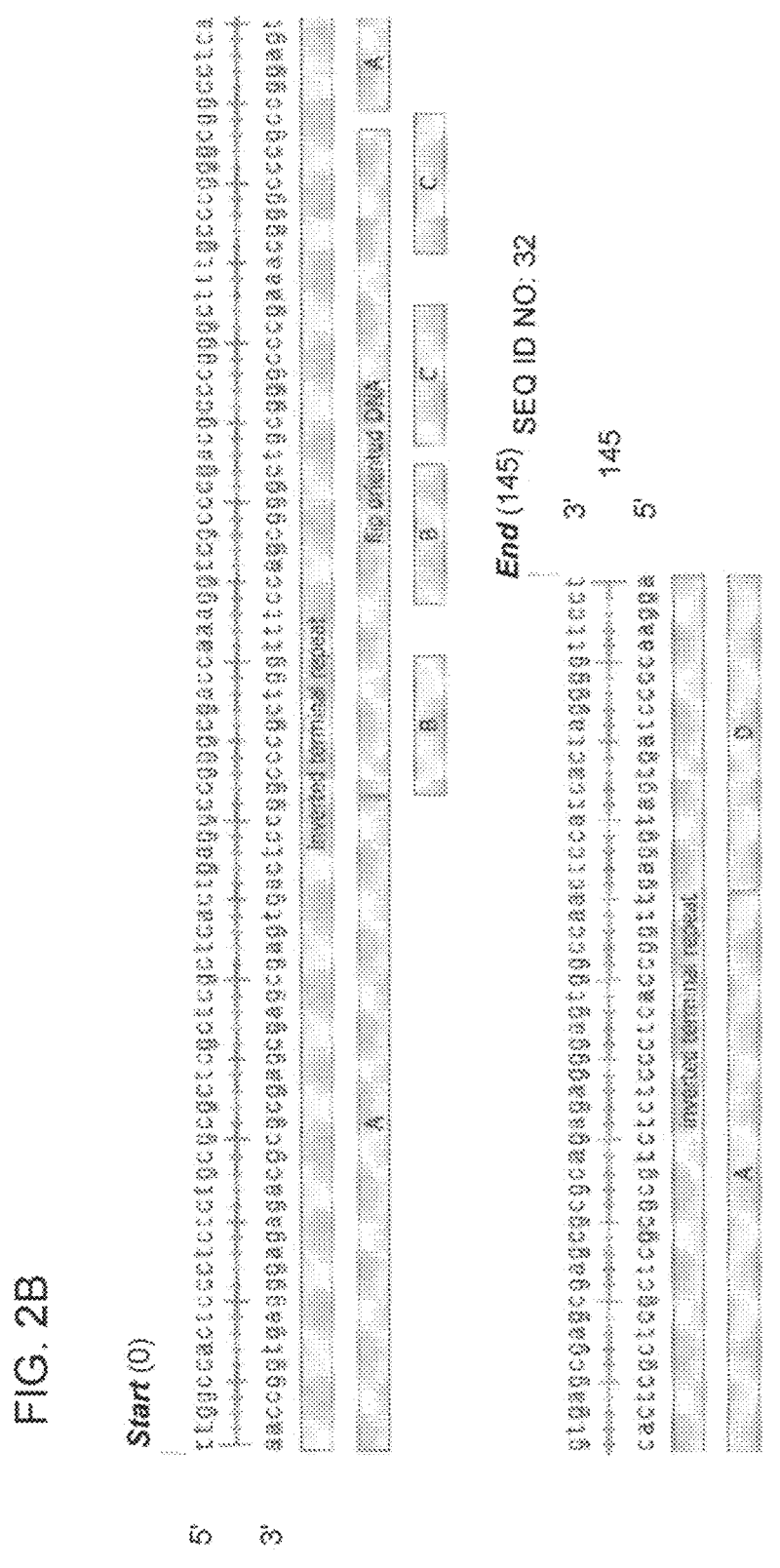
Figure 2C:
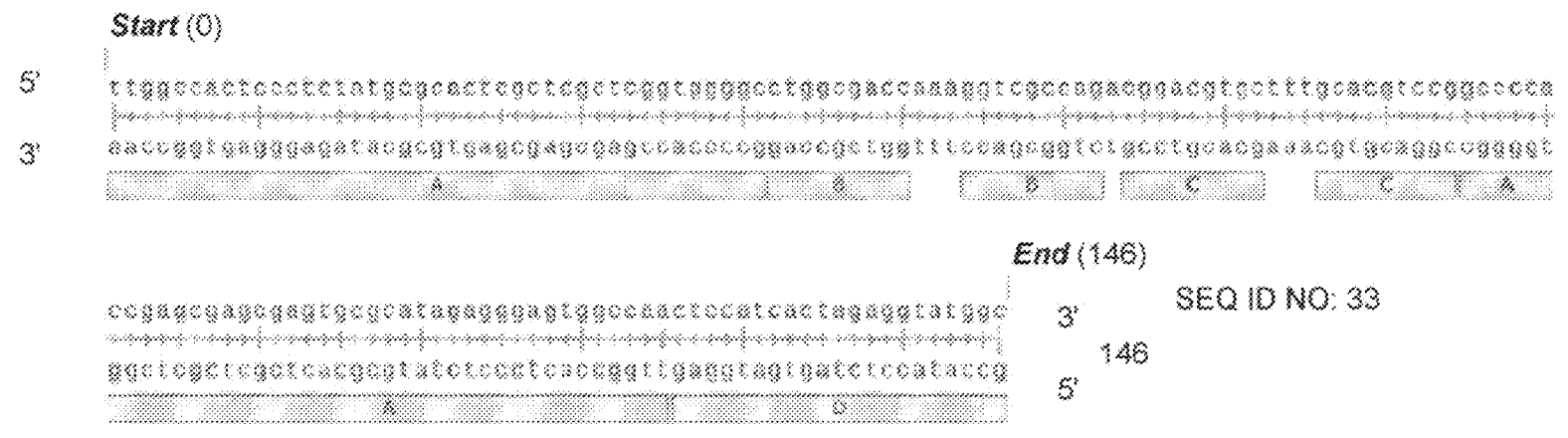
Figure 2D:
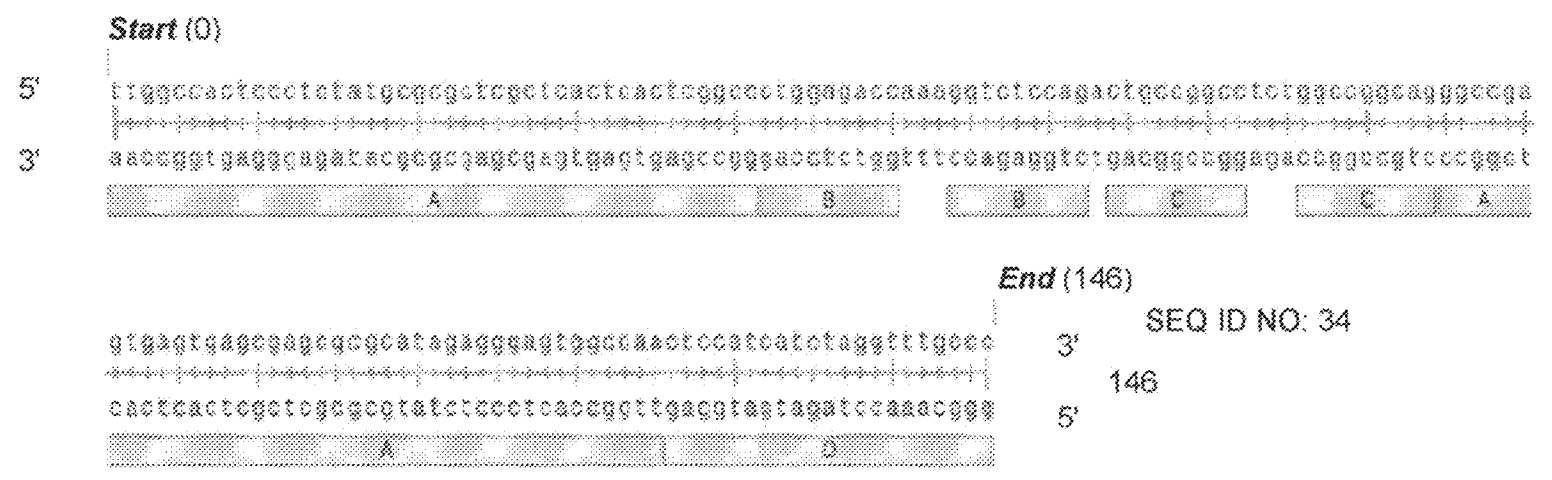
Figure 2E:
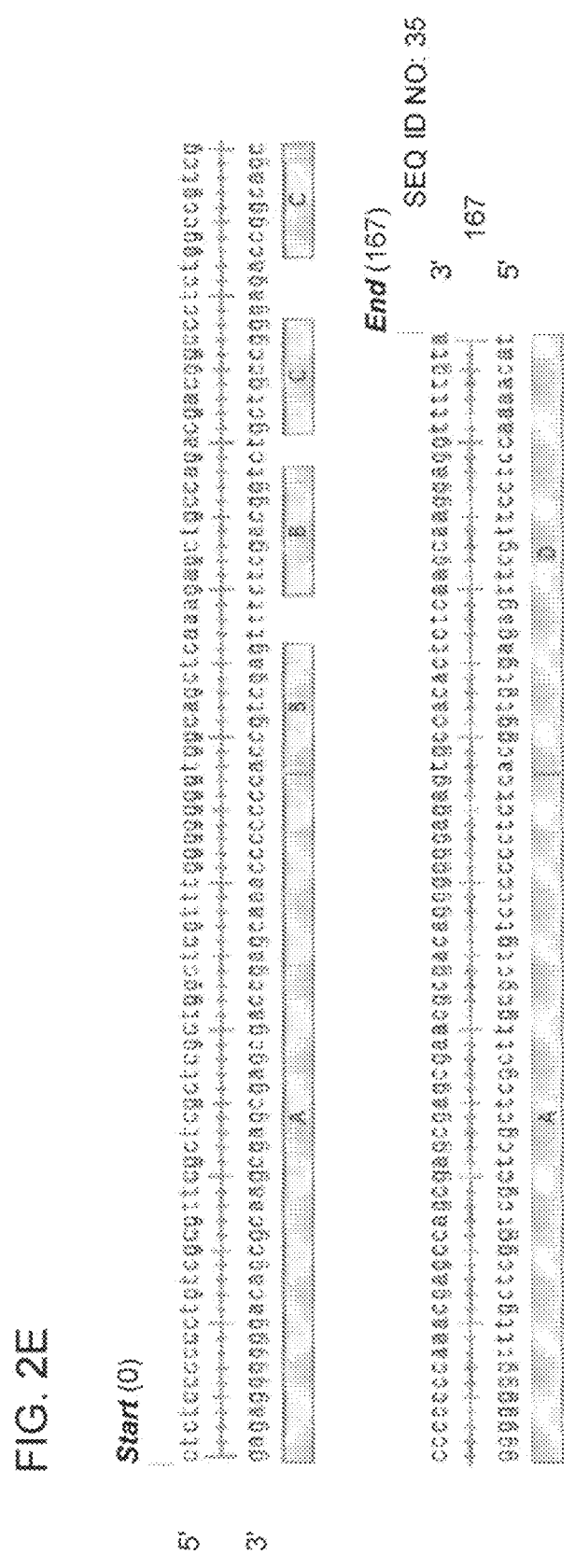
Figure 2F:
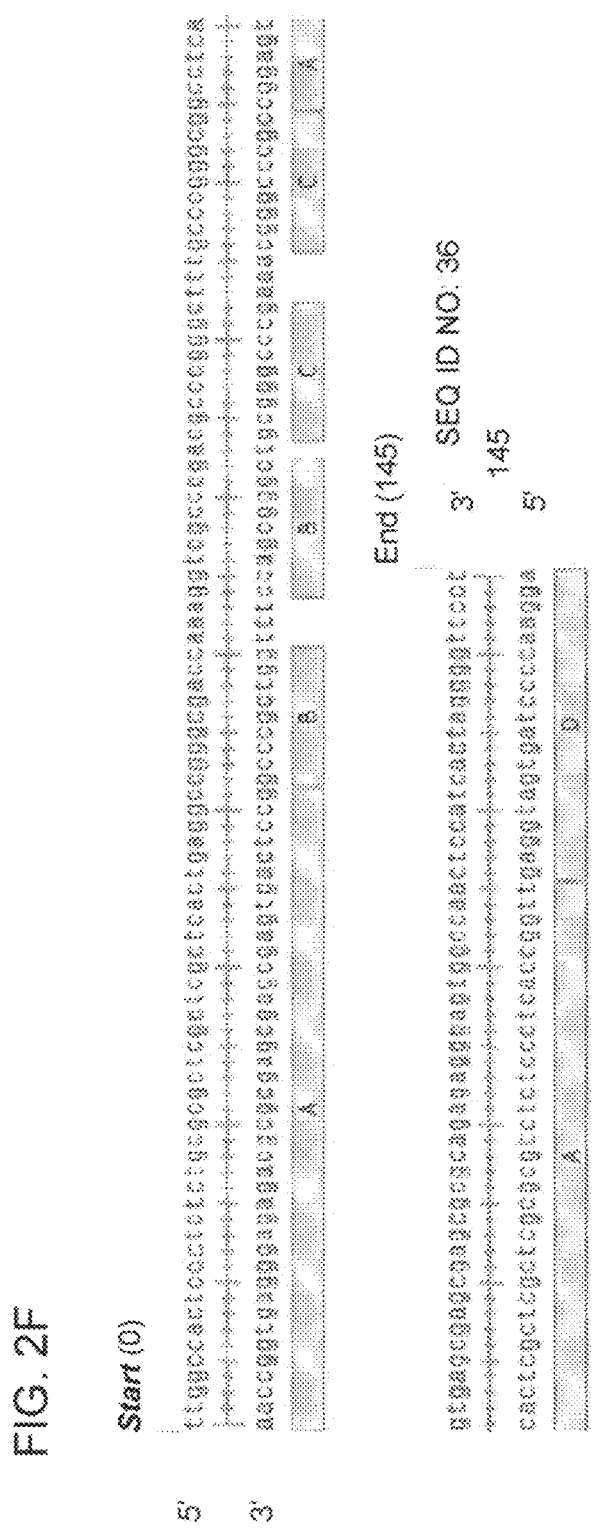
Figure 2G:
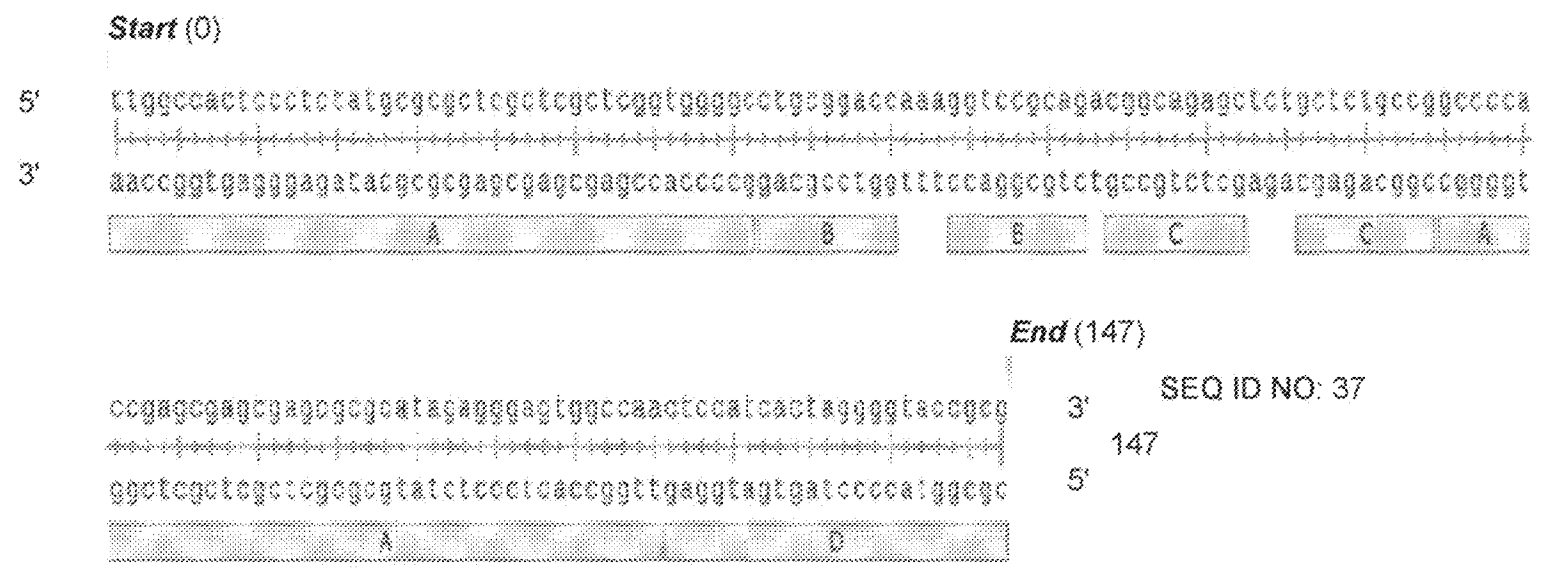

FIGS. 2A-2I are a series of illustrations showing exemplary ITR sequences for various AAV serotypes, showing locations and sequences of A, B, C, and D elements within an ITR. FIG. 2A is an illustration of an AAV1 ITR. FIG. 2B is an illustration of an AAV2 ITR. FIG. 2C is an illustration of an AAV3 ITR. FIG. 2D is an illustration of an AAV4 ITR. FIG. 2E is an illustration of an AAV5 ITR. FIG. 2F is an illustration of an AAV6 ITR. FIG. 2G is an illustration of an AAV7 ITR. FIG. 2H is an illustration of a partial AAV8 ITR. FIG. 2I is an illustration of a partial AAV9 ITR.

FIGS. 6A-6J is a series of illustrations showing exemplary sequences of various AAV2 terminal repeat sequences (in this case, DD elements). FIG. 6A is an illustration of a standard DD element including, operatively linked in a 5'-to-3' configuration, a 5' D element, a 5' A element, a 5' C element, a 3' C element, a 5' B element, a 3' B element, a 3' A element, and a 3' D element (SEQ ID NO: 9). FIG. 6B is an illustration of a standard DD element including, operatively linked in a 5'-to-3' configuration, a 5' D element, a 5' A element, a 5' B element, a 3' B element, a 5' C element, a 3' C element, a 3' A element, and a 3' D element (SEQ ID NO: 10). FIG. 6C is an illustration of a DD element without B elements including, operatively linked in a 5'-to-3' configuration, a 5' D element, a 5' A element, a 5' C element, a 3' C element, a 3' A element, and a 3' D element (SEQ ID NO: 11). FIG. 6D is an illustration of a DD element without C elements including, operatively linked in a 5'-to-3' configuration, a 5' D element, a 5' A element, a 5' B element, a 3' B element, a 3' A element, and a 3' D element (SEQ ID NO: 12). FIG. 6E is an illustration of a DD element without B and C elements including, operatively linked in a 5'-to-3' configuration, a 5' D element, a 5' A element, a 3' A element, and a 3' D element (SEQ ID NO: 13). FIG. 6F is an illustration of a DD element without A, B, and C elements including, operatively linked in a 5'-to-3' configuration, a 5' D element and a 3' D element (SEQ ID NO: 14). FIG. 6G is an illustration of a DD element including, operatively linked in a 5'-to-3' configuration, a 5' D element, a 5' A element, a 5' C element, a nucleic acid sequence in place of a 3'A element, and a 3' D element (SEQ ID NO: 15). FIG. 6H is an illustration of a DD element including, operatively linked in a 5'-to-3' configuration, a 5' D element, a 5' A element, an overlapped 5' C element with a 3' A element, and a 3' D element (SEQ ID NO: 16). FIG. 6I is an illustration of a DD element including, operatively linked in a 5'-to-3' configuration, a 5' D element, a partial 5' A element, a partial 3' A element, and a 3' D element (SEQ ID NO: 17). FIG. 6J is an illustration of a DD element including, operatively linked in a 5'-to-3' configuration, a 5' D element, a 5' A element, a partial 3' A element, and a 3' D element (SEQ ID NO: 18).

DETAILED DESCRIPTION

Figure 1:
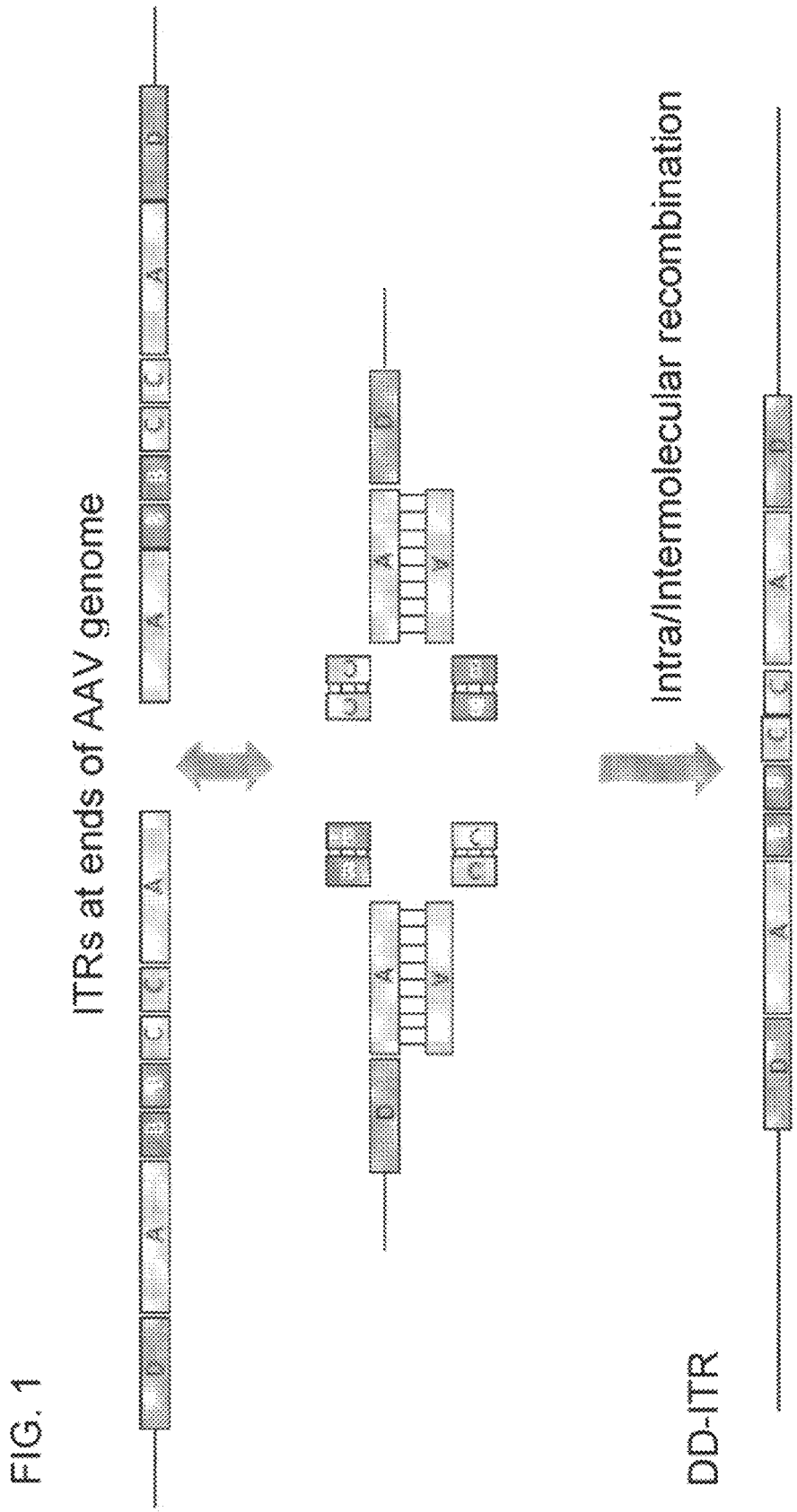
FIG. 1 is a schematic diagram showing the formation of a terminal repeat sequence (in this case, a double D (DD) element) of AAV2. AAV2 inverted terminal repeats (ITRs) are 145-bp in length and located at each end of the AAV genome. The ITR contains inverted sequences (designated as A, B, C, and D) that can base-pair and form a hairpin-like structure. A single ITR contains two "A", "B", and "C" regions, and a single "D" region. Two ITRs can recombine to form a DD element that is 165 bp in length and is similar to a single ITR but now contains two "D" regions.
Figure 3A:
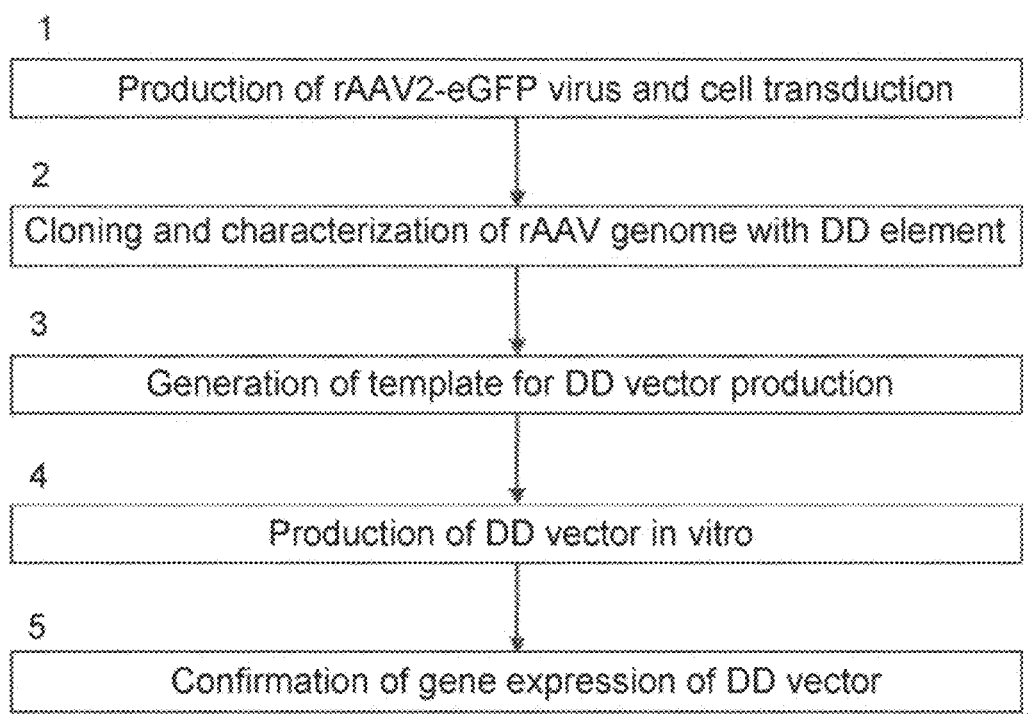
FIG. 3A is a flow-chart showing exemplary steps of DD vector production and characterization process described in the Examples. The first step is to generate or obtain a viral rAAV vector that contains an expression cassette (e.g., heterologous gene) needed for downstream function. The virus infects cells in vitro and forms a circular, double-stranded episome with a DD element. In the second major step, the circular rAAV genome is cloned from the cells and sequenced to confirm presence of a DD element. This can then be used to generate a plasmid-based template for in vitro DD vector production using rolling circle amplification (steps 3 and 4). The final step is to confirm DD vector gene expression in vitro before proceeding with in vivo studies.
Figure 3B:
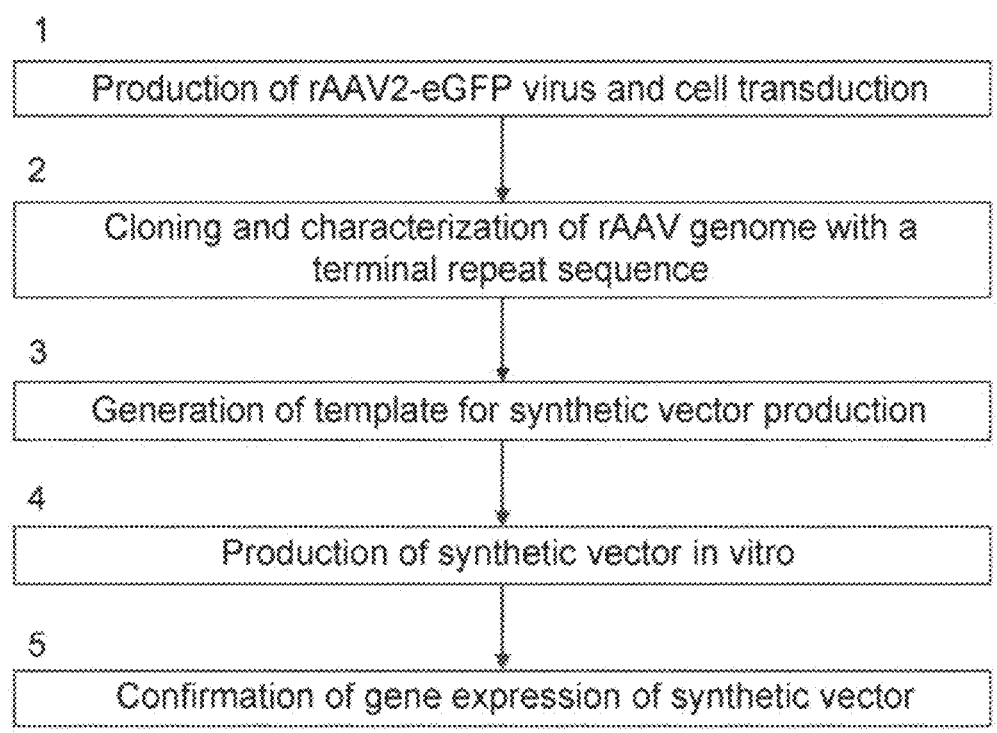
FIG. 3B is a flow-chart showing exemplary steps of synthetic circular vector production and characterization process described in the Examples. The first step is to generate or obtain a viral rAAV vector that contains an expression cassette (e.g., heterologous gene) needed for downstream function. The virus infects cells in vitro and forms a circular, double-stranded episome with a terminal repeat sequence (in this case, a DD element). In the second major step, the circular rAAV genome is cloned from the cells and sequenced to confirm presence of a DD element. This can then be used to generate a plasmid-based template for in vitro DD vector production using rolling circle amplification (steps 3 and 4). The final step is to confirm DD vector gene expression in vitro before proceeding with in vivo studies.

The present invention features non-viral DNA vectors that provide long-term transduction of quiescent cells (e.g., post-mitotic cells) in a manner similar to AAV vectors. The invention is based, in part, on the development of an in vitro (e.g., cell-free) system to synthetically produce circular AAV-like DNA vectors (e.g., DNA vectors containing a terminal repeat sequence, such as a DD element) by isothermal rolling-circle amplification and ligation-mediated circularization (as opposed to bacterial expression and site-specific recombination, for example). The present methods allow for improved scalability and manufacturing efficiency in production of circular AAV-like DNA vectors. Moreover, the vectors produced by these methods are designed to overcome many of the problems associated with plasmid-DNA vectors, e.g., problems discussed in Lu et al., *Mol. Ther.* 2017, 25(5): 1187-98, which is incorporated herein by reference in its entirety. For example, by eliminating or reducing the presence of CpG islands and/or bacterial plasmid DNA sequences such as RNAPII arrest sites, transcriptional silencing can be reduced or eliminated, resulting in increased persistence of the heterologous gene. Further, by eliminating the presence of immunogenic components (e.g., bacterial endotoxin, DNA, or RNA, or bacterial signatures, such as CpG motifs), the risk of stimulating the host immune system is reduced. Such benefits are especially advantageous in the treatment of certain disorders, such as retinal dystrophies (e.g., Mendelian-heritable retinal dystrophies).

Thus, the vectors of the present invention include synthetic DNA vectors that: (i) are substantially devoid of bacterial plasmid DNA sequences (e.g., RNAPII arrest sites, origins of replication, and/or resistance genes) and other bacterial signatures (e.g., immunogenic CpG motifs); and/or (ii) can be synthesized and amplified entirely in a test tube (e.g., replication in bacteria is unnecessary, e.g., bacterial origins of replication and bacterial resistance genes are unnecessary). In some embodiments, the vectors contain a DD element characteristics of AAV vectors. The invention allows a target cell (e.g., a retinal cell) to be transduced with a DNA vector having a heterologous gene that behaves like AAV viral DNA (e.g., having low transcriptional silencing and enhanced persistence), without needing the virus itself.

I. Definitions

Unless defined otherwise, technical and scientific terms used herein have the same meaning as commonly understood by one of ordinary skill in the art to which this invention belongs and by reference to published texts, which provide one skilled in the art with a general guide to many of the terms used in the present application. In the event of any conflicting definitions between those set forth herein and those of a referenced publication, the definition provided herein shall control.

As used herein, the term "circular vector" or "circular DNA vector" refers to a nucleic acid molecule in a circular form. Such circular form is typically capable of being amplified into concatamers by rolling circle amplification. A linear double-stranded nucleic acid having conjoined strands at its termini (e.g., covalently conjugated backbones, e.g., by hairpin loops or other structures) is not a circular vector, as used herein. The term "circular DNA vector" is used interchangeable herein with the term "covalently closed and circular DNA vector" (see, e.g., Example 2). A skilled artisan will understand that such circular vectors may include vectors that are covalently closed with supercoiling and complex DNA topology, as is described herein.

As used herein, a "Mendelian-heritable retinal dystrophy" refers to a disorder of the retina that follows a Mendelian inheritance pattern with variable penetrance (i.e., complete or reduced penetrance). A Mendelian-heritable retinal dystrophy may occur as a result of (a) single mutation in one allele (as in a dominant disorder) or (b) a single mutation in each allele (as in a recessive disorder). The mutation can be a point mutation, an insertion, a deletion, or a splice variant mutation. Exemplary Mendelian-heritable retinal dystrophies include Leber's congenital amaurosis (LCA), Stargardt Disease, pseudoxanthoma elasticum, rod cone dystrophy, exudative vitreoretinopathy, Joubert Syndrome, CSNB-1C, retinitis pigmentosa, stickler syndrome, microcephaly and chorioretinopathy, retinitis pigmentosa, CSNB 2, Usher syndrome, and Wagner syndrome. Mendelian-heritable retinal dystrophies do not include multifactorial disorders with multiple genetic associations that together the likelihood of developing the disease, such as age-related macular degeneration (AMD).

As used herein, the term "recombination site" refers to a nucleic acid sequence that is a product of site-specific recombination, which includes a first sequence that corresponds to a portion of a first recombinase attachment site and a second sequence that corresponds to a portion of a second recombinase attachment site. One example of a hybrid recombination site is attR, which is a product of site-specific recombination and includes a first sequence that corresponds to a portion of attP and a second sequence that corresponds to a portion of attB. Alternatively, recombination sites can be generated from Cre/Lox recombination. Thus, a vector generated from Cre/Lox recombination (e.g., a vector including a LoxP site) includes a recombination site, as used herein. Other site-specific recombination events that generate recombination sites involve, e.g., lambda integrase, FLP recombinase, and Kw recombinase. Nucleic acid sequences that result from non-site-specific recombination events (e.g., ITR-mediated intermolecular recombination) are not recombination sites, as defined herein.

As used herein, the term "therapeutic replacement protein" refers to a protein that is structurally similar to (e.g., structurally identical to) a protein that is endogenously expressed by a normal (e.g., healthy) individual. A therapeutic replacement protein can be administered to an individual that suffers from a disorder associated with a dysfunction of (or lack of) the protein to be replaced. In some embodiments, the therapeutic replacement protein corrects a defect in a protein resulting from a mutation (e.g., a point mutation, an insertion mutation, a deletion mutation, or a splice variant mutation) in the gene encoding the protein. Therapeutic replacement proteins do not include non-endogenous proteins, such as proteins associated with a pathogen (e.g., as part of a vaccine). Therapeutic replacement proteins may include enzymes, growth factors, hormones, interleukins, interferons, cytokines, anti-apoptosis factors, anti-diabetic factors, coagulation factors, anti-tumor factors, liver-secreted proteins, or neuroprotective factors. In some instances, the therapeutic replacement protein is monogenic.

As used herein, the term "therapeutic nucleic acid" refers to a nucleic acid that binds to (e.g., hybridizes with) a molecule (e.g., protein or nucleic acid) in the subject to confer its therapeutic effect (i.e., without necessarily being transcribed or translated). Therapeutic nucleic acids can be DNA or RNA, such as small interfering RNA (siRNA), short hairpin RNA (shRNA), microRNA (miRNA), a CRISPR molecule (e.g., guide RNA (gRNA)), an oligonucleotide (e.g., an antisense oligonucleotide), an aptamer, or a DNA vaccine. In some embodiments, the therapeutic nucleic acid may be a non-inflammatory or a non-immunogenic therapeutic nucleic acid.

As used herein, the term "terminal repeat sequence" refers to a portion of a nucleic acid molecule having a sequence of nucleotides, wherein the sequence is repeated in adjacent portions of a nucleic acid molecule. The sequences may be repeated in the same or reverse direction (e.g., ABCDABCD or ABCDDCBA, respectively). In some embodiments, for example, terminal repeat sequences can be, or be derived from (e.g., products of ligation of and/or portions of), inverted terminal repeat sequences (ITRs) or long terminal repeat sequences (LTRs). ITR-derived terminal repeat sequences may have repeated A elements, B, elements, C elements, and/or D elements (wherein A, B, C, and D elements are defined by SEQ ID NOs: 31-37 and depicted in FIGS. 2A-2H). For example, each of FIGS. 6A-6J are terminal repeat sequences, and all DD elements (e.g., SEQ ID NOs: 9 or 10) are examples of a terminal repeat sequence. A terminal repeat sequence can have a structure that results from homologous recombination (e.g., intermolecular homologous recombination or intramolecular homologous recombination). A single terminal repeat sequence, on its own, does not form a hairpin.

The term "inverted terminal repeat" or "ITR" refers to the stretch of nucleic acid that exists in AAV and/or recombinant AAV (rAAV) that can form a T-shaped palindromic structure, that is required for completing AAV lytic and latent life cycles, as described in Muzyczka and Berns, *Fields Virology* 2001, 2: 2327-2359. The terms "double-D element" and "DD element" are used interchangeably herein and refer to a type of terminal repeat sequence which is a DNA structure having a 5' D element (i.e., a nucleic acid sequence with at least 80% homology (e.g., 80%, 85%, 90%, 95%, or 100% homology) to a nucleic acid sequence selected from the group consisting of SEQ ID NOs: 1, 19, 21, 23, 25, 27, 29, 38, and 40) and a 3' D element (i.e., a nucleic acid sequence with at least 80% homology (e.g., 80%, 85%, 90%, 95%, or 100% homology) with a nucleic acid sequence selected from the group consisting of SEQ ID NOs: 8, 20, 22, 24, 26, 28, 30, 39, and 41 on the same strand of nucleic acid. In some embodiments, a 5' D element is 100% homologous to the nucleic acid sequence of SEQ ID NO: 1 and/or a 3' D element is 100% homologous to the nucleic acid sequence of SEQ ID NO: 8. DD element can be generated by joining two AAV inverted terminal repeats (ITRs) from the same molecule (intramolecular recombination) or different molecules (intermolecular recombination) by ligation, as shown in FIG. 1. Such ligation can occur between ITRs of any AAV serotype, exemplary structures of which are shown in FIGS. 2A-2I. A DD element contains two D elements on a single nucleic acid strand, and may include additional elements, such as one or more A, B, and/or C elements, or portion(s) thereof, operatively linking the 3' end of the 5' D element with the 5' end of the 3' D element. In some embodiments, no heterologous genes are present between the 3' end of the 5' D element and the 5' end of the 3' element. The sequences of exemplary DD elements derived from AAV2 are shown by each of FIGS. 6A-6J. DD elements from other AAV serotypes (e.g., AAV1, AAV3, AAV4, AAV5, AAV6, AAV7, AAV8, or AAV9) may be used. Representative 5' and 3' D elements from AAV serotypes 1-7 are provided below.

TABLE 1

Representative 5' and 3' D elements from AAV serotypes 1-7

| Description | SEQ ID NO. | Sequence |
|---|---|---|
| 5' D, AAV1 | 19 | TTACCCCTAGTGATGGAG |
| 3' D, AAV1 | 20 | CTCCATCACTAGGGGTAA |
| 5' D, AAV2 | 1 | AGGAACCCCTAGTGATGGAG |
| 3' D, AAV2 | 8 | CTCCATCACTAGGGGTTCCT |
| 5' D, AAV3 | 21 | GCCATACCTCTAGTGATGGAG |
| 3' D, AAV3 | 22 | CTCCATCACTAGAGGTATGGC |
| 5' D, AAV4 | 23 | GGGCAAACCTAGATGATGGAG |
| 3' D, AAV4 | 24 | CTCCATCATCTAGGTTTGCCC |
| 5' D, AAV5 | 25 | TACAAAACCTCCTTGCTTGAGAGTGTGGCA |
| 3' D, AAV5 | 26 | TGCCACACTCTCAAGCAAGGAGGTTTTGTA |
| 5' D, AAV6 | 27 | AGGAACCCCTAGTGATGGAG |
| 3' D, AAV6 | 28 | CTCCATCACTAGGGGTTCCT |
| 5' D, AAV7 | 29 | CGCGGTACCCCTAGTGATGGAC |
| 3' D, AAV7 | 30 | CTCCATCACTAGGGGTACCGCG |
| 5' D, AAV8 | 38 | CGCGCTACCCCTAGTGATGGAG |
| 5' D, AAV8 | 39 | CTCCATCACTAGGGGTAGCGCG |
| 5' D, AAV9 | 40 | CGCGATTACCCCTAGTGATGGAG |
| 5' D, AAV9 | 41 | CTCCATCACTAGGGGTAATCGCG |

The term "heterologous gene" refers to a gene that does not naturally occur as part of a viral genome. For instance, a heterologous gene can be a mammalian gene, e.g., a therapeutic gene (e.g., a gene that encodes a therapeutic replacement protein, an antigen-binding protein, etc.), e.g., a mammalian gene that encodes a therapeutic protein. In some embodiments, a heterologous gene encodes a protein or portion thereof that is defective or absent in the target cell and/or subject (e.g., a therapeutic replacement protein). In some embodiments, the heterologous gene contains one or more exons encoding a protein that is defective or absent in the target cell and/or subject. For example, in some embodiments, the heterologous gene includes one or more trans-splicing molecules or portions thereof (e.g., a binding domain), e.g., as described in WO 2017/087900, which is incorporated herein by reference in its entirety. In some embodiments, a heterologous gene includes a therapeutic nucleic acid, such as a therapeutic RNA (e.g., microRNA).

As used herein, a "trans-splicing molecule" has three main elements: (a) a binding domain (e.g., an oligonucleotide, e.g., an antisense oligonucleotide) that confers specificity by tethering the trans-splicing molecule to its target gene (e.g., pre-mRNA); (b) a splicing domain (e.g., a splicing domain having a 3' or 5' splice site); and (c) a coding sequence configured to be trans-spliced onto the target gene, which can replace one or more exons in the target gene (e.g., one or more mutated exons).

The term "promoter" refers to a sequence that regulates transcription of a heterologous gene operably linked to the promoter. Promoters provide the sequence sufficient to direct transcription and/or recognition sites for RNA polymerase and other transcription factors required for efficient transcription and can direct cell-specific expression. In addition to the sequence sufficient to direct transcription, a promoter sequence of the invention can also include sequences of other regulatory elements that are involved in modulating transcription (e.g., enhancers, kozak sequences, and introns). Examples of promoters known in the art and useful in the viral vectors described herein include the CMV promoter, CBA promoter, smCBA promoter, and those promoters derived from an immunoglobulin gene, SV40, or other tissue specific genes. Standard techniques are known in the art for creating functional promoters by mixing and matching known regulatory elements. "Truncated promoters" may also be generated from promoter fragments or by mix and matching fragments of known regulatory elements; for example the smCBA promoter is a truncated form of the CBA promoter.

As used herein, a vector or composition (e.g., a pharmaceutical composition containing a DNA vector of the invention) is "substantially devoid of" an immunogenic component, such as an immunogenic bacterial signature, if the composition does not elicit a measurable inflammatory response (e.g., a phenotype associated with toll-like receptor signaling) in a therapeutically relevant dose. Methods for screening compositions for presence of immunogenic components include in vitro and in vivo animal assays according to methods known in the art. In some embodiments, a vector or composition that is substantially devoid of an immunogenic component is non-immunogenic.

As used herein, the term "non-immunogenic" means that a vector or composition does not elicit a measurable inflammatory response (e.g., a phenotype associated with toll-like receptor signaling) in a therapeutically relevant dose. Methods for screening compositions for presence of immunogenic components include in vitro and in vivo animal assays according to methods known in the art. For example, a suitable in vitro assay for determining whether a vector or composition is non-immunogenic involves culturing human peripheral blood mononuclear cells (PBMC) or human PBMC-derived myeloid cells (e.g., monocytes) in the presence of the vector or composition and measuring the amount of IL-1β, IL-6, and/or IL-12 in the culture after eight hours. If the concentration of IL-1β, IL-6, and/or IL-12 is not increased in the sample containing the vector or composition, relative to a negative control, the vector or composition is non-immunogenic.

As used herein, "concatamer" refers to a nucleic acid molecule comprising multiple copies of the same or substantially the same nucleic acid sequences (e.g., subunits) that are typically linked in a series.

As used herein, the term "isolated" means artificially produced. In some embodiments, with respect to a DNA vector, the term "isolated" refers to a DNA vector that is: (i) amplified in vitro (e.g., in a cell-free environment), for example, by rolling-circle amplification or polymerase chain reaction (PCR); (ii) recombinantly produced by molecular cloning; (iii) purified, as by restriction endonuclease cleavage and gel electrophoretic fractionation, or column chromatography; or (iv) synthesized by, for example, chemical synthesis. An isolated DNA vector is one which is readily manipulable by recombinant DNA techniques well-known in the art. Thus, a nucleotide sequence contained in a vector in which 5' and 3' restriction sites are known or for which polymerase chain reaction (PCR) primer sequences have been disclosed is considered isolated, but a nucleic acid sequence existing in its native state in its natural host is not. An isolated DNA vector may be substantially purified, but need not be.

As used herein, a "vector" refers to a nucleic acid molecule capable of carrying a heterologous gene into a target cell in which the heterologous gene can then be replicated, processed, and/or expressed in the target cell. After a target cell or host cell processes the genome of the vector (e.g., by generating a DD element), the genome is not considered a vector.

As used herein, a "cell-free method" of producing a DNA vector refers to a method that does not rely on containment of any of the DNA within a host cell, such as a bacterial (e.g., E. coli) host cell, to facilitate any step of the method. For example, a cell-free method occurs within one or more synthetic containers (e.g., glass or plastic tubes or other containers) within appropriate solutions (e.g., buffered solutions), to which enzymes and other agents may be added to facilitate DNA amplification, modification, and isolation.

As used herein, a "target cell" refers to any cell that expresses a target gene and which the vector infects or is intended to infect. Vectors can infect target cells that reside in a subject (in situ) or target cells in culture. In some embodiments, target cells of the invention are post-mitotic cells. Target cells include both vertebrate and invertebrate animal cells (and cell lines of animal origin). Representative examples of vertebrate cells include mammalian cells, such as humans, rodents (e.g., rats and mice), and ungulates (e.g., cows, goats, sheep and swine). Target cells include ocular cells, such as retinal cells. Alternatively, target cells can be stem cells (e.g., pluripotent cells (i.e., a cell whose descendants can differentiate into several restricted cell types, such as hematopoietic stem cells or other stem cells) or totipotent cells (i.e., a cell whose descendants can become any cell type in an organism, e.g., embryonic stem cells, and somatic stem cells e.g., hematopoietic cells)). In yet other embodiments, target cells include oocytes, eggs, cells of an embryo, zygotes, sperm cells, and somatic (non-stem) mature cells from a variety of organs or tissues, such as hepatocytes, neural cells, muscle cells and blood cells (e.g., lymphocytes).

A "host cell" refers to any cell that harbors a DNA vector of interest. A host cell may be used as a recipient of a DNA vector as described by the disclosure. The term includes the progeny of the original cell which has been transfected. Thus, a "host cell" as used herein may refer to a cell which has been transfected with a heterologous gene (e.g., by a DNA vector described herein). It is understood that the progeny of a single parental cell may not necessarily be completely identical in morphology or in genomic or total DNA complement as the original parent, due to natural, accidental, or deliberate mutation.

As used herein, the term "subject" includes any mammal in need of the methods of treatment or prophylaxis described herein. In some embodiments, the subject is a human. Other mammals in need of such treatment or prophylaxis include dogs, cats, or other domesticated animals, horses, livestock, laboratory animals, including non-human primates, etc. The subject may be male or female. In one embodiment, the subject has a disease or disorder caused by a mutation in the target gene. In another embodiment, the subject is at risk of developing a disease or disorder caused by a mutation in the target gene. In another embodiment, the subject has shown clinical signs of a disease or disorder caused by a mutation in the target gene. The subject may be any age during which treatment or prophylactic therapy may be beneficial. For example, in some embodiments, the subject is 0-5 years of age, 5-10 years of age, 10-20 years of age, 20-30 years of age, 30-50 years of age, 50-70 years of age, or more than 70 years of age.

As used herein, an "effective amount" or "effective dose" of a vector or composition thereof refers to an amount sufficient to achieve a desired biological and/or pharmacological effect, e.g., when delivered to a cell or organism according to a selected administration form, route, and/or schedule. As will be appreciated by those of ordinary skill in this art, the absolute amount of a particular vector or composition that is effective can vary depending on such factors as the desired biological or pharmacological endpoint, the agent to be delivered, the target tissue, etc. Those of ordinary skill in the art will further understand that an "effective amount" can be contacted with cells or administered to a subject in a single dose or through use of multiple doses.

As used herein, the term "persistence" refers to the duration of time during which a gene is expressible in a cell. Persistence of a DNA vector, or persistence of a heterologous gene within a DNA vector, can be quantified relative to a reference vector, such as a control vector produced in bacteria (e.g., a circular vector produced in bacteria or having one or more bacterial signatures not present in the vector of the invention), using any gene expression characterization method known in the art. In some embodiments, a control vector lacks a DD element. Additionally, or alternatively, persistence can be quantified at any given time point following administration of the vector. For example, in some embodiments, a heterologous gene of a DNA vector of the invention persists for at least six months after administration if its expression is detected in situ six months after administration of the vector. In some embodiments, a gene "persists" in a target cell if its transcription is detectable at three months, four months, five months, six months, seven months, eight months, nine months, ten months, eleven months, one year, two years, or longer after administration. In some embodiments, a gene is said to persist if any detectable fraction of the original expression level remains (e.g., at least 1%, at least 5%, at least 10%, at least 20%, at least 30%, at least 40%, at least 50%, at least 70%, or at least 100% of the original expression level) after a given period of time after administration (e.g., three months, four months, five months, six months, seven months, eight months, nine months, ten months, eleven months, one year, two years, or longer after administration).

As used herein, a "mutation" refers to any aberrant nucleic acid sequence that causes a defective (e.g., non-functional, reduced function, aberrant function, less than normal amounts produced) protein product. Mutations include base pair mutations (e.g., single nucleotide polymorphisms), missense mutations, frameshift mutations, deletions, insertions, and splice mutations.

As used herein, the terms "disorder associated with a mutation" or "mutation associated with a disorder" refer to a correlation between a disorder and a mutation. In some embodiments, a disorder associated with a mutation is known or suspected to be wholly or partially, or directly or indirectly, caused by the mutation. For example, a subject having the mutation may be at risk of developing the disorder, and the risk may additionally depend on other factors, such as other (e.g., independent) mutations (e.g., in the same or a different gene), or environmental factors.

As used herein, the term "immune disorder" refers to a dysfunction of the immune system characterized by a compromised (underactive) immune function (e.g., an inability to mount a suitable immune response to foreign or pathogenic antigen) or an overactive immune function (e.g., an inability to distinguish endogenous "self" antigen from foreign or pathogenic antigen, thereby leading to, e.g., aberrant inflammation, chronic infection, and/or autoimmunity). Immune disorders do not include normal immune responses (e.g., normal inflammation, infection, and pathogen-clearance). Thus, a vaccine, for example, is not a treatment for an immune disorder, as defined herein.

As used herein, the term "treatment," or a grammatical derivation thereof, is defined as reducing the progression of a disease, reducing the severity of a disease symptom, retarding progression of a disease symptom, removing a disease symptom, or delaying onset of a disease.

As used herein, the term "prevention" of a disorder, or a grammatical derivation thereof, is defined as reducing the risk of onset of a disease, e.g., as a prophylactic therapy for a subject who is at risk of developing a disorder associated with a mutation. A subject can be characterized as "at risk" of developing a disorder by identifying a mutation associated with the disorder, according to any suitable method known in the art or described herein. In some embodiment, a subject who is at risk of developing a disorder has one or more mutations associated with the disorder. Additionally, or alternatively, a subject can be characterized as "at risk" of developing a disorder if the subject has a family history of the disorder.

The term "administering," or a grammatical derivation thereof, as used in the methods described herein, refers to delivering the composition, or an ex vivo-treated cell, to the subject in need thereof, e.g., having a mutation or defect in the targeted gene. For example, in one embodiment in which ocular cells are targeted, the method involves delivering the composition by subretinal injection to the photoreceptor cells or other ocular cells. In another embodiment, intravitreal injection to ocular cells or injection via the palpebral vein to ocular cells may be employed. In another embodiment, the composition is administered intravenously. Still other methods of administration may be selected by one of skill in the art, in view of this disclosure.

The term "pharmaceutically acceptable" means safe for administration to a mammal, such as a human. In some embodiments, a pharmaceutically acceptable composition is approved by a regulatory agency of the Federal or a state government or listed in the U. S. Pharmacopeia or other generally recognized pharmacopeia for use in animals, and more particularly in humans.

The term "carrier" refers to a diluent, adjuvant, excipient, or vehicle with which a vector or composition of the invention is administered. Examples of suitable pharmaceutical carriers are described in "Remington's Pharmaceutical Sciences," Mack Publishing Co., Easton, Pa., $2^{nd}$ edition, 2005.

The terms "a" and "an" mean "one or more of." For example, "a gene" is understood to represent one or more such genes. As such, the terms "a" and "an," "one or more of a (or an)," and "at least one of a (or an)" are used interchangeably herein.

As used herein, the term "about" refers to a value within ±10% variability from the reference value, unless otherwise specified.

For any conflict in definitions between various sources or references, the definition provided herein shall control.

II. Vectors

Provided herein are synthetic DNA vectors featuring a heterologous gene. The DNA vector may further include a double D (DD) element. Synthetic DNA vectors having DD elements can persist intracellularly (e.g., in quiescent cells, such as post-mitotic cells) as episomes, e.g., in a manner similar to AAV vectors. Vectors provided herein can be naked DNA vectors, devoid of components inherent to viral vectors (e.g., viral proteins) and bacterial plasmid DNA, such as immunogenic components (e.g., immunogenic bacterial signatures (e.g., CpG islands or CpG motifs)) or components additionally, or otherwise associated with reduced persistence (e.g., CpG islands or CpG motifs).

Further provided are synthetic circular DNA vectors featuring a heterologous gene without an origin of replication and/or a drug resistance gene, herein referred to as circular DNA vectors. The present invention provides circular DNA vectors that are produced synthetically.

Synthetic circular DNA vectors of the invention can persist intracellularly (e.g., in quiescent cells, such as post-mitotic cells) as episomes, e.g., in a manner similar to AAV vectors. Vectors provided herein can be naked DNA vectors, devoid of components inherent to viral vectors (e.g., viral proteins) and bacterial plasmid DNA, such as immunogenic components (e.g., immunogenic bacterial signatures (e.g., CpG motifs)) or components additionally or otherwise associated with reduced persistence (e.g., CpG islands). For example, in some embodiments, the vector contains DNA in which at least 50% (e.g., at least 60%, at least 70%, at least 80%, at least 90%, at least 95%, at least 97%, at least 99%, or essentially all) of the DNA lacks one or more elements of bacterial plasmid DNA, such as immunogenic components (e.g., immunogenic bacterial signatures (e.g., CpG motifs)) or components additionally or otherwise associated with reduced persistence (e.g., CpG islands). In some embodiments, at least 50% (e.g., at least 60%, at least 70%, at least 80%, at least 90%, at least 95%, at least 97%, at least 99%, or essentially all) of the DNA lacks CpG methylation. In some embodiments, the vector contains DNA in which at least 50% (e.g., at least 60%, at least 70%, at least 80%, at least 90%, at least 95%, at least 97%, at least 99%, or essentially all) of the DNA lacks bacterial methylation signatures, such as Dam methylation and Dcm methylation. For examples, in some embodiments, the vector contains DNA in which at least 50% (e.g., at least 60%, at least 70%, at least 80%, at least 90%, at least 95%, at least 97%, at least 99%, or essentially all) of the GATC sequences are unmethylated (e.g., by Dam methylase). Additionally or alternatively, the vector contains DNA in which at least 50% (e.g., at least 60%, at least 70%, at least 80%, at least 90%, at least 95%, at least 97%, at least 99%, or essentially all) of the CCAGG sequences and/or CCTGG sequences are unmethylated (e.g., by Dcm methylase).

In some embodiments regarding each of the aforementioned vectors, the DNA vector is persistent in vivo (e.g., the circularity and non-bacterial nature (i.e., by in vitro (e.g., cell-free) synthesis) are associated with long-term transcription or expression of a heterologous gene of the DNA vector). In some embodiments, the persistence of the circular DNA vector is from 5% to 50% greater, 50% to 100% greater, one-fold to five-fold, or five-fold to ten-fold (e.g., at least 5%, 10%, 20%, 30%, 40%, 50%, 75%, one-fold, two-fold, three-fold, four-fold, five-fold, six-fold, seven-fold, eight-fold, nine-fold, ten-fold, or more) greater than a reference vector (e.g., a circular vector produced in bacteria or having one or more bacterial signatures not present in the vector of the invention). In some embodiments, the circular DNA vector of the invention persists for one week to four weeks, from one month to four months, from four months to one year, from one year to five years, from five years to twenty years, or from twenty years to fifty years (e.g., at least one week, at least two weeks, at least one month, at least four months, at least one year, at least two years, at least five years, at least ten years, at least twenty years, at least thirty years, at least forty years, or at least fifty years). In some embodiments, the DNA vector includes a DD element, which may be associated with increased persistence.

A DNA vector may be a circular DNA vector. The circular DNA vector may be monomeric, dimeric, trimeric, tetrameric, pentameric, hexameric, etc. Preferably, the circular DNA vector is monomeric. In other preferred embodiments, the circular DNA vector is a monomeric, supercoiled circular DNA molecule. In some embodiments, the DNA vector is nicked. In some embodiments, the DNA vector is open circular. In some embodiments, the DNA vector is double-stranded circular.

Additionally, or alternatively, the DNA vector may include a DD element. In certain embodiments, the DNA vector (e.g., the circular DNA vector, e.g., the monomeric circular DNA vector) includes, operatively linked in the 5' to 3' direction: (i) a 5' D element, (ii) a heterologous gene, and (iii) a 3' D element. In some embodiments, the DNA vector comprises, operatively linked in the 5' to 3' direction: (i) a 5' D element, (ii) a promoter, (iii) a heterologous gene, and (iv) a 3' D element. In some embodiments, the DNA vector comprises, operatively linked in the 5' to 3' direction: (i) a 5' D element, (ii) a promoter, (iii) a heterologous gene, (iv) a polyadenylation site, and (v) a 3' D element.

For example, a DNA vector may include, operatively linked in a 5' to 3' direction: (i) a 5' A element, (ii) 5' D element, (iii) a heterologous gene, (iv) a 3' D element, and (v) a 5' A element. In some embodiments, the DNA vector includes, in a 5' to 3' direction: (i) a 5' A element, (ii) 5' D element, (iii) a promoter, (iv) a heterologous gene, (v) a 3' D element, and (vi) a 5' A element. In some embodiments, the DNA vector includes, in a 5' to 3' direction: (i) a 5' A element, (ii) 5' D element, (iii) a promoter, (iv) a heterologous gene, (v) a polyadenylation site, (vi) a 3' D element, and (vii) a 5' A element. In some embodiments, the DNA vector includes, in a 5' to 3' direction: (i) a 5' C element, (ii) a 5' A element, (iii) 5' D element, (iv) a heterologous gene, (v) a 3' D element, (vi) a 3' A element, and (vii) a 3' B element. In some embodiments, the DNA vector includes, in a 5' to 3' direction: (i) a 5' C element, (ii) a 5' A element, (iii) 5' D element, (iv) a promoter, (v) a heterologous gene, (vi) a 3' D element, (vii) a 3' A element, and (viii) a 3' B element. In some embodiments, the DNA vector includes, in a 5' to 3' direction: (i) a 5' C element, (ii) a 5' A element, (iii) 5' D element, (iv) a promoter, (v) a heterologous gene, (vi) a polyadenylation site, (vii) a 3' D element, (viii) a 3' A element, and (ix) a 3' B element.

In some embodiments, the DNA vector includes a DD element having a nucleic acid sequence having at least a 5' D element and a 3' D element on the same nucleic acid (e.g., DNA) strand. For example, in some embodiments, the DNA vector includes, operatively linked in a 5' to 3' direction: (i) a heterologous gene and (ii) a DD element. In some embodiments, the DNA vector includes, in a 5' to 3' direction: (i) a promoter, (ii) a heterologous gene, and (iii) DD element. In some embodiments, the DNA vector includes, in a 5' to 3' direction: (i) a heterologous gene, (ii) a polyadenylation site, and (iii) a DD element. In some embodiments, the DNA vector includes, in a 5' to 3' direction: (i) a promoter, (ii) a heterologous gene, (iii) a polyadenylation site, and (iv) a DD element.

Terminal Repeat Sequences

In some embodiments of the present invention, vectors and compositions provided herein include terminal repeat sequences, which may be derived, e.g., from ITRs, LTRs, or other terminal structures, e.g., as a result of circularization. The terminal repeat sequence can be at least 10 base pairs (bp) in length (e.g., from 10 bp to 500 bp, from 12 bp to 400 bp, from 14 bp to 300 bp, from 16 bp to 250 bp, from 18 bp to 200 bp, from 20 bp to 180 bp, from 25 bp to 170 bp, from 30 bp to 160 bp, or from 50 bp to 150 bp, e.g., from 10 bp to 15 bp, from 15 bp to 20 bp, from 20 bp to 25 bp, from 25 bp to 30 bp, from 30 bp to 35 bp, from 35 bp to 40 bp, from 40 bp to 45 bp, from 45 bp to 50 bp, from 50 bp to 55 bp, from 55 bp to 60 bp, from 60 bp to 65 bp, from 65 bp to 70 bp, from 70 bp to 80 bp, from 80 bp to 90 bp, from 90 bp to 100 bp, from 100 bp to 150 bp, from 150 bp to 200 bp, from 200 bp to 300 bp, from 300 bp to 400 bp, or from 400 bp to 500 bp, e.g., 10 bp, 11 bp, 12 bp, 13 bp, 14 bp, 15 bp, 16 bp, 17 bp, 18 bp, 19 bp, 20 bp, 21 bp, 22 bp, 23 bp, 24 bp, 25 bp, 26 bp, 27 bp, 28 bp, 29 bp, 30 bp, 31 bp, 32 bp, 33 bp, 34 bp, 35 bp, 36 bp, 37 bp, 38 bp, 39 bp, 40 bp, 41 bp, 42 bp, 43 bp, 44 bp, 45 bp, 46 bp, 47 bp, 48 bp, 49 bp, 50 bp, 51 bp, 52 bp, 53 bp, 54 bp, 55 bp, 56 bp, 57 bp, 58 bp, 59 bp, 60 bp, 61 bp, 62 bp, 63 bp, 64 bp, 65 bp, 66 bp, 67 bp, 68 bp, 69 bp, 70 bp, 71 bp, 72 bp, 73 bp, 74 bp, 75 bp, 76 bp, 77 bp, 78 bp, 79 bp, 80 bp, 81 bp, 82 bp, 83 bp, 84 bp, 85 bp, 86 bp, 87 bp, 88 bp, 89 bp, 90 bp, 91 bp, 92 bp, 93 bp, 94 bp, 95 bp, 96 bp, 97 bp, 98 bp, 99 bp, 100 bp, 101 bp, 102 bp, 103 bp, 104 bp, 105 bp, 106 bp, 107 bp, 108 bp, 109 bp, 110 bp, 111 bp, 112 bp, 113 bp, 114 bp, 115 bp, 116 bp, 117 bp, 118 bp, 119 bp, 120 bp, 121 bp, 122 bp, 123 bp, 124 bp, 125 bp, 126 bp, 127 bp, 128 bp, 129 bp, 130 bp, 131 bp, 132 bp, 133 bp, 134 bp, 135 bp, 136 bp, 137 bp, 138 bp, 139 bp, 140 bp, 141 bp, 142 bp, 143 bp, 144 bp, 145 bp, 146 bp, 147 bp, 148 bp, 149 bp, 150 bp, or more).

In some embodiments of the present invention, a terminal repeat sequence of a synthetic vector can be a DD element (e.g., a DD element derived from, and/or containing one or more portions of an ITR). A DD element contains two D elements on a single DNA molecule. In some embodiments, the two D elements are separated by about 125 nucleic acids. DD elements can be derived from an AAV of any serotype, e.g., AAV1, AAV2, AAV3, AAV4, AAV5, AAV6, AAV7, AAV8, or AAV9.

In some embodiments, the DD element comprises two D elements directly joined to one another, for example, in the configuration shown in FIG. 6F. Thus, in some embodiments, the DD element has the nucleic acid sequence of SEQ ID NO: 14. In some embodiments, the DD element is 80%, 82.5%, 85%, 87.5%, 90%, 92.5%, 95%, 97.5%, or 100% homologous to the nucleic acid sequence of SEQ ID NO: 14.

In other embodiments, a DD element of the present invention has at least one additional element separating the 5' D element from the 3' D element, such as one or more A elements; one or more B elements; and/or one or more C elements, which may be arranged in any suitable order. For example, in some embodiments, the DD element comprises, operatively linked in a 5'-to-3' configuration: (i) a 5' D element (i.e., a nucleic acid sequence having at least 80% homology (e.g., 80%, 85%, 90%, 95%, or 100% homology) to the nucleic acid sequence of any one of SEQ ID NOs: 1, 19, 21, 23, 25, 27, 29, 38, or 40; (ii) one or more internal nucleic acids (e.g., non-heterologous nucleic acids), and (iii) a 3' D element (i.e., a nucleic acid sequence having at least 80% homology (e.g., 80%, 85%, 90%, 95%, or 100% homology) to the nucleic acid sequence of any one of SEQ ID NOs: 8, 20, 22, 24, 26, 28, 30, 39, or 41. In some embodiments, the one or more nucleic acids of (ii) is from 1-125 nucleic acids, 2-100 nucleic acids, 5-80 nucleic acids, or 10-50 nucleic acids, e.g., 1-20 nucleic acids, 20-40 nucleic acids, 40-60 nucleic acids, 60-80 nucleic acids, 80-100 nucleic acids, or 100-125 nucleic acids, e.g., 1-5 nucleic acids, 5-10 nucleic acids, 10-15 nucleic acids, 15-20 nucleic acids, 20-25 nucleic acids, 25-30 nucleic acids, 30-35 nucleic acids, 35-40 nucleic acids, 40-45 nucleic acids, 45-50 nucleic acids, 50-55 nucleic acids, 55-60 nucleic acids, 60-65 nucleic acids, 65-70 nucleic acids, 70-75 nucleic acids, 75-80 nucleic acids, 80-85 nucleic acids, 85-90 nucleic acids, 90-95 nucleic acids, 95-100 nucleic acids, 100-105 nucleic acids, 105-110 nucleic acids, 110-115 nucleic acids, 115-120 nucleic acids, 120-125 nucleic acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, or 125 nucleic acids).

In some embodiments, the DD element comprises two D elements (e.g., a 5' D element (e.g., SEQ ID NO: 1, 19, 21, 23, 25, 27, 29, 38, or 40) and a 3' D element (e.g., SEQ ID NO: 8, 20, 22, 24, 26, 28, 30, 39, or 41)), in addition to two A elements (e.g., a 5' A element (e.g., SEQ ID NO: 2) and a 3' A element (e.g., SEQ ID NO: 7)), two B elements (e.g., a 5' B element (e.g., SEQ ID NO: 5) and a 3' B element (e.g., SEQ ID NO: 6)), and two C elements, e.g., SEQ ID NOs: 1-8. The nucleic acid sequences of SEQ ID NOs: 1-8 may be operatively linked in order in a 5' to 3' direction, for example, as shown in FIG. 6A. Thus, in some embodiments, the DD element comprises the nucleic acid sequence of SEQ ID NO: 9. Alternatively, SEQ ID NOs: 1-8 can be operatively linked in any suitable order. For example, in some embodiments, the DD element comprises the nucleic acid sequence of SEQ ID NO: 10. In particular embodiments, SEQ ID NOs: 1 and 8 (i.e., the two D elements) flank the remaining elements and/or nucleic acids within the D element.

Figure 6B:
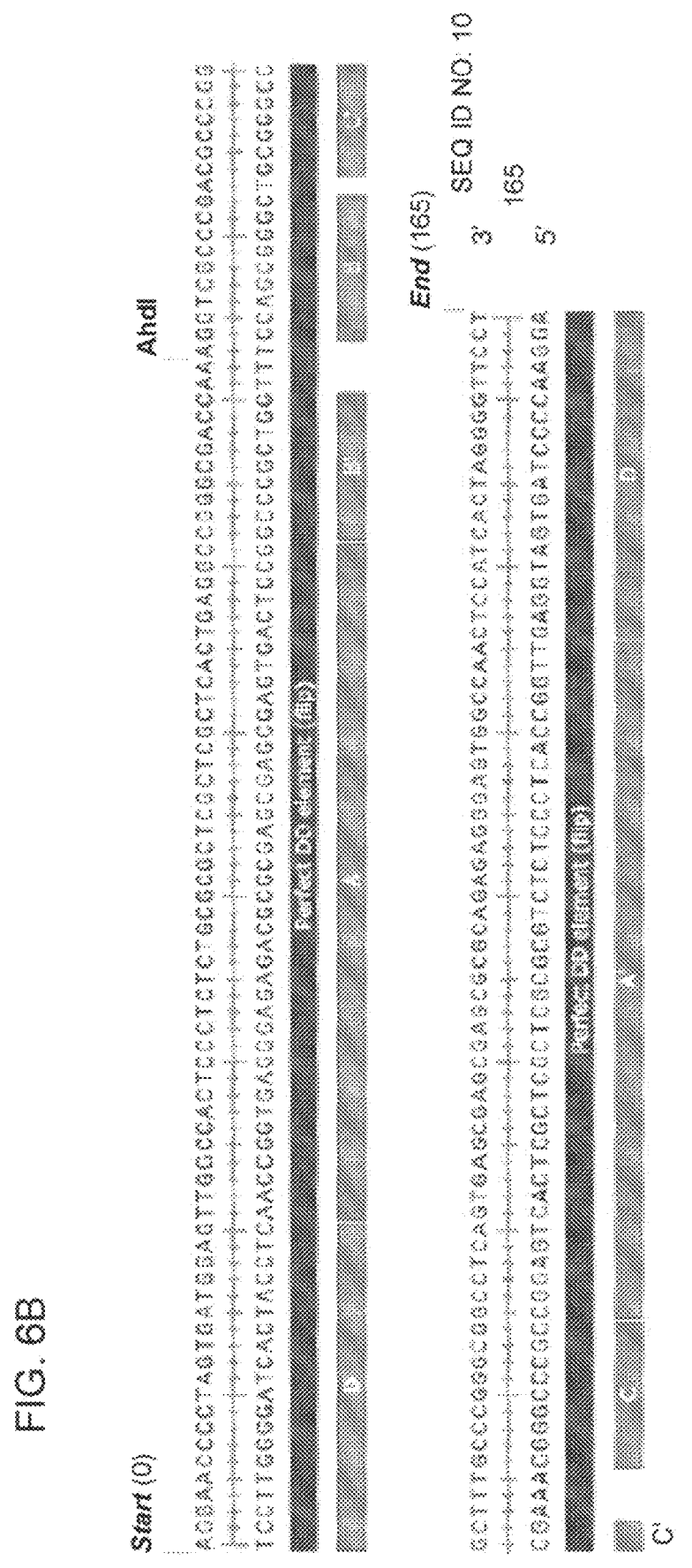

The elements of SEQ ID NOs: 1-8 can each be directly linked or indirectly linked (e.g., operatively linked) to one another, e.g., SEQ ID NOs: 1-8 can be operatively linked in a 5' to 3' direction. Alternatively, there may be one or more nucleic acids separating one or more operatively linked elements, as shown in FIGS. 6A and 6B. In some embodiments, the DD element comprises 1-100 additional nucleic acids (e.g., 3-50 nucleic acids, e.g., 3-10 nucleic acids, e.g., 1, 2, 3, 4, 5, 6, 7, 8, 9, 10, 11, 12, or more additional nucleic acids) positioned between the 5' D element and the 3' D element (e.g., between one, two, three, four, five, or more of the following pairs of elements: a 5' D element and a 5' A element, a 5' D element and a 5' B element, a 5' D element and a 3' B element, a 5' D element and a 5' C element, a 5' D element and a 3' C element, a 5' D element and a 3' A element, a 5' D element and a 3' D element, a 5' A element and a 5' B element, a 5' A element and a 3' B element, a 5' A element and a 5' C element, a 5' A element and a 3' C element, a 5' A element and a 3' A element, a 5' A element and a 3' D element, a 5' B element and a 3' B element, a 5' B element and a 5' C element, a 5' B element and a 3' C element, a 5' B element and a 3' A element, a 5' B element and a 3' D element, a 3' B element and a 5' C element, a 3' B element and a 3' C element, a 3' B element and a 3' A element, a 3' B element and a 3' D element, a 5' C element and a 3' C element, a 5' C element and a 3' A element, a 5' C element and a 3' D element, a 3' C element and a 3' A element, a 3' C element and a 3' D element, or a 3' A element and a 3' D element).

Additional nucleic acids may serve, for example, as restriction sites, as shown by the AhdI sites in FIGS. 6A and 6B.

Figure 6C:
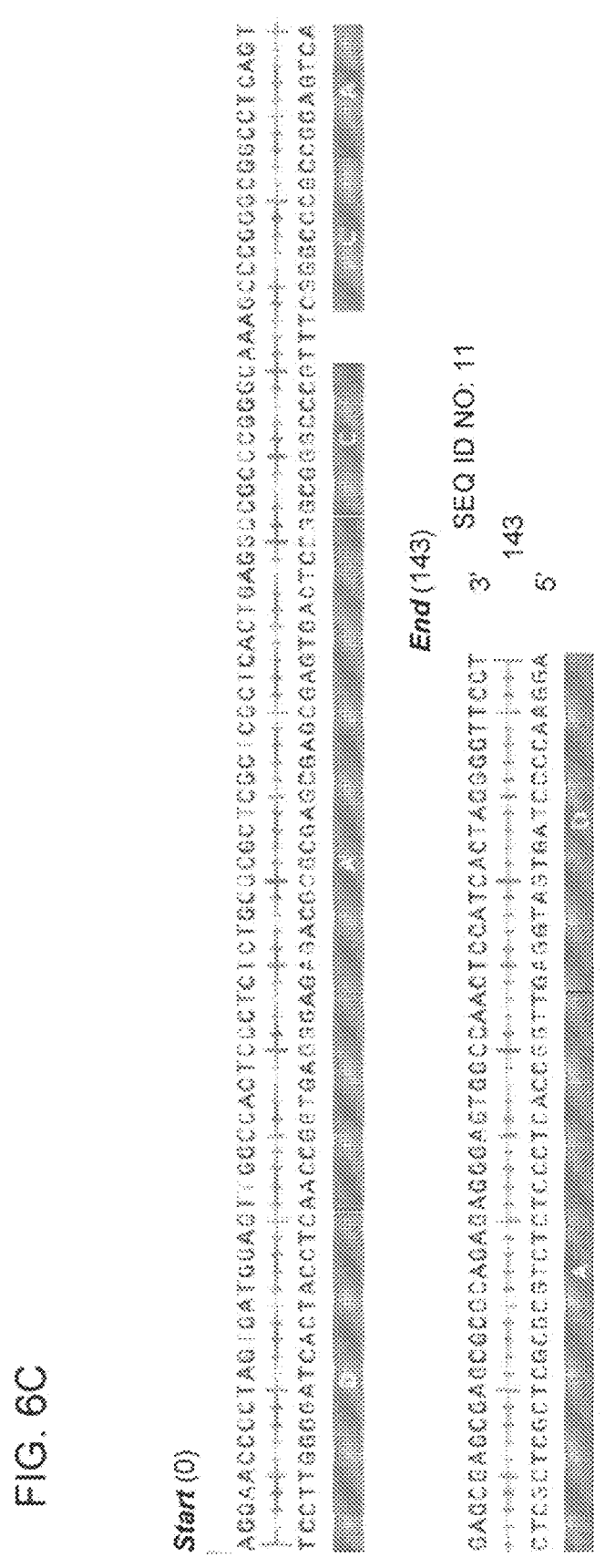
Figure 6D:
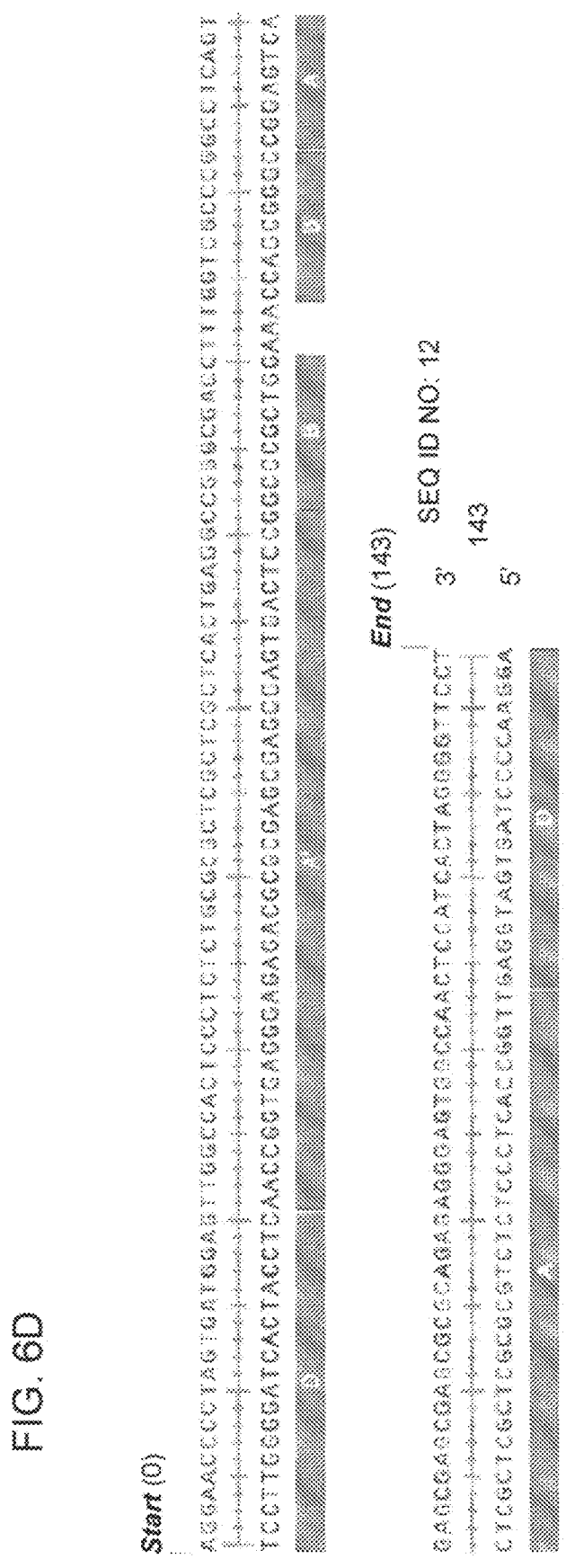

In some embodiments, one or more of elements A, B, or C (e.g., SEQ ID NOs: 2-7) are absent. For example, FIG. 6C shows a AAV2-derived DD element without B elements. Thus, in some embodiments, the DD element of the invention may have a nucleic acid sequence having 80%, 85%, 90%, 95%, 96%, 97%, 98%, 99%, or 100% homology with SEQ ID NO: 11. Similarly, FIG. 6D shows a DD element without C elements. Thus, in some embodiments, the DD element of the invention may have a nucleic acid sequence having 80%, 85%, 90%, 95%, 96%, 97%, 98%, 99%, or 100% homology with SEQ ID NO: 12. In some embodiments, the DD element does not comprise B or C elements, such as shown in FIG. 6E. Thus, in some embodiments, the DD element of the invention may have a nucleic acid sequence having 80%, 85%, 90%, 95%, 96%, 97%, 98%, 99%, or 100% homology with SEQ ID NO: 13.

Alternatively, one or more of elements A, B, or C (e.g., SEQ ID NOs: 2-7) may be replaced by a dissimilar nucleic acid sequence, such as in FIG. 6G, which shows a suitable DD element having a different nucleic acid sequence in place of its 3' A element. Thus, in some embodiments, the DD element comprises SEQ ID NOs: 1-3 and 8. In some embodiments, the DD element of the invention may have a nucleic acid sequence having 80%, 85%, 90%, 95%, 96%, 97%, 98%, 99%, or 100% homology with SEQ ID NO: 15.

In some embodiments, one or more (e.g., one, two, three, four, five, six, or more) nucleic acids overlap between two adjacent elements. For example, in some embodiments wherein the 3'-terminal one or more nucleic acids of a first element match the 5-terminal one or more nucleic acids of a second element linked to its 3' end, the overlapping nucleic acids need not be repeated. An example of such a DD element is shown in FIG. 6H, where the 3' end of the 5' C element overlaps with the 5' end of the 3'A element. Thus, in some embodiments, the DD element of the invention may have a nucleic acid sequence having 80%, 85%, 90%, 95%, 96%, 97%, 98%, 99%, or 100% homology with SEQ ID NO: 16.

Nucleic acid sequences between the 5' and 3' D elements may be portions of any one or more of the 5' or 3'A elements, 5' or 3' B elements, or 5' or 3' C elements. In particular embodiments, the DD element comprises one or more partial A elements, such as shown in FIGS. 6I and 6J. A partial A element may comprise a nucleic acid sequence having six or more consecutive matching nucleic acids as SEQ ID NOs: 2 or 7 (e.g., 6-40, 8-35, 10-30, or 15-25, e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 consecutive matching nucleic acids). In some embodiments, the DD element of the invention may have a nucleic acid sequence having 80%, 85%, 90%, 95%, 96%, 97%, 98%, 99%, or 100% homology with SEQ ID NO: 17. In some embodiments, the DD element of the invention may have a nucleic acid sequence having 80%, 85%, 90%, 95%, 96%, 97%, 98%, 99%, or 100% homology with SEQ ID NO: 18.

Exemplary nucleic acid sequences of AAV2-derived DD elements and sub-elements thereof are provided in Table 2, below.

TABLE 2

Exemplary nucleic acid sequences of DD elements and sub-elements thereof

| SEQ ID NO: | Description | Sequence |
| --- | --- | --- |
| 1 | 5' D element | AGGAACCCCTAGTGATGGAG |
| 2 | 5' A element | TTGGCCACTCCCTCTCTGCGCGCTDGCTCGCTCACTGAGGC |
| 3 | 5' C element | CGCCCGGGC |
| 4 | 3' C element | GCCCGGGCG |
| 5 | 5' B element | CGGGCGACC |
| 6 | 3' B element | GGTCGCCCG |
| 7 | 3' A element | GCCTCAGTGAGCGAGCGAGCGCGCAGAGAGGGAGTGGCCAA |
| 8 | 3' D element | CTCCATCACTAGGGGTTCCT |

TABLE 2-continued

Exemplary nucleic acid sequences of DD elements and sub-elements thereof

| SEQ ID NO: | Description | Sequence |
|---|---|---|
| 9 | Standard DD (flop) | AGGAACCCCTAGTGATGGAGTTGGCCACTCCCTCTCTGCGCGC<br>TCGCTCGCTCACTGAGGCCGCCCGGGCAAAGCCCGGGCGTCG<br>GGCGACCTTTGGTCGCCCGGCCTCAGTGAGCGAGCGAGCGCG<br>CAGAGAGGGAGTGGCCAACTCCATCACTAGGGGTTCCT |
| 10 | Standard DD (flip) | AGGAACCCCTAGTGATGGAGTTGGCCACTCCCTCTCTGCGCGC<br>TCGCTCGCTCACTGAGGCCGGGCGACCAAAGGTCGCCCGACG<br>CCCGGGCTTTGCCCGGGCGGCCTCAGTGAGCGAGCGAGCGC<br>GCAGAGAGGGAGTGGCCAACTCCATCACTAGGGGTTCCT |
| 11 | Deleted BB | AGGAACCCCTAGTGATGGAGTTGGCCACTCCCTCTCTGCGCGC<br>TCGCTCGCTCACTGAGGCCGCCCGGGCAAAGCCCGGGCGGC<br>CTCAGTGAGCGAGCGAGCGCGCAGAGAGGGAGTGGCCAACTC<br>CATCACTAGGGGTTCCT |
| 12 | Deleted CC | AGGAACCCCTAGTGATGGAGTTGGCCACTCCCTCTCTGCGCGC<br>TCGCTCGCTCACTGAGGCCGGGCGACCTTTGGTCGCCCGGCC<br>TCAGTGAGCGAGCGAGCGCGCAGAGAGGGAGTGGCCAACTCC<br>ATCACTAGGGGTTCCT |
| 13 | Deleted BBCC | AGGAACCCCTAGTGATGGAGTTGGCCACTCCCTCTCTGCGCGC<br>TCGCTCGCTCACTGAGGCGCCTCAGTGAGCGAGCGAGCGCGC<br>AGAGAGGGAGTGGCCAACTCCATCACTAGGGGTTCCT |
| 14 | Deleted BBCCAA | AGGAACCCCTAGTGATGGAGCTCCATCACTAGGGGTTCCT |
| 15 | Clone: T88-16 | AGGAACCCCTAGTGATGGAGTTGGCCACTCCCTCTCTGCGCGC<br>TCGCTCGCTCACTGAGGCCGCCCGGGCGAGCGCGCAGAGAG<br>GGAGTGGCCAACTCCATCACTAGGGGTTCCT |
| 16 | Clone: 302A-12 | AGGAACCCCTAGTGATGGAGTTGGCCACTCCCTCTCTGCGCGC<br>TCGCTCGCTCACTGAGGCCGCCCGGGCCTCAGTGAGCGAGCG<br>AGCGCGCAGAGAGGGAGTGGCCAACTCCATCACTAGGGGTTC<br>CT |
| 17 | Clone: 304B-68 | AGGAACCCCTAGTGATGGAGTTGGCCACTCCCTCGCAGAGAG<br>GGAGTGGCCAACTCCATCACTAGGGGTTCCT |
| 18 | Clone: 307A-9 | AGGAACCCCTAGTGATGGAGTTGGCCACTCCCTCTCTGCGCGC<br>TCGCTCGCTCACTGAGGCCGAGCGCGCAGAGAGGGAGTGGCC<br>AACTCCATCACTAGGGGTTCCT |

Heterologous Genes

Any of the vectors of the present invention (e.g., DNA vectors containing a DD element, having a circular structure, or both) can be used to insert a heterologous gene into a target cell. As disclosed herein, a broad range of heterologous genes may be delivered to target cells by way of the present vectors. In some embodiments, the heterologous gene is configured to transfect a target cell having a mutation associated with a disease which can be treated by expression of the heterologous gene, e.g., a gene encoding a therapeutic protein, e.g., a protein that is defective or absent in the target cell and/or subject.

In such instances, the heterologous gene may encode all or a portion of (e.g., as part of a trans-splicing molecule) an ocular protein, such as CEP290, ABCA4, ABCC6, RIMS1, LRP5, CC2D2A, TRPM1, C3, IFT172, COL11A1, TUBGCP6, KIAA1549, CACNA1F, SNRNP200, RP 1, MYO7A, PRPF8, VCAN, USH2A, and HMCN1. Other exemplary therapeutic proteins include one or more polypeptides selected from the group consisting of growth factors, interleukins, interferons, anti-apoptosis factors, cytokines, anti-diabetic factors, anti-apoptosis agents, coagulation factors, anti-tumor factors, liver-secreted proteins, neuroprotective factors, or neurotrophins. Therapeutic proteins may include BDNF, CNTF, CSF, EGF, FGF, G-SCF, GM-CSF, gonadotropin, IFN, IFN-α, IFN-γ IFG-1, M-CSF, NGF, PDGF, PEDF, TGF, VEGF, TGF-B2, TNF, prolactin, somatotropin, XIAP1, I-1, IL-2, IL-3, IL-4, IL-5, IL-6, IL-7, IL-8, IL-9, IL-10, IL-10, viral IL-10, IL-11, IL-12, IL-13, IL-14, IL-15, IL-16, IL-17, and/or IL-18.

The heterologous gene may encode all or a portion of a neuroprotective factor, such as Kifap3, Bcl-xl, Crmp1, Chk-.beta., CALM2, Caly, NPG11, NPT1, Eef1a1, Dhps, Cd151, Morf412, CTGF, LDH-A, Atl1, NPT2, Ehd3, Cox5b, Tuba1a, gamma-actin, Rpsa, NPG3, NPG4, NPG5, NPG6, NPG7, NPG8, NPG9, and NPG10. Exemplary neurotrophins are NGF, BDNF, NT-3, NT-4, and CNTF.

In some instances, the heterologous gene is associated with a disorder selected from the group consisting of an ocular disorder, a liver disorder, a neurological disorder, an immune disorder, a cancer, a cardiovascular disorder, a blood coagulation disorder, a lysosomal storage disorder, or type 2 diabetes.

Heterologous genes for treatment of blood coagulation disorders include genes that correct a defect in a coagulation factor or set of coagulation factors, such as one or more coagulation factors selected from the group consisting of fibrinogen, prothrombin, thromboplastin, factor V, factor VII (e.g., factor VIIa), factor VIII, factor IX, factor X, factor XI, factor XII, factor XIII, or von Willebrand factor. In some instances, the heterologous gene encodes for fibrinogen, prothrombin, thromboplastin, factor V, factor VII, factor VIII, factor IX, factor X, factor XI, factor XII, factor XIII, or von Willebrand factor. For example, in some instances, a heterologous gene encoding for fibrinogen is FGA, FGB, or FGG; a heterologous gene encoding for prothrombin is F2; a heterologous gene encoding for factor V is F5; a heterologous gene encoding for factor VII is F7; a heterologous gene encoding for factor VIII is F8; a heterologous gene encoding for factor IX is F9; a heterologous gene encoding for factor X is F10; a heterologous gene encoding for factor XII is F11; a heterologous gene encoding for factor XII is F12; a heterologous gene encoding for factor XIII is F13A or F13B. In some instances, the heterologous gene is LMAN1 or MCFD2. Alternatively, the heterologous gene may encode for an enzyme involved in the posttranslational modifications of any of the preceding coagulation factors.

Other heterologous genes encoding polypeptides of interest can be included as part of the vectors of the invention, including for example, growth hormones to promote growth in a transgenic animal, or insulin-like growth factors (IGFs), α-anti-trypsin, erythropoietin (EPO), factors VIII, IX, X, and XI of the blood clotting system, LDL-receptor, GATA-1, etc. The nucleic acid sequence may include a suicide gene encoding, e.g., apoptotic or apoptosis-related enzymes and genes including AIF, Apaf, (e.g., Apaf-1, Apaf-2, or Apaf-3) APO-2 (L), APO-3 (L), Apopain, Bad, Bak, Bax, Bcl-2, Bcl-x.sub.L, Bcl-x.sub.S, bik, CAD, Calpain, Caspases e.g. Caspase-1, Caspase-2, Caspase-3, Caspase-4, Caspase-5, Caspase-6, Caspase-7, Caspase-8, Caspase-9, Caspase-10, Caspase-11, or Granzyme B, ced-3, ced-9, Ceramide, c-Jun, c-Myc, CPP32, crm A, Cytochrome c, D4-GDP-DI, Daxx, CdR1, DcR1, DD, DED, DISC, DNA-PK.sub.CS, DR3, DR4, DR5, FADD/MORT-1, FAK, Fas, Fas-ligand CD95/fas (receptor), FLICE/MACH, FLIP, Fodrin, fos, G-Actin, Gas-2, Gelsolin, glucocorticoid/glucocorticoid receptor, granzyme A/B, hnRNPs C1/C2, ICAD, ICE, JNK, Lamin A/B, MAP, MCL-1, Mdm-2, MEKK-1, MORT-1, NEDD, NF-κB, NuMa, p53, PAK-2, PARP, Perforin, PITSLRE, PKC-delta, pRb, Presenilin, prICE, RAIDD, Ras, RIP, Sphingomyelinase, SREBPs, thymidine kinase from Herpes simplex, TNF-α, TNF-α receptor, TRADD, TRAF2, TRAIL-R1, TRAIL-R2, TRAIL-R3, Transglutaminase, U1 70 kDa snRNP, YAMA, etc.

In some embodiments, the heterologous gene encodes an antibody, or a portion, fragment, or variant thereof. Antibodies include fragments that are capable of binding to an antigen, such as Fv, single-chain Fv (scFv), Fab, Fab', di-scFv, sdAb (single domain antibody) and (Fab')$_2$ (including a chemically linked F(ab')$_2$). Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen. Antibodies also include chimeric antibodies and humanized antibodies. Furthermore, for all antibody constructs provided herein, variants having the sequences from other organisms are also contemplated. Thus, if a human version of an antibody is disclosed, one of skill in the art will appreciate how to transform the human sequence based antibody into a mouse, rat, cat, dog, horse, etc. sequence. Antibody fragments also include either orientation of single chain scFvs, tandem di-scFv, diabodies, tandem tri-sdcFv, minibodies, etc. In some embodiments, such as when an antibody is an scFv, a single polynucleotide of a heterologous gene encodes a single polypeptide comprising both a heavy chain and a light chain linked together. Antibody fragments also include nanobodies (e.g., sdAb, an antibody having a single, monomeric domain, such as a pair of variable domains of heavy chains, without a light chain). Multispecific antibodies (e.g., bispecific antibodies, trispecific antibodies, etc.) are known in the art and contemplated as expression products of the heterologous genes of the present invention.

In some embodiments, the heterologous gene encodes all or a portion of a tumor suppressor gene (e.g., a gene encoding intracellular proteins that control progression into a specific stage of the cell cycle (for e.g., RB1); a gene encoding a receptor or signal transducer for a secreted hormone or developmental signal that inhibits cell proliferation (e.g., adenomatous polyposis coli (APC)); a gene encoding a checkpoint-control protein that trigger cell cycle arrest in response to DNA damage or chromosomal defects (e.g., breast cancer type 1 susceptibility protein (BRCA1), p16 (INK4), or p14 (ARF)); a gene encoding a protein that induces apoptosis (for e.g., PUMA, NOXA, and BIM); or a gene encoding a protein involved in repairing mistakes in DNA (for e.g., DNA mismatch repair protein 2 (MSH2)).

In some embodiments, the heterologous gene encodes all or a portion of a loss of function of a transcription factor (e.g., a master regulator, e.g., a master regulator associate with a disease). In some embodiments, the heterologous gene is TSHZ2, HOXA2, MEIS2, HOXA3, HAND2, HOXA5, TBX18, PEG3, GLI2, CLOCK, HNF4A, VHL/HIF, WT-1, GSK-3, SPINT2, SMAD2, SMAD3, or SMAD4. In some embodiments, the heterologous gene encodes all or a portion of an epigenetic regulator. In some embodiments, the epigenetic regulator is a histone methyltransferase, such as SETDB1, PRMT5, etc. In some embodiments, the epigenetic regulator is a histone demethylase, such as a histone lysine demethylase (KDM), etc. In some embodiments, the epigenetic regulator is a histone acetylase (HDAC). In some embodiments, the epigenetic regulator is a DNA methyltransferase (DNMT). In some embodiments, the epigenetic regulator is a DNA demethylase (e.g., TET1-3).

In some embodiments, the heterologous gene includes a reporter sequence, which can be useful in verifying heterologous gene expression, for example, in specific cells and tissues. Reporter sequences that may be provided in a transgene include, without limitation, DNA sequences encoding β-lactamase, β-galactosidase (LacZ), alkaline phosphatase, thymidine kinase, green fluorescent protein (GFP), chloramphenicol acetyltransferase (CAT), luciferase, and others well known in the art. When associated with regulatory elements which drive their expression, the reporter sequences provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA), and immunohistochemistry. For example, where the marker sequence is the LacZ gene, the presence of the vector carrying the signal is detected by assays for β-galactosidase activity. Where the transgene is green fluorescent protein or luciferase, the vector carrying the signal may be measured visually by color or light production in a luminometer.

In some embodiments, the heterologous gene does not include a coding sequence. Non-coding sequences such as shRNA, promoters, enhancers, sequences to mark DNA (e.g., for antibody recognition), PCR amplification sites, sequences that define restriction enzyme sites, site-specific recombinase recognition sites, sequences that are recognized by a protein that binds to and/or modifies nucleic acids, and linkers, may be included in the vector. In instances in which a heterologous gene is a trans-splicing molecule, non-coding sequences include binding domains that bind a target intron. In some embodiments, the heterologous gene includes a binding domain (e.g., a binding domain, e.g., a pre-mRNA binding portion of a trans-splicing molecule).

In some embodiments, the heterologous gene is from 0.1 Kb to 100 Kb in length (e.g., the heterologous gene is from 0.2 Kb to 90 Kb, from 0.5 Kb to 80 Kb, from 1.0 Kb to 70 Kb, from 1.5 Kb to 60 Kb, from 2.0 Kb to 50 Kb, from 2.5 Kb to 45 Kb, from 3.0 Kb to 40 Kb, from 3.5 Kb to 35 Kb, from 4.0 Kb to 30 Kb, from 4.5 Kb to 25 Kb, from 4.6 Kb to 24 Kb, from 4.7 Kb to 23 Kb, from 4.8 Kb to 22 Kb, from 4.9 Kb to 21 Kb, from 5.0 Kb to 20 Kb, from 5.5 Kb to 18 Kb, from 6.0 Kb to 17 Kb, from 6.5 Kb to 16 Kb, from 7.0 Kb to 15 Kb, from 7.5 Kb to 14 Kb, from 8.0 Kb to 13 Kb, from 8.5 Kb to 12.5 Kb, from 9.0 Kb to 12.0 Kb, from 9.5 Kb to 11.5 Kb, or from 10.0 Kb to 11.0 Kb in length, e.g., from 0.1 Kb to 0.5 Kb, from 0.5 Kb to 1.0 Kb, from 1.0 Kb to 2.5 Kb, from 2.5 Kb to 4.5 Kb, from 4.5 Kb to 8 Kb, from 8 Kb to 10 Kb, from 10 Kb to 15 Kb, from 15 Kb to 20 Kb in length, or greater, e.g., from 0.1 Kb to 0.25 Kb, from 0.25 Kb to 0.5 Kb, from 0.5 Kb to 1.0 Kb, from 1.0 Kb to 1.5 Kb, from 1.5 Kb to 2.0 Kb, from 2.0 Kb to 2.5 Kb, from 2.5 Kb to 3.0 Kb, from 3.0 Kb to 3.5 Kb, from 3.5 Kb to 4.0 Kb, from 4.0 Kb to 4.5 Kb, from 4.5 Kb to 5.0 Kb, from 5.0 Kb to 5.5 Kb, from 5.5 Kb to 6.0 Kb, from 6.0 Kb to 6.5 Kb, from 6.5 Kb to 7.0 Kb, from 7.0 Kb to 7.5 Kb, from 7.5 Kb to 8.0 Kb, from 8.0 Kb to 8.5 Kb, from 8.5 Kb to 9.0 Kb, from 9.0 Kb to 9.5 Kb, from 9.5 Kb to 10 Kb, from 10 Kb to 10.5 Kb, from 10.5 Kb to 11 Kb, from 11 Kb to 11.5 Kb, from 11.5 Kb to 12 Kb, from 12 Kb to 12.5 Kb, from 12.5 Kb to 13 Kb, from 13 Kb to 13.5 Kb, from 13.5 Kb to 14 Kb, from 14 Kb to 14.5 Kb, from 14.5 Kb to 15 Kb, from 15 Kb to 15.5 Kb, from 15.5 Kb to 16 Kb, from 16 Kb to 16.5 Kb, from 16.5 Kb to 17 Kb, from 17 Kb to 17.5 Kb, from 17.5 Kb to 18 Kb, from 18 Kb to 18.5 Kb, from 18.5 Kb to 19 Kb, from 19 Kb to 19.5 Kb, from 19.5 Kb to 20 Kb, from 20 Kb to 21 Kb, from 21 Kb to 22 Kb, from 22 Kb to 23 Kb, from 23 Kb to 24 Kb, from 24 Kb to 25 Kb in length, or greater, e.g., about 4.5 Kb, about 5.0 Kb, about 5.5 Kb, about 6.0 Kb, about 6.5 Kb, about 7.0 Kb, about 7.5 Kb, about 8.0 Kb, about 8.5 Kb, about 9.0 Kb, about 9.5 Kb, about 10 Kb, about 11 Kb, about 12 Kb, about 13 Kb, about 14 Kb, about 15 Kb, about 16 Kb, about 17 Kb, about 18 Kb, about 19 Kb, about 20 Kb in length, or greater).

In some embodiments, the heterologous gene is at least 1,100 bp in length (e.g., from 1,100 bp to 10,000 bp, from 1,100 bp to 8,000 bp, or from 1,100 bp to 5,000 bp in length).

In some embodiments, the heterologous gene is at least 2,500 bp in length (e.g., from 2,500 bp to 10,000 bp, from 2,500 bp to 8,000 bp, or from 2,500 bp to 5,000 bp in length). For example, in particular embodiments, the heterologous gene is sufficiently large to encode a protein and is not an oligonucleotide therapy (e.g., not an antisense, siRNA, shRNA therapy etc.).

Control Elements

In addition to the terminal repeat sequence (e.g., a DD element) and the heterologous gene, DNA vectors of the invention (e.g., circular DNA vectors as described herein) may include conventional control elements necessary which are operably linked to the heterologous gene in a manner which permits transcription, translation, and/or expression in a target cell.

Expression control sequences include appropriate transcription initiation, termination, promoter, and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and sequences that enhance secretion of the encoded product. Various expression control sequences, including promoters which are native, constitutive, inducible, and/or tissue-specific, are known in the art and may be utilized as part of the present invention. A promoter region is operably linked to a heterologous gene if the promoter region is capable of effecting transcription of that gene such that the resulting transcript might be translated into the desired protein or polypeptide. Promoters useful as part of the DNA vectors described herein include constitutive and inducible promoters. Examples of constitutive promoters include, a cytomegalovirus (CMV) promoter (optionally with the CMV enhancer), a retroviral Rous sarcoma virus (RSV) LTR promoter (optionally with the RSV enhancer), an SV40 promoter, a dihydrofolate reductase promoter, a β-actin promoter, a phosphoglycerol kinase (PGK) promoter, and an EF1 a promoter.

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources. Many other systems have been described and can be readily selected by one of skill in the art. Examples of inducible promoters regulated by exogenously supplied promoters include zinc-inducible sheep metallothionine (MT) promoters, dexamethasone-inducible mouse mammary tumor virus promoters, T7 polymerase promoter systems, ecdysone insect promoters, tetracycline-repressible systems, tetracycline-inducible systems, RU486-inducible systems, and rapamycin-inducible systems. Still other types of inducible promoters which may be useful in this context are those which are regulated by a specific physiological state, e.g., temperature, acute phase, a particular differentiation state of the cell, or in replicating cells only.

In another embodiment, the native promoter for the heterologous gene is used. The native promoter may be preferred when it is desired that expression of the heterologous gene should mimic the native expression. The native promoter may be used when expression of the heterologous gene must be regulated temporally or developmentally, or in a tissue-specific manner, or in response to specific transcriptional stimuli. In a further embodiment, other native expression control elements, such as enhancer elements, polyadenylation sites, or Kozak consensus sequences may also be used to mimic native expression.

For heterologous genes encoding proteins, a polyadenylation (pA) sequence can be inserted following the heterologous gene and before the terminal repeat sequence. A heterologous gene useful in the present disclosure may also contain an intron, desirably located between the promoter/enhancer sequence and the heterologous gene. Selection of introns and other common vector elements are conventional and many such sequences are available.

The precise nature of the regulatory sequences needed for gene expression in host cells may vary between species, tissues or cell types, but shall in general include, as necessary, 5' non-transcribed and 5' non-translated sequences involved with the initiation of transcription and translation respectively, such as a TATA box, capping sequence, CAAT sequence, enhancer elements, and the like. Especially, such 5' non-transcribed regulatory sequences will include a promoter region that includes a promoter sequence for transcriptional control of the operably joined gene. Regulatory sequences may also include enhancer sequences or upstream activator sequences as desired. The vectors of the disclosure may optionally include 5' leader or signal sequences.

III. Methods of Production

Provided herein are methods of producing a synthetic DNA vector (e.g., a circular DNA vector as described herein and/or a DNA vector having a DD element). In particular, the methods provided herein involve in vitro synthesis (e.g., in the absence of cells (i.e., cell-free)) rather by bacterial cell synthesis, which provides a purer composition of resulting DNA vector relative to bacterial-derived vector and enables a faster, more efficient synthesis.

Cell-free synthesis of DNA vectors (e.g., circular DNA vectors as described herein and/or DNA vectors containing a DD element) relies on effective replication using a polymerase, such as a phage polymerase (e.g., Phi29 polymerase). In some embodiments, Phi29 polymerase is particular useful to process replication of terminal repeat sequences, such as DD elements. The polymerase used herein can be a thermophilic polymerase that has high processivity through GC-rich residues. In some embodiments, the polymerase used to replicate (e.g., amplify) the DD element is Phi29 polymerase. Particular methods of producing the DNA vectors of the invention are described in detail in the Examples, below.

In general, production of a DNA vector (e.g., a circular DNA vector as described herein) of the invention can begin with providing a sample having a circular DNA molecule including an AAV genome (e.g., a rAAV genome) having heterologous gene and a terminal repeat sequence (e.g., a DD element). For example, the sample can be a lysate or other preparation from a cell (e.g., a mammalian cell) that was infected with the AAV vector (e.g., rAAV vector). Double stranded circular DNA can be obtained from the cell using standard DNA extraction/isolation techniques. In some embodiments, linear DNA is specifically degraded, e.g., using plasmid-safe DNase, to purify the circular DNA.

Next, the double stranded circular DNA having the AAV genome can be amplified in vitro, in a cell-free preparation, by incubating the DNA with a polymerase (e.g., a phage polymerase, e.g., Phi29 DNA polymerase; TempliPhi kit, GE Healthcare), primers (e.g., random primers, e.g., random hexamer primers), and a nucleotide mixture (e.g., dNTP, e.g., dATP, dCTP, dGTP, and dTTP). In some embodiments, the nucleotide mixture is a natural nucleotide mixture (i.e., substantially devoid of nucleotide analogues). The polymerase (e.g., phage polymerase, e.g., Phi29 polymerase) amplifies the AAV genome (e.g., an AAV genome including an intact terminal repeat sequence, e.g., a DD element)) by rolling-circle amplification (e.g., isothermal rolling-circle amplification), generating a linear concatamer having a plurality of AAV genome copies. Suitable polymerases include thermophilic polymerases and polymerases that feature high processivity through GC-rich residues.

The resulting concatamers can be digested using a restriction enzyme to cut once within the genome to generate unit-length linear AAV genomes including the heterologous gene and the terminal repeat sequence (e.g., a DD element)). Self-ligation of this linear DNA molecule (e.g., by the addition of a DNA ligase) results in a circular, synthetic DNA vector of the invention, complete with the heterologous gene and, optionally, the intact terminal repeat sequence (e.g., a DD element). Alternatively, prior to self-ligation, the linear DNA molecule can be cloned into a plasmid vector according to known techniques and characterized, as is illustrated in the Examples below, prior to self-ligation to form the final DNA vector (e.g., a circular vector as described herein and/or a DD-containing DNA vector).

Because the replication and amplification of the genome is feasible using a polymerase in cell-free conditions, the synthetic DNA vector can be isolated from the bacterial components of a plasmid in which it was cloned, and bacterial signatures, such as bacterial CpG motifs and/or dam or dcm methylation, are absent from the isolated vector.

IV. Pharmaceutical Compositions

Provided herein are pharmaceutical compositions including any of the DNA vectors (e.g., synthetic DNA vectors) described herein (e.g., DNA vectors containing a DD element and/or circular DNA vectors described above) in a pharmaceutically acceptable carrier. The pharmaceutical compositions described herein are substantially devoid of contaminates, such viral particles, viral capsid proteins, or peptide fragments thereof. In some embodiments, the pharmaceutical compositions provided herein are non-immunogenic. For example, non-immunogenic pharmaceutical compositions may be substantially devoid of pathogen-associated molecular patterns recognizable by cells of the innate immune system. Such pathogen-associated molecular patterns include CpG motifs (e.g., unmethylated CpG motifs or hypomethylated CpG motifs), endotoxins (e.g., lipopolysaccharides (LPS), e.g., bacterial LPS), flagellin, lipoteichoic acid, peptidoglycan, and viral nucleic acids molecules, such as double-stranded RNA.

The pharmaceutical compositions described herein may be assessed for contamination by conventional methods and formulated into a pharmaceutical composition intended for a suitable route of administration. Still other compositions containing the DNA vector may be formulated similarly with a suitable carrier. Such formulation involves the use of a pharmaceutically and/or physiologically acceptable vehicle or carrier, particularly directed for administration to the target cell. In one embodiment, carriers suitable for administration to the target cells include buffered saline, an isotonic sodium chloride solution, or other buffers, e.g., HEPES, to maintain pH at appropriate physiological levels, and, optionally, other medicinal agents, pharmaceutical agents, stabilizing agents, buffers, carriers, adjuvants, or diluents.

In some embodiments, the carrier is a liquid for injection. Exemplary physiologically acceptable carriers include sterile, pyrogen-free water and sterile, pyrogen-free, phosphate buffered saline. A variety of such known carriers are provided in U.S. Pat. No. 7,629,322, incorporated herein by reference. In one embodiment, the carrier is an isotonic sodium chloride solution. In another embodiment, the carrier is balanced salt solution. In one embodiment, the carrier includes tween. If the vector is to be stored long-term, it may be frozen in the presence of glycerol or Tween20.

In other embodiments, compositions containing vectors described herein include a surfactant. Useful surfactants, such as Pluronic F68 (Poloxamer 188, also known as LUTROL® F68) may be included as they prevent AAV from sticking to inert surfaces and thus ensure delivery of the desired dose. The carrier is isotonic sodium chloride solution and includes a surfactant Pluronic F68.

Delivery vehicles such as liposomes, nanoparticles, microparticles, microspheres, lipid particles, vesicles, and the like, may be used for the introduction of the compositions of the present disclosure into suitable host cells. In particular, the DNA vectors may be formulated for delivery by encapsulation in a lipid particle, a liposome, a vesicle, or a nanoparticle. In some embodiments, the DNA vector is complexed with a delivery vehicle such as a poloxamer and/or polycationic material.

Pharmaceutical compositions having any of the DNA vectors of the invention (e.g., circular DNA vectors as described herein and/or DNA vectors including a DD element) may contain a unit dose containing a quantity of DNA from 10 µg to 10 mg (e.g., from 25 µg to 5.0 mg, from 50 µg to 2.0 mg, or from 100 µg to 1.0 mg of DNA, e.g., from 10 µg to 20 µg, from 20 µg to 30 µg, from 30 µg to 40 µg, from 40 µg to 50 µg, from 50 µg to 75 µg, from 75 µg to 100 µg, from 100 µg to 200 µg, from 200 µg to 300 µg, from 300 µg to 400 µg, from 400 µg to 500 µg, from 500 µg to 1.0 mg, from 1.0 mg to 5.0 mg, or from 5.0 mg to 10 mg of DNA, e.g., about 10 µg, about 20 µg, about 30 µg, about 40 µg, about 50 µg, about 60 µg, about 70 µg, about 80 µg, about 90 µg, about 100 µg, about 150 µg, about 200 µg, about 250 µg, about 300 µg, about 350 µg, about 400 µg, about 450 µg, about 500 µg, about 600 µg, about 700 µg, about 750 µg, about 1.0 mg, about 2.0 mg, about 2.5 mg, about 5.0 mg, about 7.5 mg, or about 10 mg of DNA).

In some embodiments, pharmaceutical compositions contain at least about 0.01% DNA vector by weight. For example, the pharmaceutical compositions may contain 0.01% to 80% DNA vector by weight (e.g., from 0.05% to 50% by weight, 0.1% to 10% by weight, 0.5% to 5% by weight, or 1% to 2.5% by weight of DNA vector, e.g., 0.01% to 0.05% by weight, 0.05% to 0.1% by weight, 0.1% to 0.5% by weight, 0.5% to 1.0% by weight, 1.0% to 2% by weight, 2% to 3% by weight, 3% to 5% by weight, 5% to 10% by weight, 10% to 20% by weight, or 20% to 50% by weight of DNA vector).

Pharmaceutical compositions of the invention can contain any of the synthetic circular DNA vectors described herein in monomeric form (e.g., greater than 50% monomeric, greater than 60% monomeric, greater than 70% monomeric, greater than 80% monomeric, greater than 90% monomeric, greater than 95% monomeric, greater than 97% monomeric, greater than 98% monomeric, or greater than 99% monomeric). In some embodiments, from 70% to 99.99% of the synthetic circular DNA vector molecules in the pharmaceutical composition are monomeric (e.g., from 70% to 99.9%, from 70% to 99.5%, from 70% to 99%, from 75% to 99.9%, from 75% to 99.5%, from 75% to 99%, from 80% to 99.9%, from 80% to 99.5%, from 80% to 99%, from 85% to 99.9%, from 85% to 99.5%, from 85% to 99%, from 90% to 99.9%, from 90% to 99.5%, from 90% to 99%, from 95% to 99.9%, from 95% to 99.5%, or from 95% to 99% of the synthetic circular DNA vector molecules in the pharmaceutical composition are monomeric, e.g., about 70%, 75%, 80%, 85%, 90%, 91%, 92%, 93%, 94%, 95%, 96%, 97%, 98%, 99%, 99.5%, or 99.9% of the synthetic circular DNA vector molecules in the pharmaceutical composition are monomeric).

V. Methods of Use

Provided herein are methods of inducing expression (e.g., episomal expression) of a heterologous gene in a subject in need thereof (e.g., as part of a gene therapy regimen) by administering to the subject any of the DNA vectors (e.g., circular DNA vectors as described herein and/or DNA vectors including a DD element) or pharmaceutical compositions thereof described herein. Cells of a subject that contain a heterologous gene can be characterized by examining the nucleic acid sequence (e.g., an RNA sequence, e.g., an mRNA sequence) of the host cell, such as by Southern Blotting or PCR analysis, to assay for the presence of the heterologous gene contained in the vector. Alternatively, the expression of the heterologous gene in the subject can be characterized (e.g., quantitatively or qualitatively) by monitoring the progress of a disease associated with a defect or mutation in the target gene corresponding to the heterologous gene. In some embodiments, the expression (e.g., episomal expression) of the heterologous gene is confirmed by observing a decline in one or more symptoms associated with the disease.

Accordingly, the invention provides methods of treating a disease in a subject associated with a defect in a target gene (e.g., a gene corresponding to the heterologous gene) by administering to the subject any of the DNA vectors (e.g., circular DNA vectors as described herein and/or DNA vectors including a DD element) or pharmaceutical compositions thereof described herein. In some embodiments, the disease is an ocular disease. In some embodiments, the subject is being treated for Leber's congenital amaurosis (LCA, e.g., LCA 10) using a DNA vector having a heterologous CEP290 gene or portion thereof (e.g., as part of a trans-splicing molecule). In some embodiments, the subject is being treated for Stargardt Disease using a DNA vector having a heterologous ABCA4 gene or portion thereof (e.g., as part of a trans-splicing molecule). In some embodiments, the subject is being treated for pseudoxanthoma elasticum using a DNA vector having a heterologous ABCC6 gene or portion thereof (e.g., as part of a trans-splicing molecule). In some embodiments, the subject is being treated for rod cone dystrophy (e.g., rod cone dystrophy 7) using a DNA vector having a heterologous RIMS1 gene or portion thereof (e.g., as part of a trans-splicing molecule). In some embodiments, the subject is being treated for exudative vitreoretinopathy using a DNA vector having a heterologous LRP5 gene or portion thereof (e.g., as part of a trans-splicing molecule). In some embodiments, the subject is being treated for Joubert Syndrome using a DNA vector having a heterologous CC2D2A gene or portion thereof (e.g., as part of a trans-splicing molecule). In some embodiments, the subject is being treated for CSNB-1C using a DNA vector having a heterologous TRPM1 gene or portion thereof (e.g., as part of a trans-splicing molecule). In some embodiments, the subject is being treated for age-related macular degeneration using a DNA vector having a heterologous C3 gene or portion thereof (e.g., as part of a trans-splicing molecule). In some embodiments, the subject is being treated for retinitis pigmentosa 71 using a DNA vector having a heterologous IFT172 gene or portion thereof (e.g., as part of a trans-splicing molecule). In some embodiments, the subject is being treated for stickler syndrome (e.g., stickler syndrome 2) using a DNA vector having a heterologous COL11A1 gene or portion thereof (e.g., as part of a trans-splicing molecule). In some embodiments, the subject is being treated for microcephaly and chorioretinopathy using a DNA vector having a heterologous TUBGCP6 gene or portion thereof (e.g., as part of a trans-splicing molecule). In some embodiments, the subject is being treated for retinitis pigmentosa (e.g., RP recessive) using a DNA vector having a heterologous KIAA1549 gene or portion thereof (e.g., as part of a trans-splicing molecule). In some embodiments, the subject is being treated for CSNB 2 using a DNA vector having a heterologous CACNA1F gene or portion thereof (e.g., as part of a trans-splicing molecule). In some embodiments, the subject is being treated for Usher syndrome (e.g., Usher syndrome type 1B) using a DNA vector having a heterologous MYO7A gene or portion thereof (e.g., as part of a trans-splicing molecule). In some embodiments, the subject is being treated for Wagner syndrome using a DNA vector having a heterologous VCAN gene or portion thereof (e.g., as part of a trans-splicing molecule). In some embodiments, the subject is being treated for Usher syndrome type 2A using a DNA vector having a heterologous USH2A gene or portion thereof (e.g., as part of a trans-splicing molecule). In some embodiments, the subject is being treated for AMD 1 using a DNA vector having a heterologous HMCN1 gene or portion thereof (e.g., as part of a trans-splicing molecule).

The invention also provides methods of treating a disease or disorder selected from the group consisting of an ocular disorder, a liver disorder, a neurological disorder, an immune disorder, a cancer, a cardiovascular disorder, a blood coagulation disorder, a lysosomal storage disorder, or type 2 diabetes. The disorder may be an ocular disorder that is a retinal dystrophy.

The disorder may be a Mendelian-heritable retinal dystrophy. The retinal dystrophy may be selected from the group consisting of LCA, Stargardt Disease, pseudoxanthoma elasticum, rod cone dystrophy, exudative vitreoretinopathy, Joubert Syndrome, CSNB-1C, age-related macular degeneration, retinitis pigmentosa, stickler syndrome, microcephaly and chorioretinopathy, retinitis pigmentosa, CSNB 2, Usher syndrome, and Wagner syndrome.

The disorder may be a neurological disorder, wherein the neurological disorder is a neurodegenerative disease. The neurodegenerative disease may be selected from the group consisting of Alzheimer's disease, Parkinson's disease, or multiple sclerosis. The neurodegenerative disease may be an autoimmune disease of the central nervous system (CNS). The autoimmune disease of the CNS may be multiple sclerosis, encephalomyelitis, a paraneoplastic syndrome, autoimmune inner ear disease, or opsoclonus myoclonus syndrome. The neurological disorder may be a cerebral infarction, spinal cord injury, central nervous system disorder, a neuropsychiatric disorder, or a channelopathy. The neurological disorder may be a channelopathy selected from epilepsy or a migraine. The neurological disorder may be an anxiety disorder, a mood disorder, a childhood disorder, a cognitive disorder, schizophrenia, a substance related disorders, or an eating disorders. The neurological disorder may be a symptom of a cerebral infarction, stroke, traumatic brain injury, or spinal cord injury.

The lysosomal storage disorder may be selected from the group consisting of Tay-Sachs disease, Gaucher disease, Fabry disease, Pompe disease, Niemann-Pick disease, and mucopolysaccharidosis (MPS).

The cardiovascular disorder may be a degenerative heart disease, a coronary artery disease, an ischemia, angina pectoris, an acute coronary syndrome, a peripheral vascular disease, a peripheral arterial disease, a cerebrovascular disease, or atherosclerosis. The cardiovascular disorder may be a degenerative heart disease selected from the group consisting of an ischemic cardiomyopathy, a conduction disease, and a congenital defect.

The disorder may be an immune disorder which is an autoimmune disorder. The autoimmune disorder may be type 1 diabetes, multiple sclerosis, rheumatoid arthritis, lupus, encephalomyelitis, a paraneoplastic syndrome, autoimmune inner ear disease, or opsoclonus myoclonus syndrome, autoimmune hepatitis, uveitis, autoimmune retinopathy, neuromyelitis optica, psoriatic arthritis, psoriasis, myasthenia gravis, chronic Lyme disease, celiac disease, chronic inflammatory demyelinating polyneuropathy, peripheral neuropathy, fibromyalgia, Hashimoto's thyroiditis, ulcerative colitis, or Kawasaki disease.

The disease may be a liver disease selected from the group consisting of hepatitis, Alagille syndrome, biliary atresia, liver cancer, cirrhosis, a cystic disease, Caroli's syndrome, congenital hepatic fibrosis, fatty liver, galactosemia, primary sclerosing cholangitis, tyrosinemia, glycogen storage disease, Wilson's disease, and an endocrine deficiency. The liver disease may be a liver cancer selected from the group consisting of a hepatocellular hyperplasia, a hepatocellular adenomas, a focal nodular hyperplasia, or a hepatocellular carcinoma.

The disease may be a cancer which is a blood cancer or a solid tissue cancer. The blood cancer may be acute lymphoblastic leukemia, acute myeloblastic leukemia, chromic myelogenous leukemia, Hodgkin's disease, multiple myeloma, and non-Hodgkin's lymphoma. The solid tissue cancer may be a liver cancer, kidney cancer, a breast cancer, a prostate cancer, a gastric cancer, an esophageal cancer, a stomach cancer, an intestinal cancer, a colorectal cancer, a bladder cancer, a head and neck cancer, a skin cancer, or a brain cancer.

Any of the vectors of the present invention (e.g., circular DNA vectors as described herein and/or DNA vectors containing a DD element) can be administered to a subject in a dosage from 10 μg to 10 mg of DNA (e.g., from 25 μg to 5.0 mg, from 50 μg to 2.0 mg, or from 100 μg to 1.0 mg of DNA, e.g., from 10 μg to 20 μg, from 20 μg to 30 μg, from 30 μg to 40 μg, from 40 μg to 50 μg, from 50 μg to 75 μg, from 75 μg to 100 μg, from 100 μg to 200 μg, from 200 μg to 300 μg, from 300 μg to 400 μg, from 400 μg to 500 μg, from 500 μg to 1.0 mg, from 1.0 mg to 5.0 mg, or from 5.0 mg to 10 mg of DNA, e.g., about 10 μg, about 20 μg, about 30 μg, about 40 μg, about 50 μg, about 60 μg, about 70 μg, about 80 μg, about 90 μg, about 100 μg, about 150 μg, about 200 μg, about 250 μg, about 300 μg, about 350 μg, about 400 μg, about 450 μg, about 500 μg, about 600 μg, about 700 μg, about 750 μg, about 1.0 mg, about 2.0 mg, about 2.5 mg, about 5.0 mg, about 7.5 mg, or about 10 mg of DNA).

In some embodiments, administration of a DNA vector of the invention (e.g., a circular DNA vector as described herein and/or a DNA vector containing a DD element), or a composition thereof, is non-immunogenic or less likely to induce an immune response in a subject compared with administration of other gene therapy vectors (e.g., plasmid DNA vectors and viral vectors). Methods of assessing immunogenicity of a vector are described above.

The synthetic DNA vectors provided herein (e.g., circular DNA vectors as described herein and/or DNA vectors containing a DD element) can be amenable to repeat dosing due to their ability to infect target cells without triggering an immune response or inducing a reduced immune response relative to an AAV vector, as discussed above. Thus, the invention provides methods of repeatedly administering the vectors and pharmaceutical compositions described herein. Any of the aforementioned dosing quantities may be repeated at a suitable frequency and duration. In some embodiments, the subject receives a dose about twice per day, about once per day, about five times per week, about four times per week, about three times per week, about twice per week, about once per week, about twice per month, about once per month, about once every six weeks, about once every two months, about once every three months, about once every four months, twice per year, once yearly, or less frequently. In some embodiments, the number and frequency of doses corresponds with the rate of turnover of the target cell. It will be understood that in long-lived post-mitotic target cells transfected using the vectors described herein, a single dose of vector may be sufficient to maintain expression of the heterologous gene within the target cell for a substantial period of time. Thus, in other embodiments, a DNA vector provided herein may be administered to a subject in a single dose. The number of occasions in which heterologous nucleic acid is delivered to the subject can be that which is required to maintain a clinical (e.g., therapeutic) benefit.

Methods of the invention include administration of a DNA vector (e.g., a circular DNA vector as described herein and/or a DNA vector containing a DD element) or pharmaceutical composition thereof through any suitable route. The DNA vector or pharmaceutical composition thereof can be administered systemically or locally, e.g., intravenously, ocularly (e.g., intravitreally, subretinally, by eye drop, intraocularly, intraorbitally), intramuscularly, intravitreally (e.g., by intravitreal injection), intradermally, intrahepatically, intracerebrally, intramuscularly, percutaneously, intraarterially, intraperitoneally, intralesionally, intracranially, intraarticularly, intraprostatically, intrapleurally, intratracheally, intrathecally, intranasally, intravaginally, intrarectally, intratumorally, subcutaneously, subconjunctivally, intravesicularly, mucosally, intrapericardially, intraumbilically, orally, topically, transdermally, by inhalation, by aerosolization, by injection (e.g., by jet injection), by electroporation, by implantation, by infusion (e.g., by continuous infusion), by localized perfusion bathing target cells directly, by catheter, by lavage, in creams, or in lipid compositions.

Additionally, or alternatively, vectors can be administered to host cells ex vivo, such as by cells explanted from an individual patient, followed by reimplantation of the host cells into a patient, e.g., after selection for cells which have incorporated the vector. Thus, in some aspects, the disclosure provides transfected host cells and methods of administration thereof for treating a disease.

The invention provides methods of inducing episomal expression of a heterologous gene in a subject in need thereof. For example, episomal expression of a heterologous gene encoding a therapeutic replacement protein (e.g., a monogenic therapeutic replacement protein) can be induced in a subject having a defect or absence of the protein to be replaced (e.g., thereby causing a coagulation disorder, a lysosomal storage disorder, or any other disorders treatable by protein replacement therapy) by administering to the subject the isolated DNA vector (or a composition thereof) of the invention (e.g., an isolated circular DNA vector that lacks an origin of replication and/or a drug resistance gene; a recombination site; and any other element associated with bacterial synthesis (e.g., dam and dcm methylation patterns)). In particular instances, episomal expression of a heterologous gene encoding Factor VII is induced in a subject having a Factor VII deficiency by administering to the subject a DNA vector of the invention that encodes Factor VII. In some instances, episomal expression of a heterologous gene encoding Factor VIII is induced in a subject having hemophilia A by administering to the subject a DNA vector of the invention that encodes Factor VIII. In other instances, episomal expression of a heterologous gene encoding Factor IX is induced in a subject having hemophilia B by administering to the subject a DNA vector of the invention that encodes Factor IX. In some instances, episomal expression of a heterologous gene encoding Factor X is induced in a subject having a Factor X deficiency by administering to the subject a DNA vector of the invention that encodes Factor X. In other instances, episomal expression of a heterologous gene encoding Factor XI is induced in a subject having a Factor XI deficiency by administering to the subject a DNA vector of the invention that encodes Factor XI. In some instances, episomal expression of a heterologous gene encoding Factor XIII is induced in a subject having a Factor XIII deficiency by administering to the subject a DNA vector of the invention that encodes Factor XIII. In some instances, episomal expression of a heterologous gene encoding von Willebrand factor is induced in a subject having von Willebrand disease by administering to the subject a DNA vector of the invention that encodes von Willebrand factor. In other instances, episomal expression of a heterologous gene encoding protein C is induced in a subject having a protein C deficiency by administering to the subject a DNA vector of the invention that encodes protein C. In some instances, episomal expression of a heterologous gene encoding antithrombin III is induced in a subject having an antithrombin III deficiency by administering to the subject a DNA vector of the invention that encodes antithrombin III. In some instances, episomal expression of a heterologous gene encoding fibrinogen is induced in a subject having a fibrinogen deficiency by administering to the subject a DNA vector of the invention that encodes fibrinogen. In other instances, episomal expression of a heterologous gene encoding C1-esterase inhibitor is induced in a subject having hereditary angioedema by administering to the subject a DNA vector of the invention that encodes C1-esterase inhibitor. In some instances, episomal expression of a heterologous gene encoding alpha-1 protease inhibitor is induced in a subject having a1-P1 deficiency by administering to the subject a DNA vector of the invention that encodes alpha-1 protease inhibitor. In some instances, episomal expression of a heterologous gene encoding glucocerebrosidase is induced in a subject having Gaucher disease by administering to the subject a DNA vector of the invention that encodes glucocerebrosidase. In other instances, episomal expression of a heterologous gene encoding alpha-L-iduronidase is induced in a subject having mucopolysaccharidosis I by administering to the subject a DNA vector of the invention that encodes alpha-L-iduronidase. In some instances, episomal expression of a heterologous gene encoding iduronate sulfatase is induced in a subject having mucopolysaccharidosis II by administering to the subject a DNA vector of the invention that encodes iduronate sulfatase. In some instances, episomal expression of a heterologous gene encoding N-acetylgalactosamine-4-sulfatase is induced in a subject having mucopolysaccharidosis VI by administering to the subject a DNA vector of the invention that encodes N-acetylgalactosamine-4-sulfatase. In other instances, episomal expression of a heterologous gene encoding N-acetylgalactosamine-6-sulfatase is induced in a subject having mucopolysaccharidosis IVA by administering to the subject a DNA vector of the invention that encodes N-acetylgalactosamine-6-sulfatase. In some instances, episomal expression of a heterologous gene encoding heparan sulfate sulfatase is induced in a subject having mucopolysaccharidosis IIIA by administering to the subject a DNA vector of the invention that encodes heparan sulfate sulfatase. In some instances, episomal expression of a heterologous gene encoding alpha-galactosidase A is induced in a subject having Fabry disease by administering to the subject a DNA vector of the invention that encodes alpha-galactosidase A. In other instances, episomal expression of a heterologous gene encoding alpha-glucosidase is induced in a subject having Pompe disease by administering to the subject a DNA vector of the invention that encodes alpha-glucosidase. In some instances, episomal expression of a heterologous gene encoding acid sphingomyelinase is induced in a subject having Niemann-Pick type B disease by administering to the subject a DNA vector of the invention that encodes acid sphingomyelinase. In some instances, episomal expression of a heterologous gene encoding arylsuphatase A is induced in a subject having metachromatic leukodystrophy by administering to the subject a DNA vector of the invention that encodes arylsuphatase A. In other instances, episomal expression of a heterologous gene encoding lysosomal acid lipase (LAL) is induced in a subject having LAL deficiency by administering to the subject a DNA vector of the invention that encodes lysosomal acid lipase. In some instances, episomal expression of a heterologous gene encoding sucrase-isomaltase is induced in a subject having sucraseisomaltase deficiency by administering to the subject a DNA vector of the invention that encodes sucrase-isomaltase. In some instances, episomal expression of a heterologous gene encoding adenosime deaminase (ADA) is induced in a subject having an ADA deficiency by administering to the subject a DNA vector of the invention that encodes adenosime deaminase. In other instances, episomal expression of a heterologous gene encoding insulin-like growth factor 1 (IGF-1) is induced in a subject having an IGF-1 deficiency (e.g., primary IGF-1 deficiency) by administering to the subject a DNA vector of the invention that encodes IGF-1. In some instances, episomal expression of a heterologous gene encoding alkaline phosphatase is induced in a subject having hypophosphatasia by administering to the subject a DNA vector of the invention that encodes alkaline phosphatase. In some instances, episomal expression of a heterologous gene encoding porphobilinogen deaminase is induced in a subject having acute intermittent porphyria by administering to the subject a DNA vector of the invention that encodes porphobilinogen deaminase.

Additionally or alternatively, the present invention includes methods of treating a subject having a disease or disorder by administering to the subject the isolated DNA vector (or a composition thereof) of the invention (e.g., an isolated circular DNA vector that lacks an origin of replication and/or a drug resistance gene; a recombination site; and any other element associated with bacterial synthesis (e.g., dam and dcm methylation patterns)). In particular instances, a subject having a Factor VII deficiency is treated by administering to the subject a DNA vector of the invention that encodes Factor VII. In some instances, a subject having hemophilia A is treated by administering to the subject a DNA vector of the invention that encodes Factor VIII. In other instances, a subject having hemophilia B is treated by administering to the subject a DNA vector of the invention that encodes Factor IX. In some instances, a subject having a Factor X deficiency is treated by administering to the subject a DNA vector of the invention that encodes Factor X. In other instances, a subject having a Factor XI deficiency is treated by administering to the subject a DNA vector of the invention that encodes Factor XI. In some instances, a subject having a Factor XIII deficiency is treated by administering to the subject a DNA vector of the invention that encodes Factor XIII. In some instances, a subject having von Willebrand disease is treated by administering to the subject a DNA vector of the invention that encodes von Willebrand factor. In other instances, a subject having a protein C deficiency is treated by administering to the subject a DNA vector of the invention that encodes protein C. In some instances, a subject having an antithrombin III deficiency is treated by administering to the subject a DNA vector of the invention that encodes antithrombin III. In some instances, a subject having a fibrinogen deficiency is treated by administering to the subject a DNA vector of the invention that encodes fibrinogen. In other instances, a subject having hereditary angioedema is treated by administering to the subject a DNA vector of the invention that encodes C1-esterase inhibitor. In some instances, a subject having a1-P1 deficiency is treated by administering to the subject a DNA vector of the invention that encodes alpha-1 protease inhibitor. In some instances, a subject having Gaucher disease is treated by administering to the subject a DNA vector of the invention that encodes glucocerebrosidase. In other instances, a subject having mucopolysaccharidosis I is treated by administering to the subject a DNA vector of the invention that encodes alpha-L-iduronidase. In some instances, a subject having mucopolysaccharidosis II is treated by administering to the subject a DNA vector of the invention that encodes iduronate sulfatase. In some instances, a subject having mucopolysaccharidosis VI is treated by administering to the subject a DNA vector of the invention that encodes N-acetylgalactosamine-4-sulfatase. In other instances, a subject having mucopolysaccharidosis IVA is treated by administering to the subject a DNA vector of the invention that encodes N-acetylgalactosamine-6-sulfatase. In some instances, a subject having mucopolysaccharidosis IIIA is treated by administering to the subject a DNA vector of the invention that encodes heparan sulfate sulfatase. In some instances, a subject having Fabry disease is treated by administering to the subject a DNA vector of the invention that encodes alpha-galactosidase A. In other instances, a subject having Pompe disease is treated by administering to the subject a DNA vector of the invention that encodes alpha-glucosidase. In some instances, a subject having Niemann-Pick type B disease is treated by administering to the subject a DNA vector of the invention that encodes acid sphingomyelinase. In some instances, a subject having metachromatic leukodystrophy is treated by administering to the subject a DNA vector of the invention that encodes arylsuphatase A. In other instances, a subject having LAL deficiency is treated by administering to the subject a DNA vector of the invention that encodes lysosomal acid lipase. In some instances, a subject having sucraseisomaltase deficiency is treated by administering to the subject a DNA vector of the invention that encodes sucrase-isomaltase. In some instances, a subject having an ADA deficiency is treated by administering to the subject a DNA vector of the invention that encodes adenosime deaminase. In other instances, a subject having an IGF-1 deficiency (e.g., primary IGF-1 deficiency) is treated by administering to the subject a DNA vector of the invention that encodes IGF-1. In some instances, a subject having hypophosphatasia is treated by administering to the subject a DNA vector of the invention that encodes alkaline phosphatase. In some instances, a subject having acute intermittent porphyria is treated by administering to the subject a DNA vector of the invention that encodes porphobilinogen deaminase.

Assessment and Monitoring

Assessment of the efficiency of transfection of any of the vectors described herein can be performed using any method known in the art or described herein. Isolating a transfected cell can also be performed in accordance with standard techniques. For example, a cell comprising a heterologous gene can express a visible marker, such as a fluorescent protein (e.g., GFP) or other reporter protein, encoded by the sequence of the heterologous gene that aids in the identification and isolation of a cell or cells comprising the heterologous gene. A cell containing a heterologous gene can also express a selectable marker from the gene. Survival of the cell under certain conditions, for example exposure to a cytotoxic substance or the lack of a nutrient or substrate ordinarily required for survival, may be dependent on expression or lack of expression of a selectable marker. Thus, survival or lack of survival of cells under such conditions allows for identification and isolation cells or colonies of cells that contain a heterologous gene. Cells containing a heterologous gene can also be characterized by examining the nucleic acid sequence (e.g., an RNA sequence, e.g., an mRNA sequence) of the host cell, such as by Southern Blotting or PCR analysis, to assay for the presence of the heterologous gene contained in the vector.

Accordingly, methods of the present invention include, after administering any of the vectors described herein to a subject, subsequently detecting the expression of the heterologous gene in the subject. Expression can be detected one week to four weeks after administration, one month to four months after administration, four months to one year after administration, one year to five years after administration, or five years to twenty years after administration (e.g., at least one week, at least two weeks, at least one month, at least four months, at least one year, at least two years, at least five years, at least ten years after administration). At any of these detection timepoints, persistence (e.g., episomal persistence) of the DNA vector may be observed. In some embodiments, the persistence of the circular DNA vector is from 5% to 50% greater, 50% to 100% greater, one-fold to five-fold, or five-fold to ten-fold (e.g., at least 5%, 10%, 20%, 30%, 40%, 50%, 75%, one-fold, two-fold, three-fold, four-fold, five-fold, six-fold, seven-fold, eight-fold, nine-fold, ten-fold, or more) greater than a reference vector (e.g., a circular vector produced in bacteria or having one or more bacterial signatures not present in the vector of the invention).

The examples that follow do not limit the scope of the embodiments described herein. One skilled in the art will appreciate that modifications can be made in the following examples which are intended to be encompassed by the spirit and scope of the invention.

EXAMPLES

Recombinant AAV (rAAV) vectors have an established record of high-efficiency gene transfer in a variety of model systems and are now being tested as therapeutic modalities in a wide range of human diseases. Studies in animals and humans have shown that rAAV vector genomes persist in vivo predominantly as circular episomes. The present invention is based on the discovery that such persistence can be replicated using synthetic techniques to produce circular DNA vectors. Molecular analysis of rAAV episomal genomes isolated from both animals and humans reveals that these circular genomes contain terminal repeat sequences. In some of the following examples, terminal repeat sequences identified within rAAV episomal genomes include a Double D (DD) element, which is a result of recombination of the inverted terminal repeats (ITRs) located at each end of the linear AAV genome, shown in FIG. 1. Such synthetic DNA vectors can reduce immunogenicity and inflammation in the host relative to vectors generated in bacteria, since DNA produced in bacteria contains inherent bacterial signatures (CpG motifs) as well as impurities from the bacteria themselves (endotoxin, bacterial genomic DNA and RNA) that can lead to loss of the plasmid and gene expression in vivo.

Example 1. Synthetic Production of DNA Vectors Having a DD Element

Step 1—Production of rAAV2-eGFP Virus, Followed by Cell Transduction.

Figure 4:
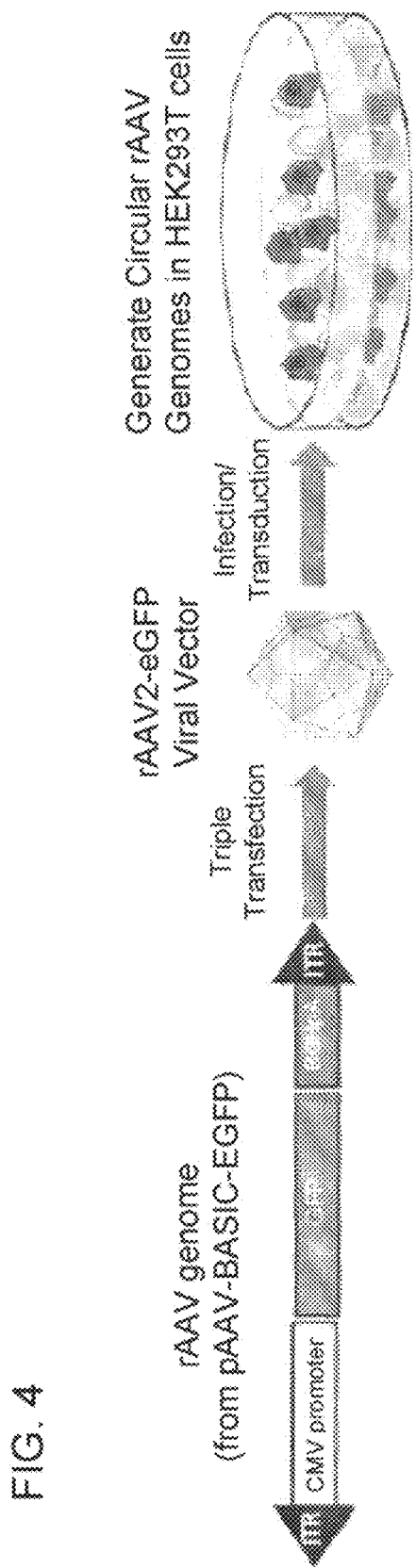
FIG. 4 is a schematic diagram showing a process for generating circular rAAV genomes in vitro. A plasmid with a rAAV genome of interest is transfected with additional AAV production plasmids (triple transfection) to produce a rAAV viral vector (serotype 2) that contains the packaged genome. The resulting virus infects HEK293T cells, in which circular rAAV genomes are produced.

Plasmid pAAV-BASIC-EGFP was obtained (Vector Biolabs, Malvern, Pa.), which contained AAV2 ITRs flanking an expression cassette consisting of a CMV enhancer/promoter driving eGFP protein with a BGHpA signal. The plasmid was used in a triple transfection strategy in HEK293T cells to produce rAAV2-eGFP viral vectors. Two other plasmids used in the triple transfection were AAV helper plasmids pRep-Cap2 (Part No. 0912; Applied Viromics, Fremont, Calif.) and pHELP (Part No. 0913; Applied Viromics, Fremont, Calif.). The cells were transfected using a calcium phosphate kit (Profection Mammalian Transfection System, Part No. TM012; Promega, Madison, Wis.). At 48 hours post-transfection, the cells were lysed by freeze/thaw and treated with benzonase to generate a crude viral lysate. The virus titer in the crude lysate was determined to be $5.3 \times 10^{12}$ DNase-resistant particles (DRP)/mL by qPCR. To generate circular rAAV genomes, HEK293T cells were infected with the rAAV2-eGFP virus with a multiplicity of infection (MOI) of $1 \times 10^5$. FIG. 4 summarizes this process.

Step 2—Cloning and Characterization of rAAV Genome with DD Element.

Figure 5:
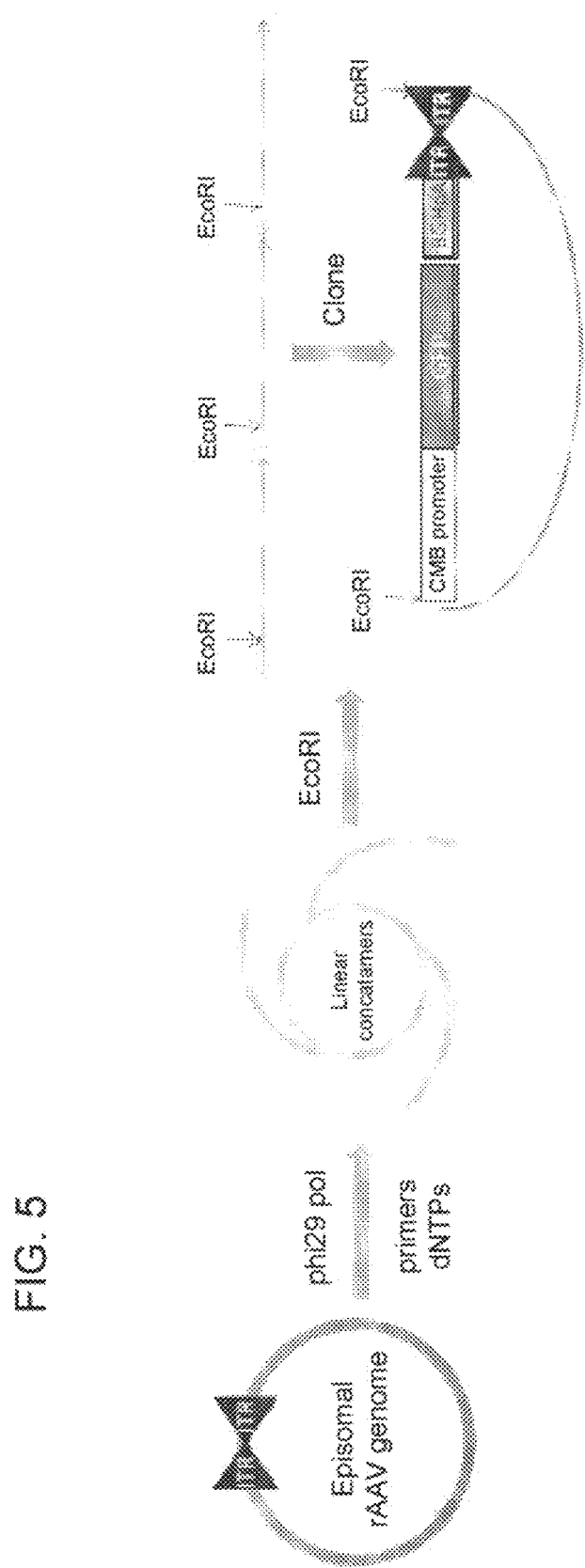
FIG. 5 is a schematic diagram showing a rolling-circle amplification reaction for detection of rAAV circular genomes. Total cellular DNA was digested with a restriction enzyme that does not cut within the AAV genome (in this case AvrII). The DNA was then treated with Plasmid-Safe DNase that degrades linear fragments but leaves circular, double-stranded DNA intact. The digestion reaction served as a template for linear rolling-circle amplification using random primers and Phi29 DNA polymerase. Large, linear concatameric arrays were produced following amplification of circular AAV episomes. The linear arrays were subsequently digested into unit-length monomeric AAV genomes by restriction enzyme digestion with EcoRI, which cleaves the AAV genome at a single point. The unit-length AAV genome was then cloned into the pBlueScript vector for further sequence analysis.

A summary of the cloning and characterization of rAAV genome having a DD element is shown in FIG. 5. Infected cells were harvested seven days post-infection and total cellular DNA was extracted from cells using a DNeasy Blood and Tissue kit (Qiagen; Germantown, Md.). To eliminate residual linear rAAV genomes, the DNA was treated with plasmid-safe DNase (Lucigen, Middleton, Wis.), which specifically degrades linear DNA, leaving double-stranded circular rAAV genomes intact. Residual circular rAAV genomes were amplified using a TEMPLIPHI™ kit (Part No. 25640010, GE Healthcare; Pittsburgh, Pa.). The TEMPLIPHI™ kit contains Phi29 polymerase that uses isothermal rolling circle amplification (RCA) for the exponential amplification of circular DNA using bacteriophage Phi29 DNA polymerase. The result of Phi29 amplification is long linear concatamers of DNA. This DNA is then digested with an enzyme (EcoRI) that cuts once within the rAAV genome to produce a unit-length genome that is cloned into pBlueScript II KS+ plasmid (Part No. 212207, Agilent Technologies; Chicago, Ill.).

The DD elements within the resulting clones were sequenced, and clone "TG-18," was identified as having an intact DD element (no deletions or rearrangements) of 165 bp in length. The sequence of clone TG-18 is shown in FIG. 6A.

Step 3—Generation of Template for DD Vector Production

Figure 7:
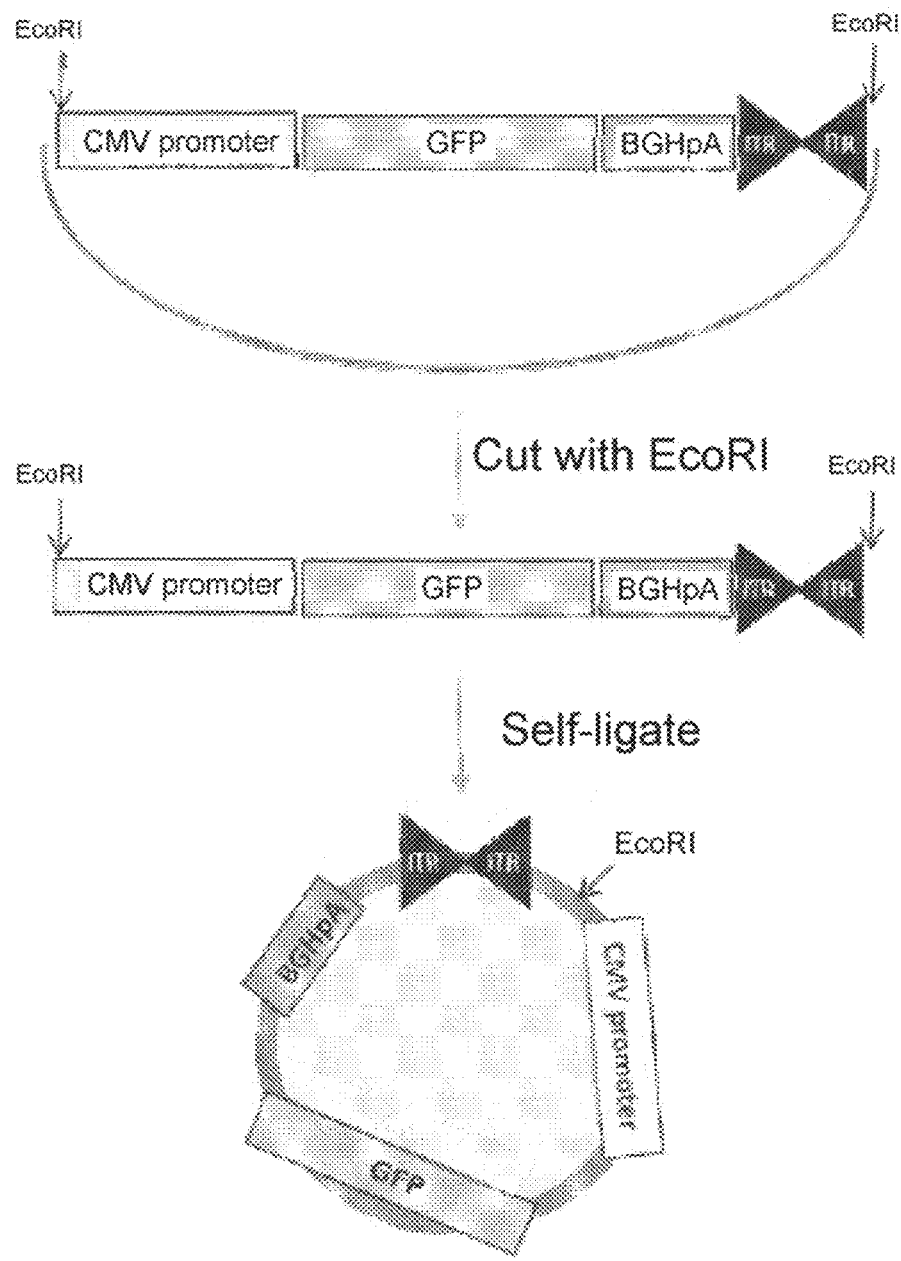
FIG. 7 is a schematic illustration showing generation of plasmid-derived circular template. Plasmid TG-18 is first digested with EcoRI to release a linear rAAV genome containing a terminal repeat sequence (DD element; represented as a bowtie). The ends of the linear fragment are ligated together to form a double-stranded circle.

Having identified an rAAV genome that contained a DD element (clone TG-18), the next step was to produce a circular template for downstream production of the DD vector. Plasmid TG-18 was digested with the restriction enzyme EcoRI, which released the linear unit-length rAAV genome from the plasmid backbone. The linear fragment was then self-ligated (rather than being ligated with a heterologous piece of DNA) to re-create a circular rAAV genome. Any linear fragments that were not ligated to form a circular product were eliminated by plasmid-safe DNase treatment. An illustration of this process is shown in FIG. 7.

Step 4—Production of DD Vector in a Test Tube

Figure 8:
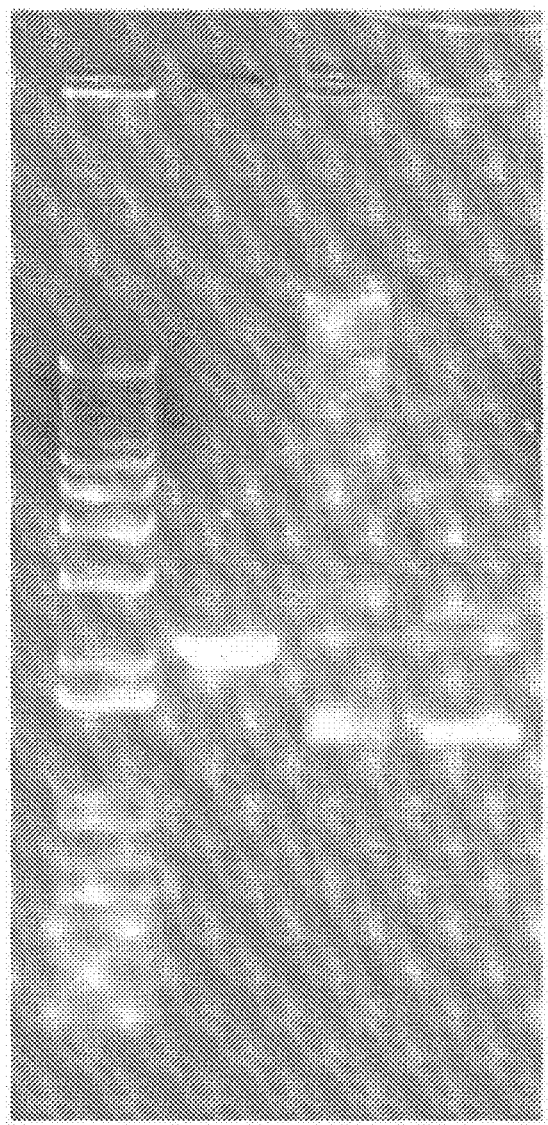
FIG. 8 is a photograph of an agarose gel containing bands of DNA at different steps of the template formation process. Lane 1 is the linear DNA fragment released from the pBlueScript vector. This fragment contains the CMV promoter, eGFP cDNA, BGHpA, and the terminal repeat sequence (DD element). Lane 2 is the result of self-ligation of the linear fragment from Lane 1. Multiple DNA forms are present and include circular and linear DNA of various sizes resulting from the ligation of one or multiple DNA fragments. Lane 3 shows the DNA remaining after treatment with plasmid-safe DNase that degrades linear, but not circular, DNA.

The circular rAAV genome produced in Step 3 originated in bacteria and contains bacterial signatures that have the potential to reduce persistence and/or to be immunogenic in the host. Step 4 amplifies this circular template in a test tube to generate more rAAV genomes that are devoid of bacterial signatures and contaminants. This is an advantage over traditional gene transfer vectors produced in bacteria. For test tube production, the circular template is amplified using a TEMPLIPHI™ kit (Part #25640010, GE Healthcare, Pittsburgh, Pa.). The TEMPLIPHI™ kit contains Phi29 polymerase that uses isothermal rolling circle amplification (RCA) for the exponential amplification of circular DNA using bacteriophage Phi29 DNA polymerase. The result of Phi29 amplification is long linear concatamers of DNA. We examined the amplified DNA to see if the DD element was faithfully replicated with Phi29 DNA polymerase. Results are shown in FIG. 8.

Figure 9:
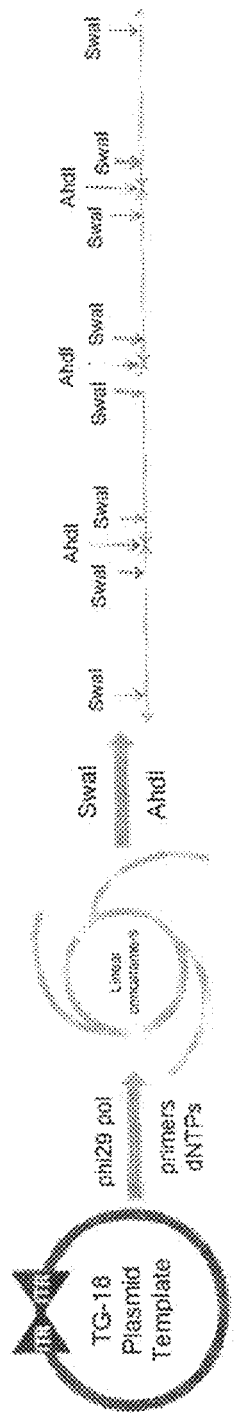
FIG. 9 is a schematic diagram showing a process for analyzing Phi29 fidelity on amplifying the terminal repeat sequence (DD element). A bacteria-derived circular DD vector serves as a template for linear rolling-circle amplification using random primers and Phi29 DNA polymerase. Large, linear concatameric arrays are produced following amplification of circular AAV episomes. The linear arrays are subsequently digested by restriction enzyme digestion to evaluate the presence of the DD element. The SwaI enzyme cuts on either side of the DD element to produce a 244-bp fragment. The AhdI enzyme cuts once within the DD element and digests the concatamers into unit-length fragments of 2.1 Kb.
Figure 10:
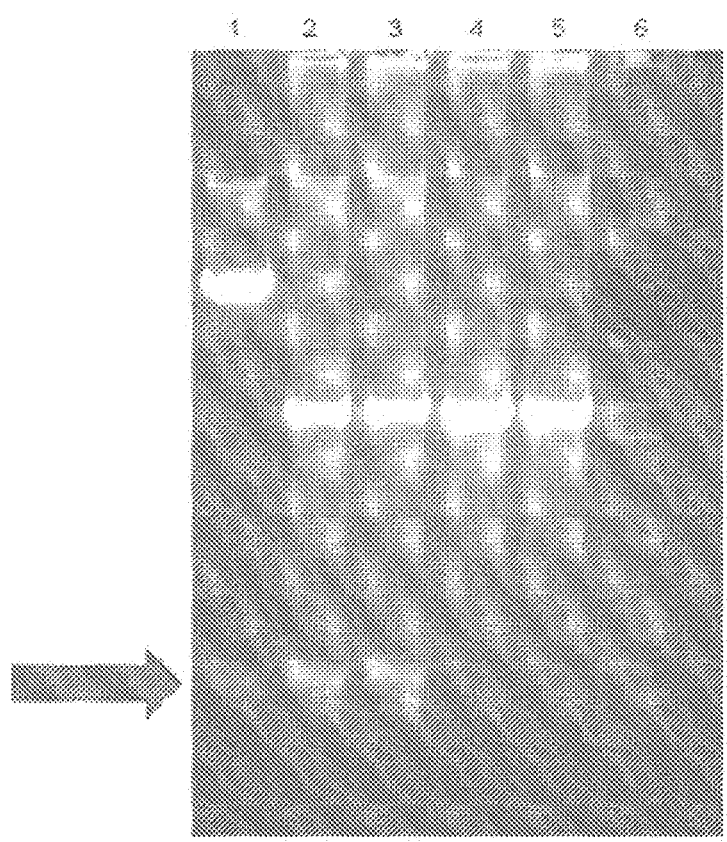
FIG. 10 is a photograph of an agarose gel showing the results of a Swat digestion of amplified DNA. DNA amplified from either 1 ng or 6 ng of the TG-18 plasmid template was digested with SwaI to produce a 244-bp fragment (Lanes 2 and 3, arrow). This is the same size fragment released from the original TG-18 plasmid vector (Lane 1). Also included is DNA amplified from a plasmid template lacking the DD element (TG-dDD) that was produced by removing the DD element from TG-18 using a SwaI digest (Lanes 4 and 5).
Figure 11:
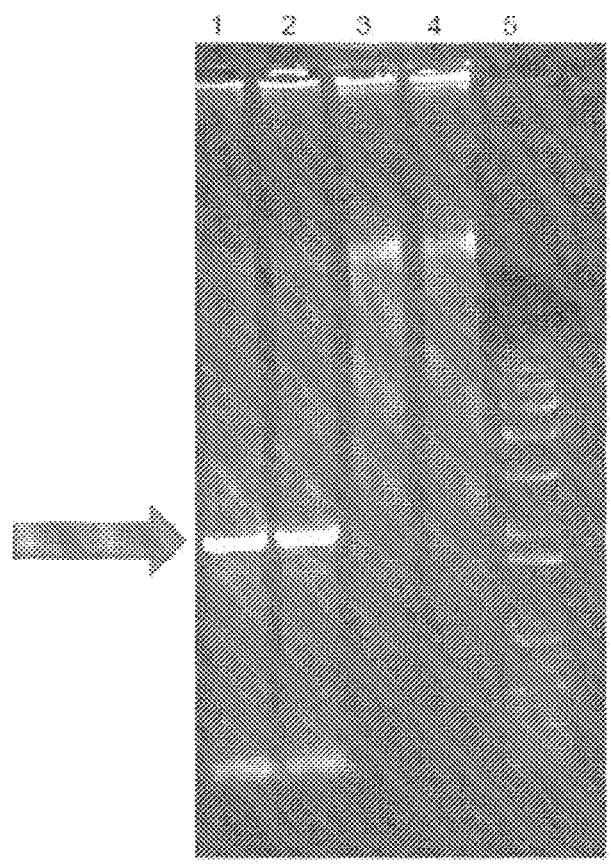
FIG. 11 is a photograph of an agarose gel showing AhdI digestion of amplified DNA. AhdI cuts once with in the DD element. DNA amplified from either 1 ng or 6 ng of the TG-18 plasmid template was digested with AhdI to produce a 2.1-kb fragment (Lanes 1 and 2, arrow). Also included is DNA amplified from a plasmid template lacking the DD element (TG-dDD; lanes 3 and 4). This DNA should not be digested with AhdI as it does not contain the DD element.

The amplified DNA was first digested with SwaI, which cuts on either side of the DD element (FIG. 9) to release a fragment of 244 bp in length. The SwaI fragment from the amplified DNA was the same size as the SwaI fragment from the original TG-18 pBlueScript plasmid (FIG. 10, arrow), indicating that Phi29 can amplify the DD element. The integrity of the amplified DD element was further analyzed by digestion with AhdI that cuts within the DD element. AhdI cuts once within the DD vector and digests the concatameric DNA into 2.1 kb unit-length genomes, as demonstrated in FIG. 11 (arrow).

Figure 12A:
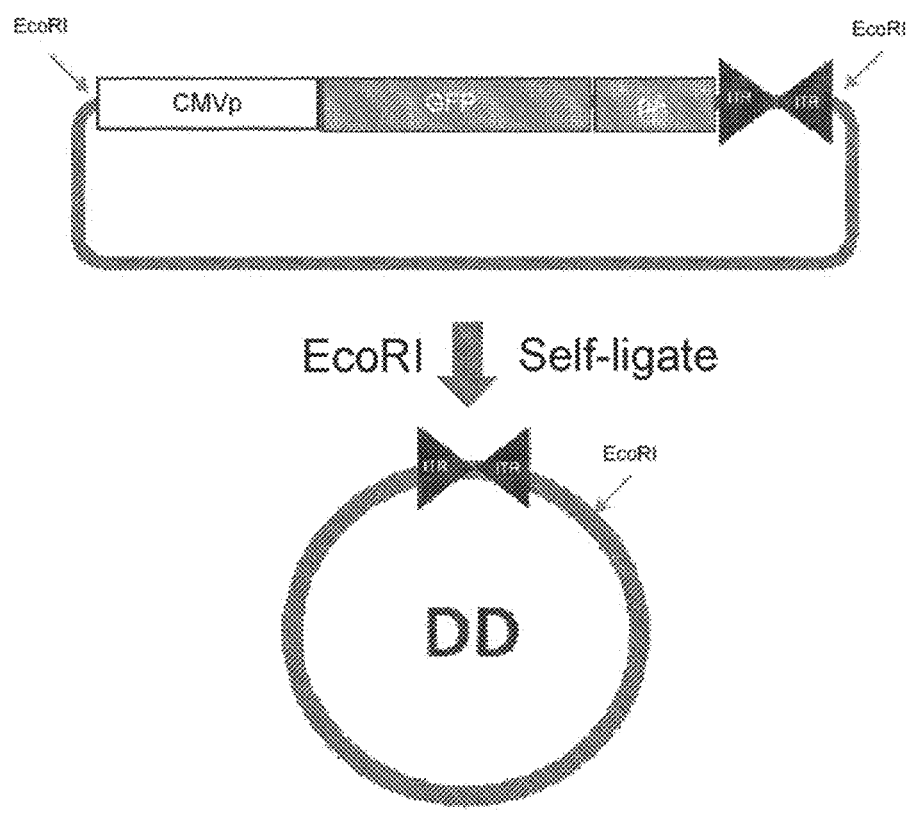
FIG. 12A is a schematic diagram showing self-ligation of a bacterial plasmid-derived template. A plasmid having a terminal repeat sequence-containing vector (here, a DD element-containing vector) is first digested with EcoRI to release a linear rAAV genome containing a terminal repeat sequence (a DD element) within the gene sequence represented as a bowtie. The ends of the linear fragment are ligated together to form a double-stranded circle.
Figure 12B:
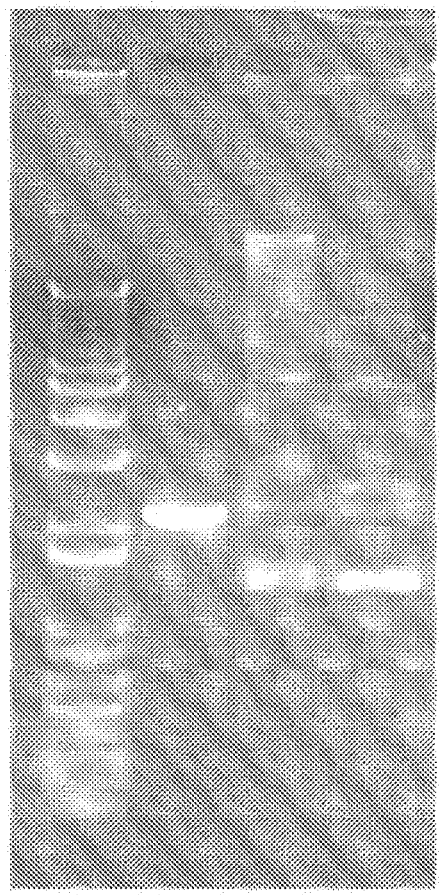
FIG. 12B is a photograph of an agarose gel showing DNA at different steps of the template formation process. Lane 1 is the linear DNA fragment released from the pBlueScript vector. This fragment contains the CMV promoter, eGFP cDNA, BGHpA, and the DD element. Lane 2 is the result of self-ligation of the linear fragment from Lane 1. Multiple DNA forms are present and includes circular as well as linear DNA of various sizes resulting from the ligation of one or multiple DNA fragments. Lane 3 shows the DNA remaining after treatment with plasmid-safe DNase that degrades linear, but not circular, DNA.
Figure 13A:
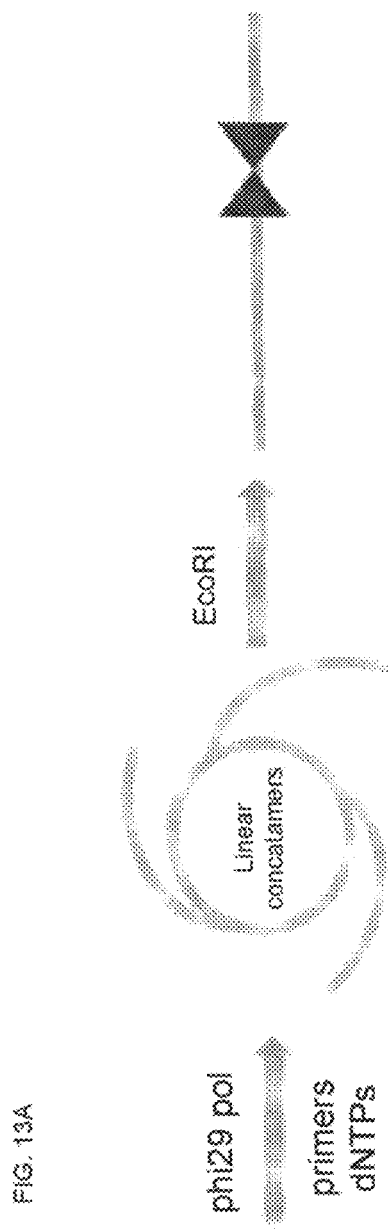
FIG. 13A is a schematic diagram showing the production of linear concatamers by Phi29 polymerase. The bacteria-derived template shown in FIGS. 11A and 11B served as a template for linear RCA using random primers and Phi29 DNA polymerase. Large, linear concatameric arrays were produced following amplification of circular AAV episomes. The linear arrays were subsequently digested into unit-length monomeric AAV genomes by restriction enzyme digestion with EcoRI.
Figure 13B:
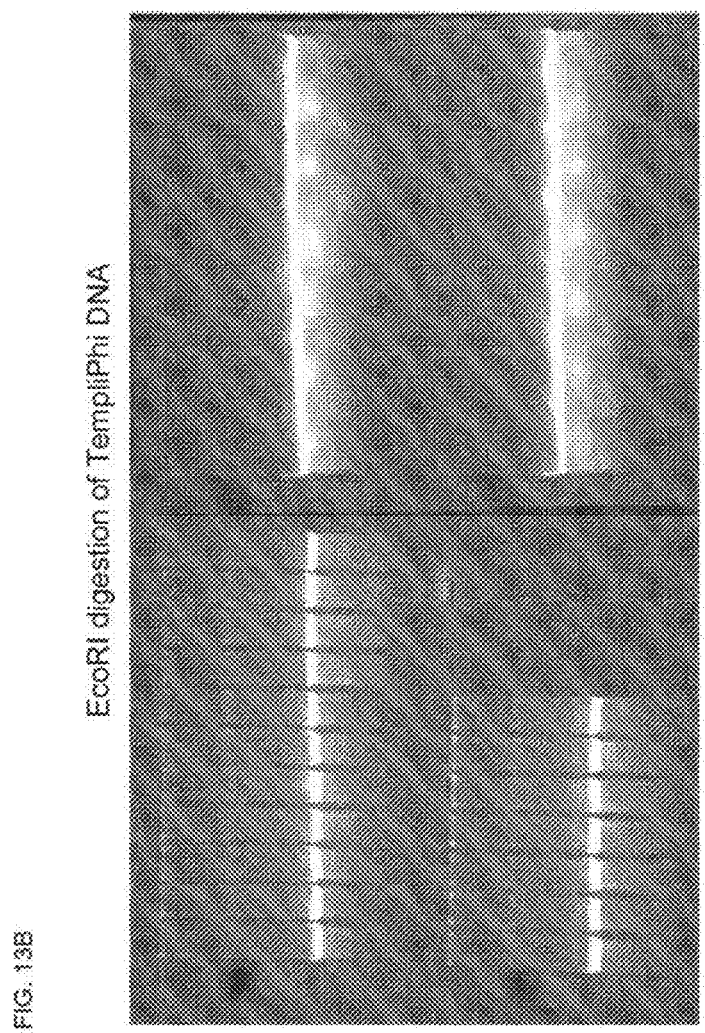
FIG. 13B is a photograph of an agarose gel showing size fractionated digested DNA.
Figure 14A:
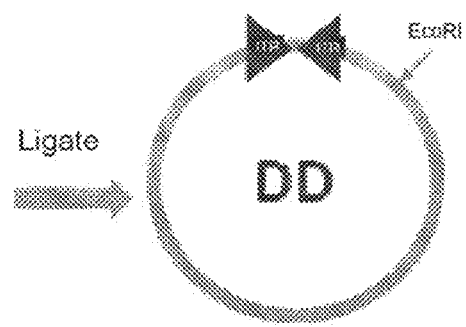
FIG. 14A is a schematic drawing of an in vitro-derived rAAV genome that has been self-ligated from linear form into a circular product.
Figure 14B:
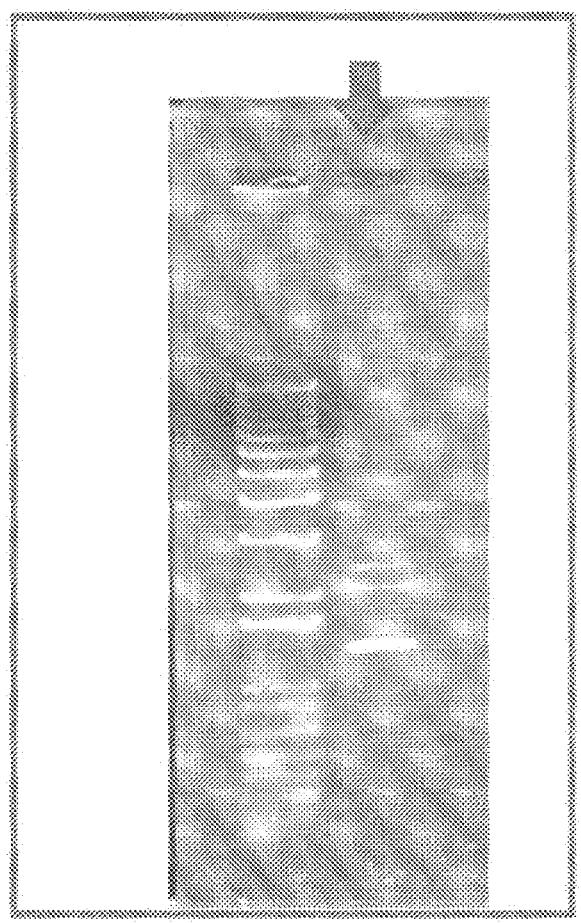
FIG. 14B is a photograph of an agarose gel showing the resulting monomeric circular DNA vector illustrated in FIG. 14A. The majority of the DNA is monomeric supercoiled circular DNA.

Having demonstrated that the DD element within the DD vector can be faithfully amplified, the next step was to generate the final circular DD vector products. An outline of the production strategy is shown in FIGS. 12-14. The circular rAAV genome produced in Step 3 is amplified using Phi29 polymerase that uses isothermal RCA for the exponential amplification of circular DNA using bacteriophage Phi29 DNA polymerase. The result of Phi29 amplification is long linear concatamers of DNA (FIG. 13A). This DNA is then digested with an enzyme (EcoRI) that cuts once within the rAAV genome to produce an AAV genome (i.e., a unit-length AAV genome; FIG. 13A). This AAV genome is then self-ligated to re-create a circular rAAV genome (FIG. 14A). Any linear fragments that were not ligated to form a circular product was eliminated by plasmid-safe DNase treatment.

Step 5—Confirmation of Gene Expression of DD Vector

Figure 15A:
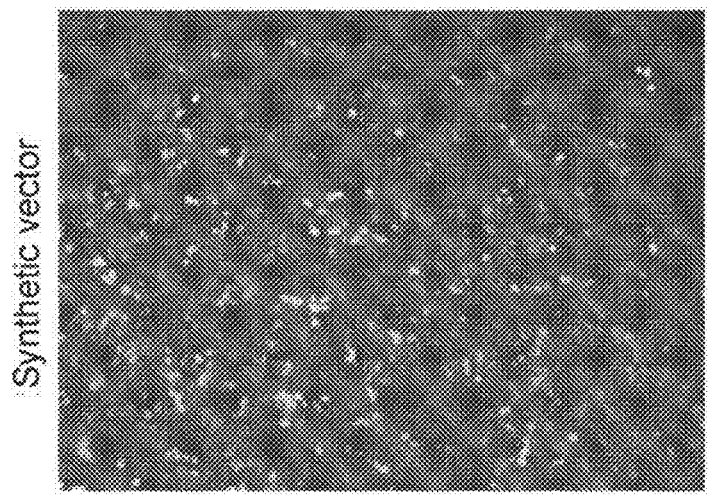
FIG. 15A is a photomicrograph showing GFP fluorescence of cells transfected with the synthetic vector characterized in FIG. 14B. Fluorescence was detected using a Spectramax MiniMax300 Imaging Cytometer.
Figure 15B:
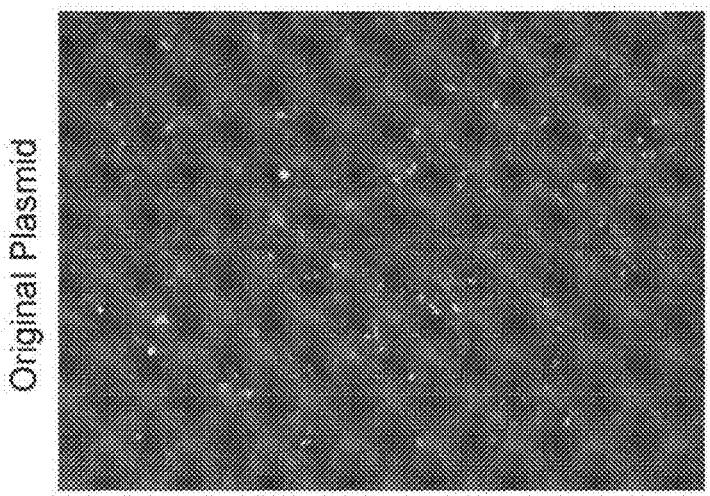
FIG. 15B is a photomicrograph showing GFP fluorescence of cells transfected with the original plasmid containing the rAAV genome. Fluorescence was detected using a Spectramax MiniMax300 Imaging Cytometer.
Figure 16:
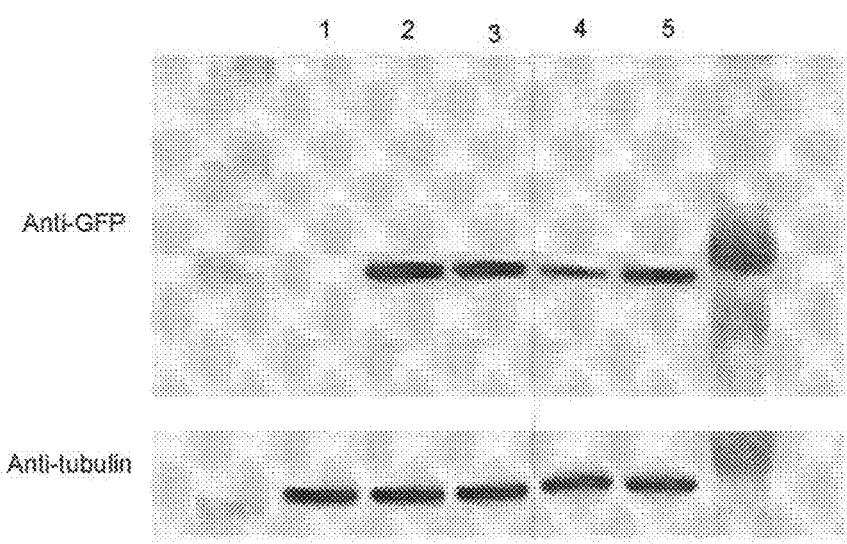
FIG. 16 is a photograph of a Western blot showing GFP expression by cells transfected with pBS alone (lane 1), an in vitro-produced TG-18-derived DD vector (lane 2), an in vitro-produced TG-18-derived vector without the DD element (lane 3), a plasmid-derived TG-18-derived DD vector (lane 4), and a plasmid-derived TG-18-derived vector without the DD element (lane 5). Bands showing anti-tubulin staining are shown as a control.

The last step in the in vitro production process is to confirm that the DD vector is biologically active (i.e., expresses the transgene in cultured cells). DD-containing DNA vector containing the eGFP expression cassette as a heterologous gene was transfected into HEK293T cells using Lipofectamine 2000 (Life Technologies, Carlsbad, Calif.). Cells were analyzed 48 hours later for GFP expression by immunofluorescence (FIGS. 15A and 15B) or western blotting (FIG. 16).

Example 2. Synthetic Production of Circular DNA Vectors

Monomeric DNA vectors were produced in which the vectors contain no bacterial plasmid DNA sequences and are synthesized entirely in a test tube (no replication in bacteria required). Therefore, the synthetic DNA vectors can endow a given target cell with transgene DNA that behaves like AAV viral DNA—without needing the virus itself. This strategy offers several advantages over viral vectors. First, it allows delivery of genes that are too large for packaging into common viral vectors. Furthermore, it enables repeat dosing, since there are no viral proteins that would trigger an immune response to prevent repeat dosing of another viral vector. In addition, the in vitro synthesis process has a greater potential for more efficient manufacturing relative to other viral vectors.

Figure 17:
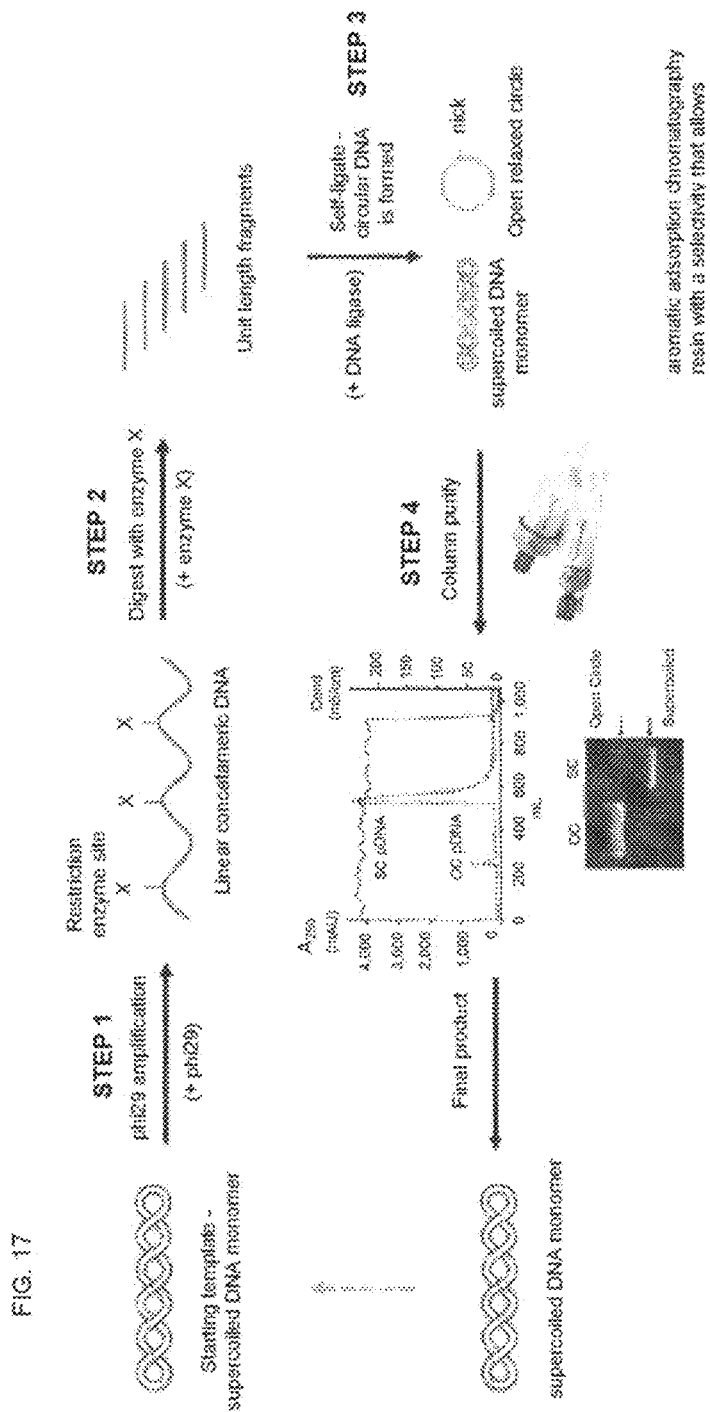
FIG. 17 is a schematic diagram showing an exemplary process for producing synthetic DNA vectors using rolling circle amplification. This process includes column purification to separate open circle DNA molecules from supercoiled DNA monomers.

An exemplary process for generating synthetic circular DNA vectors is shown in FIG. 17. Amplification of a supercoiled monomeric DNA template was performed using phi29 polymerase to generate linear concatameric DNA having a restriction site that defines the boundaries between repeated DNA fragments. The concatamers were digested using a restriction enzyme that cleaves the DNA into unit-length fragments. Next, DNA ligase was added to induce self-ligation of the DNA fragments, generating a mixture of DNA structures including open relaxed circles and supercoiled DNA monomers. This mixture was column purified using a thiophilic aromatic adsorption chromatography resin (Plasmidselect Xtra, GE Healthcare 28-4024-01), which has a selectivity that allows supercoiled covalently closed circular forms of plasmid DNA to be separated from open circular forms. Supercoiled DNA monomer obtained from this purification was recovered and can be used in the methods described herein or, alternatively, may serve as a template for additional amplification.

Example 3. Characterization of In-Vivo Persistence—GFP Expression

To characterize the degree of persistence of a synthetic circular DNA vector of the invention, mice are administered with three compositions, each including a different DNA vector: (1) plasmid CAG-GFP (SEQ ID NO: 42) as a negative control of persistence; (2) ΔDD CAG-GFP (a synthetic circular DNA vector lacking a DD element); and (3) DD CAG-GFP (a synthetic circular DNA vector having a DD element). Each group contains 32 mice total (eight mice per time point), and each composition is administered at 10 μg DNA per mouse by hydrodynamic injection. Eight mice from each group are sacrificed at each of the following time points: two weeks, four weeks, eight weeks, and sixteen weeks, and liver tissue is harvested and processed at each time point. Expression of GFP in liver cells is quantified according to known methods and compared across groups at each time point. Synthetic circular CAG-GFP is determined to be highly persistent if liver cells from mice administered with synthetic circular CAG-GFP express higher levels of GFP in comparison to liver cells from mice administered with plasmid CAG-GFP.

Example 4. Characterization of In-Vivo Persistence—mSEAP Expression

Another study to characterize the degree of persistence of a synthetic circular DNA vector of the invention involves heterologous expression of mouse secreted alkaline phosphatase (mSEAP), which is not endogenously expressed in mice. In this experiment, mice are administered with four compositions, each including a different DNA vector: (1) plasmid CAG-mSEAP as a negative control of persistence; (2) plasmid CAG-mSEAP-ΔCpG, which lacks CpG motifs; (3) ΔDD CAG-mSEAP-ΔCpG, which lacks a DD element and CpG motifs; and (4) DD CAG-mSEAP ΔCpG, which includes a DD element and lacks CpG motifs. Each group contains 12 mice, and each composition is administered at 20 μg DNA per mouse by hydrodynamic injection. Two mice from each group are sacrificed at each of the following time points: two weeks, four weeks, eight weeks, twelve weeks, sixteen weeks, and twenty-four weeks, and 200 μL blood is collected. Serum concentration of mSEAP is quantified in each sample according to known methods and compared across groups at each time point.

The effect of CpG motifs and/or a DD element on persistence is quantified by comparing mSEAP concentration across the experimental groups. For example, serum mSEAP levels are approximately equivalent across experimental groups at early time points; however, mice administered with vectors having higher persistence exhibit greater concentrations of mSEAP at later time points.

Numerated Embodiments

Some embodiments of the technology described herein can be defined according to any of the following numbered paragraphs:

1. An isolated circular DNA vector comprising one or more heterologous genes encoding a therapeutic replacement protein, wherein the DNA vector lacks:
   (a) an origin of replication and/or a drug resistance gene; and
   (b) a recombination site.
2. The DNA vector of paragraph 1, wherein the DNA vector comprises a terminal repeat sequence.
3. The DNA vector of paragraph 2, wherein the terminal repeat sequence is at least 10 bp in length.
4. The DNA vector of any one of paragraphs 1-3, wherein the terminal repeat sequence is a DD element.
5. The DNA vector of any one of paragraphs 1-4, wherein the DNA vector lacks an immunogenic bacterial signature.
6. The DNA vector of any one of paragraphs 1-5, wherein the DNA vector lacks an RNA polymerase arrest site.
7. The DNA vector of any one of paragraphs 1-6, wherein the DNA vector is substantially devoid of CpG islands.
8. The DNA vector of any one of paragraphs 1-7, wherein the therapeutic replacement protein is secreted into blood.
9. The DNA vector of any one of paragraphs 1-8, wherein the one or more heterologous genes comprises a trans-splicing molecule or a portion thereof (e.g., a binding domain).
10. The DNA vector of any one of paragraphs 1-9, wherein the DNA vector comprises one or more unmethylated GATC sequences, one or more unmethylated CCAGG sequences, and/or one or more CCTGG sequences.
11. The DNA vector of any one of paragraphs 1-10, wherein the heterologous gene is greater than 4.5 Kb in length.
12. The DNA vector of any one of paragraphs 1-11, wherein the DNA vector is double stranded.
13. The DNA vector of any one of paragraphs 1-12, wherein the DNA vector is monomeric.
14. The DNA vector of any one of paragraphs 1-13, wherein the DNA vector is supercoiled.
15. The DNA vector of any one of paragraphs 1-14, wherein the therapeutic replacement protein is indicated for treatment of an ocular disorder.
16. The DNA vector of paragraph 15, wherein the ocular disorder is a retinal dystrophy.
17. The DNA vector of paragraph 16, wherein the retinal dystrophy is selected from the group consisting of leber's congenital amaurosis (LCA), Stargardt Disease, pseudoxanthoma elasticum, rod cone dystrophy, exudative vitreoretinopathy, Joubert Syndrome, CSNB-1C, age-related macular degeneration, retinitis pigmentosa, stickler syndrome, microcephaly and chorioretinopathy, retinitis pigmentosa, CSNB 2, Usher syndrome, and Wagner syndrome.
18. The DNA vector of any one of paragraphs 1-14, wherein the therapeutic replacement protein is indicated for treatment of a blood coagulation disorder.
19. The DNA vector of paragraph 18, wherein the blood coagulation disorder is a hemophilia, von Willebrand's disease, factor XI deficiency, a fibrinogen disorder, or a vitamin K deficiency.
20. The DNA vector of paragraph 19, wherein the coagulation disorder is characterized by a mutation in a gene encoding for fibrinogen, prothrombin, factor V, factor VII, factor VIII, factor X, factor XI, factor XIII, or an enzyme involved in posttranslational modifications thereof, or an enzyme involved in vitamin K metabolism.
21. An isolated circular DNA vector comprising one or more heterologous genes encoding an antigen-binding protein, wherein the DNA vector lacks:
   (a) an origin of replication and/or a drug resistance gene; and
   (b) a recombination site.
22. The DNA vector of paragraph 21, wherein the antigen-binding protein is an antibody or an antigen-binding fragment thereof.
23. The DNA vector of paragraph 21 or 22, wherein the antigen-binding protein binds TNF, LT, IFN-α, IFN-γ, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-21, EMAP-II, GM-CSF, EGF, HER2, HER3, FGF, PDGF, BDNF, CNTF, CSF, G-CSF, NGF, PEDF, TGF, VEGF, gonadotropin, insulin-like growth factor, CD2, CD3, CD4, CD8, CD19, CD20, CD25, CD28, CD30, CD40, CD45, CD69, CD80, CD86, CD90, PD-1, PD-L1, amyloid beta, alkaline phosphatase, amyloid protein A, CCR4, folate receptor, mucin 5AC, PCSK-9, phosphatidyl-serine, or sclerostin.
24. The DNA vector of paragraph 22, wherein the antigen-binding protein is a monoclonal antibody, a bispecific antibody, or an antigen-binding fragment.
25. An isolated circular DNA vector comprising one or more heterologous genes encoding an enzyme, a growth factor, a hormone, an interleukin, an interferon, a cytokine, an anti-apoptosis factor, an anti-diabetic factor, a coagulation factor, an anti-tumor factor, a liver-secreted protein, or a neuroprotective factor, wherein the DNA vector lacks:
   (a) an origin of replication and/or a drug resistance gene; and
   (b) a recombination site.
26. The DNA vector of paragraph 25, wherein the growth factor is BDNF, CNTF, CSF, EGF, FGF, G-SCF, M-CSF, GM-CSF, NGF, PDGF, PEDF, TGF, VEGF, gonadotropin, or an insulin-like growth factor.
27. The DNA vector of paragraph 25, wherein the interleukin is IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, or IL-21.
28. The DNA vector of paragraph 25, wherein the interferon is IFN-α or IFN-γ.
29. The DNA vector of paragraph 25, wherein the coagulation factor is factor V, factor VII, factor VIII, factor IX, factor X, factor XI, factor XII, factor XIII, or von Willebrand factor.
30. The DNA vector of paragraph 25, wherein the neuroprotective factor is selected from the group consisting of a neurotrophin, Kifap3, Bcl-xl, Crmp1, Chk.beta., CALM2, Caly, NPG11, NPT1, Eef1a1, Dhps, Cd151, Morf412, CTGF, LDH-A, Atl1, NPT2, Ehd3, Cox5b, Tuba1a, gamma-actin, Rpsa, NPG3, NPG4, NPG5, NPG6, NPG7, NPG8, NPG9, and NPG10.

31. The DNA vector of paragraph 30, wherein the neurotrophin is selected from the group consisting of NGF, BDNF, NT-3, NT-4, and CNTF.

32. An isolated circular DNA vector comprising one or more heterologous genes associated with a disorder selected from the group consisting of an ocular disorder, a liver disorder, a neurological disorder, an immune disorder, a cancer, a cardiovascular disorder, a blood coagulation disorder, a lysosomal storage disorder, or type 2 diabetes, wherein the DNA vector lacks:
   (a) an origin of replication and/or a drug resistance gene; and
   (b) a recombination site.

33. The DNA vector of paragraph 32, wherein the disorder is an ocular disorder that is a retinal dystrophy.

34. The DNA vector of paragraph 33, wherein the disorder is a Mendelian-heritable retinal dystrophy.

35. The DNA vector of paragraph 33, wherein the retinal dystrophy is selected from the group consisting of leber's congenital amaurosis (LCA), Stargardt Disease, pseudoxanthoma elasticum, rod cone dystrophy, exudative vitreoretinopathy, Joubert Syndrome, CSNB-1C, age-related macular degeneration, retinitis pigmentosa, stickler syndrome, microcephaly and chorioretinopathy, retinitis pigmentosa, CSNB 2, Usher syndrome, and Wagner syndrome.

36. The DNA vector of paragraph 32, wherein the coagulation disorder is a hemophilia, von Willebrand's disease, factor XI deficiency, a fibrinogen disorder, or a vitamin K deficiency.

37. The DNA vector of paragraph 32, wherein the coagulation disorder is characterized by a mutation in a gene encoding for fibrinogen, prothrombin, factor V, factor VII, factor VIII, factor X, factor XI, factor XIII, or an enzyme involved in posttranslational modifications thereof, or an enzyme involved in vitamin K metabolism.

38. The DNA vector of paragraph 32 or 37, wherein the coagulation disorder is characterized by a mutation in FGA, FGB, FGG, F2, F5, F7, F10, F11, F13A, F13B, LMAN1, MCFD2, GGCX, or VKORC1.

39. The DNA vector of paragraph 32, wherein the neurological disorder is a neurodegenerative disease.

40. The DNA vector of paragraph 39, wherein the neurodegenerative disease is selected from the group consisting of Alzheimer's disease, Parkinson's disease, and multiple sclerosis.

41. The DNA vector of paragraph 39, wherein the neurodegenerative disease is an autoimmune disease of the central nervous system (CNS).

42. The DNA vector of paragraph 41, wherein the autoimmune disease of the CNS is multiple sclerosis, encephalomyelitis, a paraneoplastic syndrome, autoimmune inner ear disease, or opsoclonus myoclonus syndrome.

43. The DNA vector of paragraph 32, wherein the neurological disorder is a cerebral infarction, spinal cord injury, central nervous system disorder, a neuropsychiatric disorder, or a channelopathy.

44. The DNA vector of paragraph 43, wherein the channelopathy is epilepsy or migraine.

45. The DNA vector of paragraph 32, wherein the neurological disorder is an anxiety disorder, a mood disorder, a childhood disorder, a cognitive disorder, schizophrenia, a substance related disorder, or an eating disorder.

46. The DNA vector of paragraph 32, wherein the neurological disorder is a symptom of a cerebral infarction, stroke, traumatic brain injury, or spinal cord injury.

47. The DNA vector of paragraph 32, wherein the lysosomal storage disorder is selected from the group consisting of Tay-Sachs disease, Gaucher disease, Fabry disease, Pompe disease, Niemann-Pick disease, and mucopolysaccharidosis (MPS).

48. The DNA vector of paragraph 32, wherein the cardiovascular disorder is a degenerative heart disease, a coronary artery disease, an ischemia, angina pectoris, an acute coronary syndrome, a peripheral vascular disease, a peripheral arterial disease, a cerebrovascular disease, or atherosclerosis.

49. The DNA vector of paragraph 32, wherein the cardiovascular disorder is a degenerative heart disease selected from the group consisting of an ischemic cardiomyopathy, a conduction disease, and a congenital defect.

50. The DNA vector of paragraph 32, wherein the immune disorder is an autoimmune disorder.

51. The DNA vector of paragraph 50, wherein the autoimmune disorder is type 1 diabetes, multiple sclerosis, rheumatoid arthritis, lupus, encephalomyelitis, a paraneoplastic syndrome, autoimmune inner ear disease, or opsoclonus myoclonus syndrome, autoimmune hepatitis, uveitis, autoimmune retinopathy, neuromyelitis optica, psoriatic arthritis, psoriasis, myasthenia gravis, chronic Lyme disease, celiac disease, chronic inflammatory demyelinating polyneuropathy, peripheral neuropathy, fibromyalgia, Hashimoto's thyroiditis, ulcerative colitis, or Kawasaki disease.

52. The DNA vector of paragraph 32, wherein the disease is a liver disease selected from the group consisting of hepatitis, Alagille syndrome, biliary atresia, liver cancer, cirrhosis, a cystic disease, Caroli's syndrome, congenital hepatic fibrosis, fatty liver, galactosemia, primary sclerosing cholangitis, tyrosinemia, glycogen storage disease, Wilson's disease, and an endocrine deficiency.

53. The DNA vector of paragraph 52, wherein the liver disease is a liver cancer selected from the group consisting of a hepatocellular hyperplasia, a hepatocellular adenomas, a focal nodular hyperplasia, or a hepatocellular carcinoma.

54. The DNA vector of paragraph 33, wherein the cancer is a blood cancer or a solid tissue cancer.

55. The DNA vector of paragraph 54, wherein the blood cancer is acute lymphoblastic leukemia, acute myeloblastic leukemia, chromic myelogenous leukemia, Hodgkin's disease, multiple myeloma, and non-Hodgkin's lymphoma.

56. The DNA vector of paragraph 54, wherein the solid tissue cancer is a liver cancer, kidney cancer, a breast cancer, a gastric cancer, an esophageal cancer, a stomach cancer, an intestinal cancer, a colorectal cancer, a bladder cancer, a head and neck cancer, a skin cancer, or a brain cancer.

57. The DNA vector of any one of paragraphs 1-56, wherein the disorder is a recessively inherited disorder.

58. The DNA vector of any one of paragraphs 1-57, wherein the heterologous gene is expressible in a target cell selected from the group consisting of a liver cell, a retinal cell, a stem cell, a neural cell, a muscle cell, or a blood cell.

59. The DNA vector of any one of paragraphs 1-58, wherein the heterologous gene is expressible in a post-mitotic target cell.

60. The DNA vector of paragraph 58 or 59, wherein the target cell is a neural cell selected from the group consisting of a neuron, an astrocyte, an oligodendrocyte, and a Schwann cell.

61. The DNA vector of any one of paragraphs 1-60, wherein the therapeutic protein is secreted into blood.

62. The DNA vector of any one of paragraphs 1-61, wherein the DNA vector comprises a promoter sequence upstream of the one or more heterologous genes.

63. The DNA vector of any one of paragraphs 1-62, wherein the DNA vector comprises a polyadenylation site downstream of the one or more heterologous genes.

64. The DNA vector of any one of paragraphs 1-63, wherein the one or more heterologous genes comprises a trans-splicing molecule or a portion thereof (e.g., a binding domain).

65. The DNA vector of any one of paragraphs 1-64, wherein the DNA vector comprises a terminal repeat sequence.

66. An isolated circular DNA vector comprising one or more therapeutic nucleic acids, wherein the DNA vector:
   (a) lacks an origin of replication and/or a drug resistance gene;
   (b) lacks a recombination site; and
   (c) comprises a terminal repeat sequence.

67. The DNA vector of paragraph 66, wherein the therapeutic nucleic acid is an siRNA, shRNA, miRNA, or CRISPRi molecule.

68. The DNA vector of any one of paragraphs 65-67, wherein the terminal repeat sequence is at least 10 bp in length.

69. The DNA vector of any one of paragraphs 65-68, wherein the terminal repeat sequence is a DD element.

70. The DNA vector of any one of paragraphs 1-69, wherein the vector comprises a suicide gene.

71. The DNA vector of any one of paragraphs 1-70, wherein the DNA vector lacks bacterial plasmid DNA.

72. The DNA vector of any one of paragraphs 1-66, wherein the DNA vector comprises one or more unmethylated GATC sequences, one or more unmethylated CCAGG sequences, and/or one or more CCTGG sequences.

73. The DNA vector of any one of paragraph 1-72, wherein the DNA vector:
   (a) lacks an immunogenic bacterial signature;
   (b) lacks an RNA polymerase arrest site; and/or
   (c) is substantially devoid of CpG islands.

74. The DNA vector of any one of paragraphs 1-73, wherein the heterologous gene is greater than 4.5 Kb in length.

75. The DNA vector of any one of paragraphs 1-74, wherein the DNA vector is double stranded.

76. The DNA vector of any one of paragraphs 1-75, wherein the DNA vector is monomeric.

77. The DNA vector of any one of paragraphs 1-76, wherein the DNA vector is supercoiled.

78. A composition comprising a plurality of the DNA vectors of any one of paragraphs 1-77.

79. The composition of paragraph 78, wherein at least 50% of the plurality of the DNA vectors comprises one or more unmethylated GATC sequences, one or more unmethylated CCAGG sequences, and/or one or more CCTGG sequences.

80. An isolated linear DNA molecule comprising a plurality of identical amplicons, wherein each of the plurality of identical amplicons comprises a heterologous gene encoding a therapeutic protein, wherein the DNA molecule lacks:
   (a) an origin of replication and/or a drug resistance gene; and
   (b) a recombination site.

81. An isolated linear DNA molecule comprising a plurality of identical amplicons, wherein each of the plurality of identical amplicons comprises one or more heterologous genes encoding an antigen-binding protein, wherein the DNA molecule lacks:
   (a) an origin of replication and/or a drug resistance gene; and
   (b) a recombination site.

82. An isolated linear DNA molecule comprising a plurality of identical amplicons, wherein each of the plurality of identical amplicons comprises one or more heterologous genes encoding an enzyme, a growth factor, a hormone, an interleukin, an interferon, a cytokine, an anti-apoptosis factor, an anti-diabetic factor, a coagulation factor, an anti-tumor factor, a liver-secreted protein, or a neuroprotective factor, wherein the DNA molecule lacks:
   (a) an origin of replication and/or a drug resistance gene; and
   (b) a recombination site.

83. An isolated linear DNA molecule comprising a plurality of identical amplicons, wherein each of the plurality of identical amplicons comprises one or more heterologous genes associated with a disorder selected from the group consisting of an ocular disorder, a liver disorder, a neurological disorder, an immune disorder, a cancer, a cardiovascular disorder, a blood coagulation disorder, a lysosomal storage disorder, or type 2 diabetes, wherein the DNA molecule lacks:
   (a) an origin of replication and/or a drug resistance gene; and
   (b) a recombination site.

84. An isolated linear DNA molecule comprising a plurality of identical amplicons, wherein each of the plurality of identical amplicons comprises one or more therapeutic nucleic acids, wherein the DNA molecule:
   (a) lacks an origin of replication and/or a drug resistance gene;
   (b) lacks a recombination site; and
   (c) comprises a terminal repeat sequence.

85. The isolated linear DNA molecule of any one of paragraphs 80-84, comprising a restriction enzyme site.

86. The isolated linear DNA molecule of paragraph 85, wherein the restriction enzyme site is positioned between the heterologous gene and a terminal repeat sequence.

87. A method of producing the isolated DNA vector of any one of paragraphs 1-77, the method comprising:
   (i) providing a sample comprising a circular DNA vector comprising an AAV genome, wherein the AAV genome comprises the heterologous gene;
   (ii) amplifying the AAV genome using polymerase-mediated rolling-circle amplification to generate a linear concatamer;
   (iii) digesting the concatamer using a restriction enzyme to generate multiple AAV genomes; and
   (iv) allowing each of the multiple AAV genomes to self-ligate to produce an isolated DNA vector comprising the heterologous gene.

88. The method of paragraph 87, wherein the AAV genome comprises a terminal repeat sequence.

89. The method of paragraph 87 or 88, further comprising column purifying the isolated DNA vector comprising the heterologous gene to purify supercoiled DNA from the isolated DNA vector.

90. A method of producing the isolated DNA vector of any one of paragraphs 1-77, the method comprising:
   (i) providing a sample comprising a circular DNA vector comprising an AAV genome, wherein the AAV genome comprises the heterologous gene and a terminal repeat sequence;
   (ii) amplifying the AAV genome using a first polymerase-mediated rolling-circle amplification to generate a first linear concatamer;
   (iii) digesting the first linear concatamer using a restriction enzyme to generate a first AAV genome;

(iv) cloning the first AAV genome into a plasmid vector;
(v) identifying a plasmid clone comprising a terminal repeat sequence;
(vi) digesting the plasmid clone comprising the terminal repeat sequence to generate a second AAV genome;
(vii) allowing the second AAV genome to self-ligate to produce a circular DNA template;
(viii) amplifying the circular DNA template using second polymerase-mediated rolling-circle amplification to generate a second linear concatamer;
(ix) digesting the second linear concatamer using a restriction enzyme to generate a third AAV genome; and
(x) allowing the third AAV genome to self-ligate to produce an isolated DNA vector comprising the heterologous gene and the terminal repeat sequence.

91. The method of any one of paragraphs 87-90, wherein the polymerase-mediated rolling-circle amplification is isothermal rolling-circle amplification.

92. The method of any one of paragraphs 87-91, wherein the polymerase is Phi29 DNA polymerase.

93. A cell-free method of producing the isolated DNA vector of any one of paragraphs 1-58, the method comprising:
(i) providing a sample comprising a circular DNA vector comprising an AAV genome, wherein the AAV genome comprises the heterologous gene;
(ii) amplifying the AAV genome using polymerase-mediated rolling-circle amplification to generate a linear concatamer;
(iii) digesting the concatamer using a restriction enzyme to generate an AAV genome; and
(iv) allowing the AAV genome to self-ligate to produce the isolated DNA vector comprising the heterologous gene.

94. The method of paragraph 93, further comprising column purifying the isolated DNA vector comprising the heterologous gene to purify supercoiled DNA from the isolated DNA vector.

95. The method of paragraph 93 or 94, wherein the polymerase-mediated rolling-circle amplification is isothermal rolling-circle amplification.

96. The method of any one of paragraphs 93-95, wherein the polymerase is Phi29 DNA polymerase.

97. A method of producing the isolated DNA vector of any one of paragraphs 1-77, the method comprising:
(i) providing a sample comprising a circular DNA vector comprising an AAV genome, wherein the AAV genome comprises the heterologous gene and a DD element;
(ii) amplifying the AAV genome using polymerase-mediated rolling-circle amplification to generate a linear concatamer;
(iii) digesting the concatamer using a restriction enzyme to generate multiple AAV genomes; and
(iv) allowing each of the multiple AAV genomes to self-ligate to produce an isolated DNA vector comprising the heterologous gene and the DD element.

98. A method of producing the isolated DNA vector of any one of paragraphs 1-77, the method comprising:
(i) providing a sample comprising a circular DNA vector comprising an AAV genome, wherein the AAV genome comprises the heterologous gene and a DD element;
(ii) amplifying the AAV genome using a first polymerase-mediated rolling-circle amplification to generate a first linear concatamer;
(iii) digesting the first linear concatamer using a restriction enzyme to generate a first AAV genome;
(iv) cloning the first AAV genome into a plasmid vector;
(v) identifying a plasmid clone comprising a DD element;
(vi) digesting the plasmid clone comprising the DD element to generate a second AAV genome;
(vii) allowing the second AAV genome to self-ligate to produce a circular DNA template;
(viii) amplifying the circular DNA template using second polymerase-mediated rolling-circle amplification to generate a second linear concatamer;
(ix) digesting the second linear concatamer using a restriction enzyme to generate a third AAV genome; and
(x) allowing the third AAV genome to self-ligate to produce an isolated DNA vector comprising the heterologous gene and the DD element.

99. The method of paragraph 97 or 98, wherein the polymerase-mediated rolling-circle amplification is isothermal rolling-circle amplification.

100. The method of any one of paragraphs 97-99, wherein the polymerase is Phi29 DNA polymerase.

101. A cell-free method of producing the isolated DNA vector of any one of paragraphs 1-77, the method comprising:
(i) providing a sample comprising a circular DNA vector comprising an AAV genome, wherein the AAV genome comprises the heterologous gene and a DD element;
(ii) amplifying the AAV genome using polymerase-mediated rolling-circle amplification to generate a linear concatamer;
(iii) digesting the concatamer using a restriction enzyme to generate an AAV genome; and
(iv) allowing the AAV genome to self-ligate to produce a therapeutic DNA vector comprising the heterologous gene and the DD element.

102. The method of paragraph 101, wherein the polymerase-mediated rolling-circle amplification is isothermal rolling-circle amplification.

103. The method of paragraph 101 or 102, wherein the polymerase is Phi29 DNA polymerase.

104. A method of inducing episomal expression of a heterologous gene in a subject in need thereof, the method comprising administering to the subject the isolated DNA vector of any one of paragraphs 1-77 or the composition of paragraph 78 or 79.

105. A method of treating a disorder in a subject, the method comprising administering to the subject the isolated DNA vector of any one of paragraphs 1-77 or the composition of paragraph 78 or 79 in a therapeutically effective amount.

106. The method of paragraph 104 or 105, wherein the isolated DNA vector or the composition is administered repeatedly.

107. The method of any one of paragraphs 104-106, wherein the isolated DNA vector or the composition is administered locally.

108. The method of paragraph 107, wherein the isolated DNA vector or the composition is administered intravitreally.

109. The method of any one of paragraphs 104-108, wherein the disorder is an ocular disorder.

110. The method of paragraph 109, wherein the ocular disorder is a Mendelian-heritable retinal dystrophy.

111. The method of paragraph 110, wherein the ocular disorder is LCA, Stargardt Disease, pseudoxanthoma elasticum, rod cone dystrophy, exudative vitreoretinopathy, Joubert Syndrome, CSNB-1C, age-related macular degeneration, retinitis pigmentosa, stickler syndrome, microcephaly and chorioretinopathy, retinitis pigmentosa, CSNB 2, Usher syndrome, or Wagner syndrome.

112. The method of any one of paragraphs 104-106, wherein the isolated DNA vector or the composition is administered systemically.

113. The method of paragraph 112, wherein the disorder is a coagulation disorder.

114. The method of paragraph 113, wherein the coagulation disorder is hemophilia, von Willebrand's disease, factor XI deficiency, a fibrinogen disorder, or a vitamin K deficiency.

Other embodiments of the technology described herein can be defined according to any of the following numbered paragraphs:

1. An isolated circular DNA vector comprising one or more heterologous genes encoding a therapeutic replacement protein, wherein the DNA vector lacks:
    (a) an origin of replication and/or a drug resistance gene; and
    (b) a recombination site.
2. The DNA vector of paragraph 1, wherein the DNA vector comprises a terminal repeat sequence.
3. The DNA vector of paragraph 2, wherein the terminal repeat sequence is at least 10 bp in length.
4. The DNA vector of any one of paragraphs 1-3, wherein the terminal repeat sequence is a DD element.
5. The DNA vector of any one of paragraphs 1-4, wherein the DNA vector lacks an immunogenic bacterial signature.
6. The DNA vector of any one of paragraphs 1-5, wherein the DNA vector lacks an RNA polymerase arrest site.
7. The DNA vector of any one of paragraphs 1-6, wherein the DNA vector is substantially devoid of CpG islands.
8. The DNA vector of any one of paragraphs 1-7, wherein the therapeutic replacement protein is secreted into blood.
9. The DNA vector of any one of paragraphs 1-8, wherein the one or more heterologous genes comprises a trans-splicing molecule or a portion thereof (e.g., a binding domain).
10. The DNA vector of any one of paragraphs 1-9, wherein the DNA vector comprises one or more unmethylated GATC sequences, one or more unmethylated CCAGG sequences, and/or one or more CCTGG sequences.
11. The DNA vector of any one of paragraphs 1-10, wherein the heterologous gene is greater than 4.5 Kb in length.
12. The DNA vector of any one of paragraphs 1-11, wherein the DNA vector is double stranded.
13. The DNA vector of any one of paragraphs 1-12, wherein the DNA vector is monomeric.
14. The DNA vector of any one of paragraphs 1-13, wherein the DNA vector is supercoiled.
15. The DNA vector of any one of paragraphs 1-14, wherein the therapeutic replacement protein is indicated for treatment of an ocular disorder.
16. The DNA vector of paragraph 15, wherein the ocular disorder is a retinal dystrophy.
17. The DNA vector of paragraph 16, wherein the retinal dystrophy is selected from the group consisting of leber's congenital amaurosis (LCA), Stargardt Disease, pseudoxanthoma elasticum, rod cone dystrophy, exudative vitreoretinopathy, Joubert Syndrome, CSNB-1C, age-related macular degeneration, retinitis pigmentosa, stickler syndrome, microcephaly and chorioretinopathy, retinitis pigmentosa, CSNB 2, Usher syndrome, and Wagner syndrome.
18. The DNA vector of any one of paragraphs 1-14, wherein the therapeutic replacement protein is indicated for treatment of a blood coagulation disorder.
19. The DNA vector of paragraph 18, wherein the blood coagulation disorder is a hemophilia, von Willebrand's disease, factor XI deficiency, a fibrinogen disorder, or a vitamin K deficiency.
20. The DNA vector of paragraph 18, wherein the coagulation disorder is characterized by a mutation in a gene encoding for fibrinogen, prothrombin, factor V, factor VII, factor VIII, factor X, factor XI, factor XIII, or an enzyme involved in posttranslational modifications thereof, or an enzyme involved in vitamin K metabolism.
21. An isolated circular DNA vector comprising one or more heterologous genes encoding an antigen-binding protein, wherein the DNA vector lacks:
    (a) an origin of replication and/or a drug resistance gene; and
    (b) a recombination site.
22. The DNA vector of paragraph 21, wherein the antigen-binding protein is an antibody or an antigen-binding fragment thereof.
23. The DNA vector of paragraph 21 or 22, wherein the antigen-binding protein binds TNF, LT, IFN-α, IFN-γ, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-21, EMAP-II, GM-CSF, EGF, HER2, HER3, FGF, PDGF, BDNF, CNTF, CSF, G-CSF, NGF, PEDF, TGF, VEGF, gonadotropin, insulin-like growth factor, CD2, CD3, CD4, CD8, CD19, CD20, CD25, CD28, CD30, CD40, CD45, CD69, CD80, CD86, CD90, PD-1, PD-L1, amyloid beta, alkaline phosphatase, amyloid protein A, CCR4, folate receptor, mucin 5AC, PCSK-9, phosphatidyl-serine, or sclerostin.
24. The DNA vector of paragraph 22, wherein the antigen-binding protein is a monoclonal antibody, a bispecific antibody, or an antigen-binding fragment.
25. An isolated circular DNA vector comprising one or more heterologous genes encoding an enzyme, a growth factor, a hormone, an interleukin, an interferon, a cytokine, an anti-apoptosis factor, an anti-diabetic factor, a coagulation factor, an anti-tumor factor, a liver-secreted protein, or a neuroprotective factor, wherein the DNA vector lacks:
    (a) an origin of replication and/or a drug resistance gene; and
    (b) a recombination site.
26. The DNA vector of paragraph 25, wherein the growth factor is BDNF, CNTF, CSF, EGF, FGF, G-SCF, M-CSF, GM-CSF, NGF, PDGF, PEDF, TGF, VEGF, gonadotropin, or an insulin-like growth factor.
27. The DNA vector of paragraph 25, wherein the interleukin is IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, or IL-21.
28. The DNA vector of paragraph 25, wherein the interferon is IFN-α or IFN-γ.
29. The DNA vector of paragraph 25, wherein the coagulation factor is factor V, factor VII, factor VIII, factor IX, factor X, factor XI, factor XII, factor XIII, or von Willebrand factor.
30. The DNA vector of paragraph 25, wherein the neuroprotective factor is selected from the group consisting of a neurotrophin, Kifap3, Bcl-xl, Crmp1, Chk.beta., CALM2, Caly, NPG11, NPT1, Eef1a1, Dhps, Cd151, Morf4l2, CTGF, LDH-A, Atl1, NPT2, Ehd3, Cox5b, Tuba1a, gamma-actin, Rpsa, NPG3, NPG4, NPG5, NPG6, NPG7, NPG8, NPG9, and NPG10.
31. The DNA vector of paragraph 30, wherein the neurotrophin is selected from the group consisting of NGF, BDNF, NT-3, NT-4, and CNTF.

32. An isolated circular DNA vector comprising one or more heterologous genes associated with a disorder selected from the group consisting of an ocular disorder, a liver disorder, a neurological disorder, an immune disorder, a cancer, a cardiovascular disorder, a blood coagulation disorder, a lysosomal storage disorder, or type 2 diabetes, wherein the DNA vector lacks:

(a) an origin of replication and/or a drug resistance gene; and (b) a recombination site.

33. The DNA vector of paragraph 32, wherein the disorder is an ocular disorder that is a retinal dystrophy.

34. The DNA vector of paragraph 33, wherein the disorder is a Mendelian-heritable retinal dystrophy.

35. The DNA vector of paragraph 33, wherein the retinal dystrophy is selected from the group consisting of leber's congenital amaurosis (LCA), Stargardt Disease, pseudoxanthoma elasticum, rod cone dystrophy, exudative vitreoretinopathy, Joubert Syndrome, CSNB-1C, age-related macular degeneration, retinitis pigmentosa, stickler syndrome, microcephaly and chorioretinopathy, retinitis pigmentosa, CSNB 2, Usher syndrome, and Wagner syndrome.

36. The DNA vector of paragraph 32, wherein the coagulation disorder is a hemophilia, von Willebrand's disease, factor XI deficiency, a fibrinogen disorder, or a vitamin K deficiency.

37. The DNA vector of paragraph 32, wherein the coagulation disorder is characterized by a mutation in a gene encoding for fibrinogen, prothrombin, factor V, factor VII, factor VIII, factor X, factor XI, factor XIII, or an enzyme involved in posttranslational modifications thereof, or an enzyme involved in vitamin K metabolism.

38. The DNA vector of paragraph 32 or 37, wherein the coagulation disorder is characterized by a mutation in FGA, FGB, FGG, F2, F5, F7, F10, F11, F13A, F13B, LMAN1, MCFD2, GGCX, or VKORC1.

39. The DNA vector of paragraph 32, wherein the neurological disorder is a neurodegenerative disease.

40. The DNA vector of paragraph 39, wherein the neurodegenerative disease is selected from the group consisting of Alzheimer's disease, Parkinson's disease, and multiple sclerosis.

41. The DNA vector of paragraph 39, wherein the neurodegenerative disease is an autoimmune disease of the central nervous system (CNS).

42. The DNA vector of paragraph 41, wherein the autoimmune disease of the CNS is multiple sclerosis, encephalomyelitis, a paraneoplastic syndrome, autoimmune inner ear disease, or opsoclonus myoclonus syndrome.

43. The DNA vector of paragraph 32, wherein the neurological disorder is a cerebral infarction, spinal cord injury, central nervous system disorder, a neuropsychiatric disorder, or a channelopathy.

44. The DNA vector of paragraph 43, wherein the channelopathy is epilepsy or migraine.

45. The DNA vector of paragraph 32, wherein the neurological disorder is an anxiety disorder, a mood disorder, a childhood disorder, a cognitive disorder, schizophrenia, a substance related disorder, or an eating disorder.

46. The DNA vector of paragraph 32, wherein the neurological disorder is a symptom of a cerebral infarction, stroke, traumatic brain injury, or spinal cord injury.

47. The DNA vector of paragraph 32, wherein the lysosomal storage disorder is selected from the group consisting of Tay-Sachs disease, Gaucher disease, Fabry disease, Pompe disease, Niemann-Pick disease, and mucopolysaccharidosis (MPS).

48. The DNA vector of paragraph 32, wherein the cardiovascular disorder is a degenerative heart disease, a coronary artery disease, an ischemia, angina pectoris, an acute coronary syndrome, a peripheral vascular disease, a peripheral arterial disease, a cerebrovascular disease, or atherosclerosis.

49. The DNA vector of paragraph 32, wherein the cardiovascular disorder is a degenerative heart disease selected from the group consisting of an ischemic cardiomyopathy, a conduction disease, and a congenital defect.

50. The DNA vector of paragraph 32, wherein the immune disorder is an autoimmune disorder.

51. The DNA vector of paragraph 50, wherein the autoimmune disorder is type 1 diabetes, multiple sclerosis, rheumatoid arthritis, lupus, encephalomyelitis, a paraneoplastic syndrome, autoimmune inner ear disease, or opsoclonus myoclonus syndrome, autoimmune hepatitis, uveitis, autoimmune retinopathy, neuromyelitis optica, psoriatic arthritis, psoriasis, myasthenia gravis, chronic Lyme disease, celiac disease, chronic inflammatory demyelinating polyneuropathy, peripheral neuropathy, fibromyalgia, Hashimoto's thyroiditis, ulcerative colitis, or Kawasaki disease.

52. The DNA vector of paragraph 32, wherein the disease is a liver disease selected from the group consisting of hepatitis, Alagille syndrome, biliary atresia, liver cancer, cirrhosis, a cystic disease, Caroli's syndrome, congenital hepatic fibrosis, fatty liver, galactosemia, primary sclerosing cholangitis, tyrosinemia, glycogen storage disease, Wilson's disease, and an endocrine deficiency.

53. The DNA vector of paragraph 52, wherein the liver disease is a liver cancer selected from the group consisting of a hepatocellular hyperplasia, a hepatocellular adenomas, a focal nodular hyperplasia, or a hepatocellular carcinoma.

54. The DNA vector of paragraph 33, wherein the cancer is a blood cancer or a solid tissue cancer.

55. The DNA vector of paragraph 54, wherein the blood cancer is acute lymphoblastic leukemia, acute myeloblastic leukemia, chromic myelogenous leukemia, Hodgkin's disease, multiple myeloma, and non-Hodgkin's lymphoma.

56. The DNA vector of paragraph 54, wherein the solid tissue cancer is a liver cancer, kidney cancer, a breast cancer, a gastric cancer, an esophageal cancer, a stomach cancer, an intestinal cancer, a colorectal cancer, a bladder cancer, a head and neck cancer, a skin cancer, or a brain cancer.

57. The DNA vector of any one of paragraphs 1-56, wherein the disorder is a recessively inherited disorder.

58. The DNA vector of any one of paragraphs 1-57, wherein the heterologous gene is expressible in a target cell selected from the group consisting of a liver cell, a retinal cell, a stem cell, a neural cell, a muscle cell, or a blood cell.

59. The DNA vector of any one of paragraphs 1-58, wherein the heterologous gene is expressible in a post-mitotic target cell.

60. The DNA vector of paragraph 58 or 59, wherein the target cell is a neural cell selected from the group consisting of a neuron, an astrocyte, an oligodendrocyte, and a Schwann cell.

61. The DNA vector of any one of paragraphs 1-60, wherein the therapeutic protein is secreted into blood.

62. The DNA vector of any one of paragraphs 1-61, wherein the DNA vector comprises a promoter sequence upstream of the one or more heterologous genes.

63. The DNA vector of any one of paragraphs 1-62, wherein the DNA vector comprises a polyadenylation site downstream of the one or more heterologous genes.

64. The DNA vector of any one of paragraphs 1-63, wherein the one or more heterologous genes comprises a trans-splicing molecule or a portion thereof (e.g., a binding domain).

65. The DNA vector of any one of paragraphs 1-64, wherein the DNA vector comprises a terminal repeat sequence.

66. An isolated circular DNA vector comprising one or more therapeutic nucleic acids, wherein the DNA vector:
 (a) lacks an origin of replication and/or a drug resistance gene;
 (b) lacks a recombination site; and
 (c) comprises a terminal repeat sequence.

67. The DNA vector of paragraph 66, wherein the therapeutic nucleic acid is an siRNA, shRNA, miRNA, or CRISPRi molecule.

68. The DNA vector of any one of paragraphs 65-67, wherein the terminal repeat sequence is at least 10 bp in length.

69. The DNA vector of any one of paragraphs 65-68, wherein the terminal repeat sequence is a DD element.

70. The DNA vector of any one of paragraphs 1-69, wherein the vector comprises a suicide gene.

71. The DNA vector of any one of paragraphs 1-70, wherein the DNA vector lacks bacterial plasmid DNA.

72. The DNA vector of any one of paragraphs 1-66, wherein the DNA vector comprises one or more unmethylated GATC sequences, one or more unmethylated CCAGG sequences, and/or one or more CCTGG sequences.

73. The DNA vector of any one of paragraph 1-72, wherein the DNA vector:
 (a) lacks an immunogenic bacterial signature;
 (b) lacks an RNA polymerase arrest site; and/or
 (c) is substantially devoid of CpG islands.

74. The DNA vector of any one of paragraphs 1-73, wherein the heterologous gene is greater than 4.5 Kb in length.

75. The DNA vector of any one of paragraphs 1-74, wherein the DNA vector is double stranded.

76. The DNA vector of any one of paragraphs 1-75, wherein the DNA vector is monomeric.

77. The DNA vector of any one of paragraphs 1-76, wherein the DNA vector is supercoiled.

78. A composition comprising a plurality of the DNA vectors of any one of paragraphs 1-77.

79. The composition of paragraph 78, wherein at least 50% of the plurality of the DNA vectors comprises one or more unmethylated GATC sequences, one or more unmethylated CCAGG sequences, and/or one or more CCTGG sequences.

80. An isolated linear DNA molecule comprising a plurality of identical amplicons, wherein each of the plurality of identical amplicons comprises a heterologous gene encoding a therapeutic protein, wherein the DNA molecule lacks:
 (a) an origin of replication and/or a drug resistance gene; and
 (b) a recombination site.

81. An isolated linear DNA molecule comprising a plurality of identical amplicons, wherein each of the plurality of identical amplicons comprises one or more heterologous genes encoding an antigen-binding protein, wherein the DNA molecule lacks:
 (a) an origin of replication and/or a drug resistance gene; and
 (b) a recombination site.

82. An isolated linear DNA molecule comprising a plurality of identical amplicons, wherein each of the plurality of identical amplicons comprises one or more heterologous genes encoding an enzyme, a growth factor, a hormone, an interleukin, an interferon, a cytokine, an anti-apoptosis factor, an anti-diabetic factor, a coagulation factor, an anti-tumor factor, a liver-secreted protein, or a neuroprotective factor, wherein the DNA molecule lacks:
 (a) an origin of replication and/or a drug resistance gene; and
 (b) a recombination site.

83. An isolated linear DNA molecule comprising a plurality of identical amplicons, wherein each of the plurality of identical amplicons comprises one or more heterologous genes associated with a disorder selected from the group consisting of an ocular disorder, a liver disorder, a neurological disorder, an immune disorder, a cancer, a cardiovascular disorder, a blood coagulation disorder, a lysosomal storage disorder, or type 2 diabetes, wherein the DNA molecule lacks:
 (a) an origin of replication and/or a drug resistance gene; and
 (b) a recombination site.

84. An isolated linear DNA molecule comprising a plurality of identical amplicons, wherein each of the plurality of identical amplicons comprises one or more therapeutic nucleic acids, wherein the DNA molecule:
 (a) lacks an origin of replication and/or a drug resistance gene;
 (b) lacks a recombination site; and
 (c) comprises a terminal repeat sequence.

85. The isolated linear DNA molecule of any one of paragraphs 80-84, comprising a restriction enzyme site.

86. The isolated linear DNA molecule of paragraph 85, wherein the restriction enzyme site is positioned between the heterologous gene and a terminal repeat sequence.

87. A method of producing the isolated DNA vector of any one of paragraphs 1-77, the method comprising:
 (i) providing a sample comprising a circular DNA vector comprising an AAV genome, wherein the AAV genome comprises the heterologous gene;
 (ii) amplifying the AAV genome using polymerase-mediated rolling-circle amplification to generate a linear concatamer;
 (iii) digesting the concatamer using a restriction enzyme to generate multiple AAV genomes; and
 (iv) allowing each of the multiple AAV genomes to self-ligate to produce an isolated DNA vector comprising the heterologous gene.

88. The method of paragraph 87, wherein the AAV genome comprises a terminal repeat sequence.

89. The method of paragraph 87 or 88, further comprising column purifying the isolated DNA vector comprising the heterologous gene to purify supercoiled DNA from the isolated DNA vector.

90. A method of producing the isolated DNA vector of any one of paragraphs 1-77, the method comprising:
 (i) providing a sample comprising a circular DNA vector comprising an AAV genome, wherein the AAV genome comprises the heterologous gene and a terminal repeat sequence;
 (ii) amplifying the AAV genome using a first polymerase-mediated rolling-circle amplification to generate a first linear concatamer;
 (iii) digesting the first linear concatamer using a restriction enzyme to generate a first AAV genome;
 (iv) cloning the first AAV genome into a plasmid vector;
 (v) identifying a plasmid clone comprising a terminal repeat sequence;

(vi) digesting the plasmid clone comprising the terminal repeat sequence to generate a second AAV genome;
(vii) allowing the second AAV genome to self-ligate to produce a circular DNA template;
(viii) amplifying the circular DNA template using second polymerase-mediated rolling-circle amplification to generate a second linear concatamer;
(ix) digesting the second linear concatamer using a restriction enzyme to generate a third AAV genome; and
(x) allowing the third AAV genome to self-ligate to produce an isolated DNA vector comprising the heterologous gene and the terminal repeat sequence.

91. The method of any one of paragraphs 87-90, wherein the polymerase-mediated rolling-circle amplification is isothermal rolling-circle amplification.

92. The method of any one of paragraphs 87-91, wherein the polymerase is Phi29 DNA polymerase.

93. A cell-free method of producing the isolated DNA vector of any one of paragraphs 1-58, the method comprising:
(i) providing a sample comprising a circular DNA vector comprising an AAV genome, wherein the AAV genome comprises the heterologous gene;
(ii) amplifying the AAV genome using polymerase-mediated rolling-circle amplification to generate a linear concatamer;
(iii) digesting the concatamer using a restriction enzyme to generate an AAV genome; and
(iv) allowing the AAV genome to self-ligate to produce the isolated DNA vector comprising the heterologous gene.

94. The method of paragraph 93, further comprising column purifying the isolated DNA vector comprising the heterologous gene to purify supercoiled DNA from the isolated DNA vector.

95. The method of paragraph 93 or 94, wherein the polymerase-mediated rolling-circle amplification is isothermal rolling-circle amplification.

96. The method of any one of paragraphs 93-95, wherein the polymerase is Phi29 DNA polymerase.

97. A method of producing the isolated DNA vector of any one of paragraphs 1-77, the method comprising:
(i) providing a sample comprising a circular DNA vector comprising an AAV genome, wherein the AAV genome comprises the heterologous gene and a DD element;
(ii) amplifying the AAV genome using polymerase-mediated rolling-circle amplification to generate a linear concatamer;
(iii) digesting the concatamer using a restriction enzyme to generate multiple AAV genomes; and
(iv) allowing each of the multiple AAV genomes to self-ligate to produce an isolated DNA vector comprising the heterologous gene and the DD element.

98. A method of producing the isolated DNA vector of any one of paragraphs 1-77, the method comprising:
(i) providing a sample comprising a circular DNA vector comprising an AAV genome, wherein the AAV genome comprises the heterologous gene and a DD element;
(ii) amplifying the AAV genome using a first polymerase-mediated rolling-circle amplification to generate a first linear concatamer;
(iii) digesting the first linear concatamer using a restriction enzyme to generate a first AAV genome;
(iv) cloning the first AAV genome into a plasmid vector;
(v) identifying a plasmid clone comprising a DD element;
(vi) digesting the plasmid clone comprising the DD element to generate a second AAV genome;
(vii) allowing the second AAV genome to self-ligate to produce a circular DNA template;
(viii) amplifying the circular DNA template using second polymerase-mediated rolling-circle amplification to generate a second linear concatamer;
(ix) digesting the second linear concatamer using a restriction enzyme to generate a third AAV genome; and
(x) allowing the third AAV genome to self-ligate to produce an isolated DNA vector comprising the heterologous gene and the DD element.

99. The method of paragraph 97 or 98, wherein the polymerase-mediated rolling-circle amplification is isothermal rolling-circle amplification.

100. The method of any one of paragraphs 97-99, wherein the polymerase is Phi29 DNA polymerase.

101. A cell-free method of producing the isolated DNA vector of any one of paragraphs 1-77, the method comprising:
(i) providing a sample comprising a circular DNA vector comprising an AAV genome, wherein the AAV genome comprises the heterologous gene and a DD element;
(ii) amplifying the AAV genome using polymerase-mediated rolling-circle amplification to generate a linear concatamer;
(iii) digesting the concatamer using a restriction enzyme to generate an AAV genome; and
(iv) allowing the AAV genome to self-ligate to produce a therapeutic DNA vector comprising the heterologous gene and the DD element.

102. The method of paragraph 101, wherein the polymerase-mediated rolling-circle amplification is isothermal rolling-circle amplification.

103. The method of paragraph 101 or 102, wherein the polymerase is Phi29 DNA polymerase.

104. A method of inducing episomal expression of a heterologous gene in a subject in need thereof, the method comprising administering to the subject the isolated DNA vector of any one of paragraphs 1-77 or the composition of paragraph 78 or 79.

105. A method of treating a disorder in a subject, the method comprising administering to the subject the isolated DNA vector of any one of paragraphs 1-77 or the composition of paragraph 78 or 79 in a therapeutically effective amount.

106. The method of paragraph 104 or 105, wherein the isolated DNA vector or the composition is administered repeatedly.

107. The method of any one of paragraphs 104-106, wherein the isolated DNA vector or the composition is administered locally.

108. The method of paragraph 107, wherein the isolated DNA vector or the composition is administered intravitreally.

109. The method of any one of paragraphs 104-108, wherein the disorder is an ocular disorder.

110. The method of paragraph 109, wherein the ocular disorder is a Mendelian-heritable retinal dystrophy.

111. The method of paragraph 110, wherein the ocular disorder is LCA, Stargardt Disease, pseudoxanthoma elasticum, rod cone dystrophy, exudative vitreoretinopathy, Joubert Syndrome, CSNB-1C, age-related macular degeneration, retinitis pigmentosa, stickler syndrome, microcephaly and chorioretinopathy, retinitis pigmentosa, CSNB 2, Usher syndrome, or Wagner syndrome.

Other embodiments of the technology described herein can be defined according to any of the following numbered paragraphs: 1. An isolated circular DNA vector comprising one or more heterologous genes encoding a therapeutic replacement protein, wherein the DNA vector lacks:

(a) an origin of replication and/or a drug resistance gene; and (b) a recombination site.

2. The DNA vector of paragraph 1, wherein the DNA vector comprises a terminal repeat sequence.

3. The DNA vector of paragraph 2, wherein the terminal repeat sequence is at least 10 bp in length.

4. The DNA vector of any one of paragraphs 1-3, wherein the terminal repeat sequence is a DD element.

5. The DNA vector of any one of paragraphs 1-4, wherein the DNA vector lacks an immunogenic bacterial signature.

6. The DNA vector of any one of paragraphs 1-5, wherein the DNA vector lacks an RNA polymerase arrest site.

7. The DNA vector of any one of paragraphs 1-6, wherein the DNA vector comprises a promoter which is substantially devoid of CpG islands.

8. The DNA vector of any one of paragraphs 1-7, wherein the therapeutic replacement protein is secreted into blood.

9. The DNA vector of any one of paragraphs 1-8, wherein the one or more heterologous genes comprises a trans-splicing molecule or a portion thereof (e.g., a binding domain).

10. The DNA vector of any one of paragraphs 1-9, wherein the DNA vector is double stranded.

11. The DNA vector of any one of paragraphs 1-10, wherein the DNA vector is monomeric.

12. The DNA vector of any one of paragraphs 1-11, wherein the DNA vector is covalently closed.

13. The DNA vector of any one of paragraphs 1-12, wherein the DNA vector is supercoiled.

14, The DNA vector of any one of paragraphs 1-13, herein the DNA vector is covalently closed and supercoiled.

15. The DNA vector of any one of paragraphs 1-14, wherein the therapeutic replacement protein is indicated for treatment of an ocular disorder.

16. The DNA vector of paragraph 15, wherein the ocular disorder is a retinal dystrophy.

17. The DNA vector of paragraph 16, wherein the retinal dystrophy is selected from the group consisting of leber's congenital amaurosis (LCA), Stargardt Disease, pseudoxanthoma elasticum, rod cone dystrophy, exudative vitreoretinopathy, Joubert Syndrome, CSNB-1C, age-related macular degeneration, retinitis pigmentosa, stickler syndrome, microcephaly and chorioretinopathy, retinitis pigmentosa, CSNB 2, Usher syndrome, and Wagner syndrome.

18. The DNA vector of any one of paragraphs 1-14, wherein the therapeutic replacement protein is indicated for treatment of a blood coagulation disorder.

19. The DNA vector of paragraph 18, wherein the blood coagulation disorder is a hemophilia, von Willebrand's disease, factor XI deficiency, a fibrinogen disorder, or a vitamin K deficiency.

20. The DNA vector of paragraph 18, wherein the blood coagulation disorder is characterized by a mutation in a gene encoding for fibrinogen, prothrombin, factor V, factor VII, factor VIII, factor X, factor XI, factor XIII, or an enzyme involved in posttranslational modifications thereof, or an enzyme involved in vitamin K metabolism.

21. An isolated circular DNA vector comprising one or more heterologous genes encoding an antigen-binding protein, wherein the DNA vector lacks:

(a) an origin of replication and/or a drug resistance gene; and (b) a recombination site.

22. The DNA vector of paragraph 21, wherein the antigen-binding protein is an antibody or an antigen-binding fragment thereof.

23. The DNA vector of paragraph 21 or 22, wherein the antigen-binding protein binds TNF, LT, IFN-α, IFN-γ, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-21, EMAP-II, GM-CSF, EGF, HER2, HER3, FGF, PDGF, BDNF, CNTF, CSF, G-CSF, NGF, PEDF, TGF, VEGF, gonadotropin, insulin-like growth factor, CD2, CD3, CD4, CD8, CD19, CD20, CD25, CD28, CD30, CD40, CD45, CD69, CD80, CD86, CD90, PD-1, PD-L1, amyloid beta, alkaline phosphatase, amyloid protein A, CCR4, folate receptor, mucin 5AC, PCSK-9, phosphatidyl-serine, or sclerostin.

24. The DNA vector of paragraph 22, wherein the antigen-binding protein is a monoclonal antibody, a bispecific antibody, or an antigen-binding fragment.

25. The DNA vector of paragraph 1, wherein the DNA vector comprises one or more unmethylated GATC sequences, one or more unmethylated CCAGG sequences, and/or one or more CCTGG sequences.

26. The DNA vector of paragraph 1, wherein the heterologous gene is greater than 4.5 Kb in length.

27. An isolated circular DNA vector comprising one or more heterologous genes encoding an enzyme, a growth factor, a hormone, an interleukin, an interferon, a cytokine, an anti-apoptosis factor, an anti-diabetic factor, a coagulation factor, an anti-tumor factor, a liver-secreted protein, or a neuroprotective factor, wherein the DNA vector lacks:

(a) an origin of replication and/or a drug resistance gene; and (b) a recombination site.

28. The DNA vector of paragraph 27, wherein the enzyme is an epigenetic regulator.

29. The DNA vector of paragraph 28, wherein the epigenetic regulator is a histone methyltransferase, a histone demethylase, a histone acetylase, a DNA methyltransferase, or a DNA demethylase.

30. The DNA vector of paragraph 27, wherein the growth factor is BDNF, CNTF, CSF, EGF, FGF, G-SCF, M-CSF, GM-CSF, NGF, PDGF, PEDF, TGF, VEGF, gonadotropin, or an insulin-like growth factor.

31. The DNA vector of paragraph 27, wherein the interleukin is IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, or IL-21.

32. The DNA vector of paragraph 27, wherein the interferon is IFN-α or IFN-γ.

33. The DNA vector of paragraph 27, wherein the coagulation factor is factor V, factor VII, factor VIII, factor IX, factor X, factor XI, factor XII, factor XIII, or von Willebrand factor.

34. The DNA vector of paragraph 27, wherein the neuroprotective factor is selected from the group consisting of a neurotrophin, Kifap3, Bcl-xl, Crmp1, Chk.beta., CALM2, Caly, NPG11, NPT1, Eef1a1, Dhps, Cd151, Morf412, CTGF, LDH-A, Atl1, NPT2, Ehd3, Cox5b, Tuba1a, gamma-actin, Rpsa, NPG3, NPG4, NPG5, NPG6, NPG7, NPG8, NPG9, and NPG10.

35. The DNA vector of paragraph 34, wherein the neurotrophin is selected from the group consisting of NGF, BDNF, NT-3, NT-4, and CNTF.

36. An isolated circular DNA vector comprising one or more heterologous genes associated with a disorder selected from the group consisting of an ocular disorder, a liver disorder, a neurological disorder, an immune disorder, a cancer, a cardiovascular disorder, a blood coagulation disorder, a lysosomal storage disorder, or type 2 diabetes, wherein the DNA vector lacks:

(a) an origin of replication and/or a drug resistance gene; and (b) a recombination site.

37. The DNA vector of paragraph 36, wherein the disorder is an ocular disorder that is a retinal dystrophy.

38. The DNA vector of paragraph 37, wherein the disorder is a Mendelian-heritable retinal dystrophy.

39. The DNA vector of paragraph 38, wherein the Mendelian-heritable retinal dystrophy is selected from the group consisting of leber's congenital amaurosis (LCA), Stargardt Disease, pseudoxanthoma elasticum, rod cone dystrophy, exudative vitreoretinopathy, Joubert Syndrome, CSNB-1C, age-related macular degeneration, retinitis pigmentosa, stickler syndrome, microcephaly and chorioretinopathy, retinitis pigmentosa, CSNB 2, Usher syndrome, and Wagner syndrome.

40. The DNA vector of paragraph 36, wherein the disorder is a cancer and the heterologous gene is CD40, CD40L, CD46, XCL1, MDA-7, IL-12, IL-24, or OPCML (opioid binding protein/cell adhesion molecule).

41. The DNA vector of paragraph 36, wherein the disorder is a cancer and the heterologous gene is a tumor suppressor gene.

42. The DNA vector of paragraph 41, wherein the tumor suppressor gene is a gene encoding an intracellular protein.

43. The DNA vector of paragraph 41, wherein the tumor suppressor gene is a gene encoding a receptor or signal transducer for a secreted hormone or developmental signal that inhibits cell proliferation.

44. The DNA vector of paragraph 41, wherein the tumor suppressor gene is a gene that encodes a checkpoint control protein.

45. The DNA vector of paragraph 41, wherein the tumor suppressor gene is a gene that encodes a pro-apoptotic protein.

46. The DNA vector of paragraph 41, wherein the tumor suppressor gene is a gene that encodes a DNA repair protein.

47. The DNA vector of paragraph 36, wherein the coagulation disorder is a hemophilia, von Willebrand's disease, factor XI deficiency, a fibrinogen disorder, or a vitamin K deficiency.

48. The DNA vector of paragraph 36, wherein the coagulation disorder is characterized by a mutation in a gene encoding for fibrinogen, prothrombin, factor V, factor VII, factor VIII, factor X, factor XI, factor XIII, or an enzyme involved in posttranslational modifications thereof, or an enzyme involved in vitamin K metabolism.

49. The DNA vector of paragraph 36 or 48, wherein the coagulation disorder is characterized by a mutation in FGA, FGB, FGG, F2, F5, F7, F10, F11, F13A, F13B, LMAN1, MCFD2, GGCX, or VKORC1.

50. The DNA vector of paragraph 36, wherein the neurological disorder is a neurodegenerative disease.

51. The DNA vector of paragraph 50, wherein the neurodegenerative disease is selected from the group consisting of Alzheimer's disease, Parkinson's disease, and multiple sclerosis.

52. The DNA vector of paragraph 50, wherein the neurodegenerative disease is an autoimmune disease of the central nervous system (CNS).

53. The DNA vector of paragraph 52, wherein the autoimmune disease of the CNS is multiple sclerosis, encephalomyelitis, a paraneoplastic syndrome, autoimmune inner ear disease, or opsoclonus myoclonus syndrome.

54. The DNA vector of paragraph 36, wherein the neurological disorder is a cerebral infarction, spinal cord injury, central nervous system disorder, a neuropsychiatric disorder, or a channelopathy.

55. The DNA vector of paragraph 54, wherein the channelopathy is epilepsy or migraine.

56. The DNA vector of paragraph 36, wherein the neurological disorder is an anxiety disorder, a mood disorder, a childhood disorder, a cognitive disorder, schizophrenia, a substance related disorder, or an eating disorder.

57. The DNA vector of paragraph 36, wherein the neurological disorder is a symptom of a cerebral infarction, stroke, traumatic brain injury, or spinal cord injury.

58. The DNA vector of paragraph 36, wherein the lysosomal storage disorder is selected from the group consisting of Tay-Sachs disease, Gaucher disease, Fabry disease, Pompe disease, Niemann-Pick disease, and mucopolysaccharidosis (MPS).

59. The DNA vector of paragraph 36, wherein the cardiovascular disorder is a degenerative heart disease, a coronary artery disease, an ischemia, angina pectoris, an acute coronary syndrome, a peripheral vascular disease, a peripheral arterial disease, a cerebrovascular disease, or atherosclerosis.

60. The DNA vector of paragraph 36, wherein the cardiovascular disorder is a degenerative heart disease selected from the group consisting of an ischemic cardiomyopathy, a conduction disease, and a congenital defect.

61. The DNA vector of paragraph 36, wherein the immune disorder is an autoimmune disorder.

62. The DNA vector of paragraph 61, wherein the autoimmune disorder is type 1 diabetes, multiple sclerosis, rheumatoid arthritis, lupus, encephalomyelitis, a paraneoplastic syndrome, autoimmune inner ear disease, or opsoclonus myoclonus syndrome, autoimmune hepatitis, uveitis, autoimmune retinopathy, neuromyelitis optica, psoriatic arthritis, psoriasis, myasthenia gravis, chronic Lyme disease, celiac disease, chronic inflammatory demyelinating polyneuropathy, peripheral neuropathy, fibromyalgia, Hashimoto's thyroiditis, ulcerative colitis, or Kawasaki disease.

63. The DNA vector of paragraph 36, wherein the disease is a liver disease selected from the group consisting of hepatitis, Alagille syndrome, biliary atresia, liver cancer, cirrhosis, a cystic disease, Caroli's syndrome, congenital hepatic fibrosis, fatty liver, galactosemia, primary sclerosing cholangitis, tyrosinemia, glycogen storage disease, Wilson's disease, and an endocrine deficiency.

64. The DNA vector of paragraph 63, wherein the liver disease is a liver cancer selected from the group consisting of a hepatocellular hyperplasia, a hepatocellular adenomas, a focal nodular hyperplasia, or a hepatocellular carcinoma.

65. The DNA vector of paragraph 36, wherein the cancer is a blood cancer or a solid tissue cancer.

66. The DNA vector of paragraph 65, wherein the blood cancer is acute lymphoblastic leukemia, acute myeloblastic leukemia, chromic myelogenous leukemia, Hodgkin's disease, multiple myeloma, and non-Hodgkin's lymphoma.

67. The DNA vector of paragraph 65, wherein the solid tissue cancer is a liver cancer, kidney cancer, a breast cancer, a prostate cancer, a gastric cancer, an esophageal cancer, a stomach cancer, an intestinal cancer, a colorectal cancer, a bladder cancer, a head and neck cancer, a skin cancer, or a brain cancer.

68. The DNA vector of paragraph 36, wherein the heterologous gene encodes a transcription factor.

69. The DNA vector of paragraph 36, wherein the transcription factor is TSHZ2, HOXA2, MEIS2, HOXA3, HAND2, HOXA5, TBX18, PEG3, GLI2, CLOCK, HNF4A, VHL/HIF, WT-1, GSK-3, SPINT2, SMAD2, SMAD3, or SMAD4.

70. The DNA vector of any one of paragraphs 1-69, wherein the disorder is a recessively inherited disorder.

71. The DNA vector of any one of paragraphs 1-70, wherein the heterologous gene is expressible in a target cell selected from the group consisting of a liver cell, a retinal cell, a stem cell, a neural cell, a muscle cell, or a blood cell.

72. The DNA vector of any one of paragraphs 1-71, wherein the heterologous gene is expressible in a post-mitotic target cell.

73. The DNA vector of paragraph 71 or 72, wherein the target cell is a neural cell selected from the group consisting of a neuron, an astrocyte, an oligodendrocyte, and a Schwann cell.

74. The DNA vector of any one of paragraphs 1-73, wherein the therapeutic protein is secreted into blood.

75. The DNA vector of any one of paragraphs 1-74, wherein the DNA vector comprises a promoter sequence upstream of the one or more heterologous genes.

76. The DNA vector of any one of paragraphs 1-75, wherein the DNA vector comprises a polyadenylation site downstream of the one or more heterologous genes.

77. The DNA vector of any one of paragraphs 1-76, wherein the one or more heterologous genes comprises a trans-splicing molecule or a portion thereof (e.g., a binding domain).

78. The DNA vector of any one of paragraphs 1-77, wherein the DNA vector comprises a terminal repeat sequence.

79. An isolated circular DNA vector comprising one or more therapeutic nucleic acids, wherein the DNA vector:
    (a) lacks an origin of replication and/or a drug resistance gene;
    (b) lacks a recombination site; and
    (c) comprises a terminal repeat sequence.

80. The DNA vector of 79 66, wherein the therapeutic nucleic acid is an siRNA, shRNA, miRNA, or CRISPRi molecule.

81. The DNA vector of paragraph 79 or 80, wherein the terminal repeat sequence is at least 10 bp in length.

82. The DNA vector of any one of paragraphs 79-81, wherein the terminal repeat sequence is a DD element.

83. The DNA vector of any one of paragraphs 1-82, wherein the DNA vector comprises a suicide gene.

84. The DNA vector of any one of paragraphs 1-83, wherein the DNA vector lacks bacterial plasmid DNA.

85. The DNA vector of any one of paragraphs 1-79, wherein the DNA vector comprises one or more unmethylated GATC sequences, one or more unmethylated CCAGG sequences, and/or one or more CCTGG sequences.

86. The DNA vector of any one of paragraph 1-85, wherein the DNA vector:
    (a) lacks an immunogenic bacterial signature;
    (b) lacks an RNA polymerase arrest site; and/or
    (c) is substantially devoid of CpG islands.

87. The DNA vector of any one of paragraphs 1-86, wherein the heterologous gene is greater than 4.5 Kb in length.

88. The DNA vector of any one of paragraphs 1-87, wherein the DNA vector is double stranded.

89. The DNA vector of any one of paragraphs 1-88, wherein the DNA vector is monomeric.

90. The DNA vector of any one of paragraphs 1-89, wherein the DNA vector is supercoiled.

91. A composition comprising a plurality of the DNA vectors of any one of paragraphs 1-90.

92. The composition of paragraph 91, wherein at least 50% of the plurality of the DNA vectors comprises one or more unmethylated GATC sequences, one or more unmethylated CCAGG sequences, and/or one or more CCTGG sequences.

93. An isolated linear DNA molecule comprising a plurality of identical amplicons, wherein each of the plurality of identical amplicons comprises a heterologous gene encoding a therapeutic protein, wherein the DNA molecule lacks:
    (a) an origin of replication and/or a drug resistance gene; and
    (b) a recombination site.

94. An isolated linear DNA molecule comprising a plurality of identical amplicons, wherein each of the plurality of identical amplicons comprises one or more heterologous genes encoding an antigen-binding protein, wherein the DNA molecule lacks:
    (a) an origin of replication and/or a drug resistance gene; and
    (b) a recombination site.

95. An isolated linear DNA molecule comprising a plurality of identical amplicons, wherein each of the plurality of identical amplicons comprises one or more heterologous genes encoding an enzyme, a growth factor, a hormone, an interleukin, an interferon, a cytokine, an anti-apoptosis factor, an anti-diabetic factor, a coagulation factor, an anti-tumor factor, a liver-secreted protein, or a neuroprotective factor, wherein the DNA molecule lacks:
    (a) an origin of replication and/or a drug resistance gene; and
    (b) a recombination site.

96. An isolated linear DNA molecule comprising a plurality of identical amplicons, wherein each of the plurality of identical amplicons comprises one or more heterologous genes associated with a disorder selected from the group consisting of an ocular disorder, a liver disorder, a neurological disorder, an immune disorder, a cancer, a cardiovascular disorder, a blood coagulation disorder, a lysosomal storage disorder, or type 2 diabetes, wherein the DNA molecule lacks:
    (a) an origin of replication and/or a drug resistance gene; and
    (b) a recombination site.

97. An isolated linear DNA molecule comprising a plurality of identical amplicons, wherein each of the plurality of identical amplicons comprises one or more therapeutic nucleic acids, wherein the DNA molecule:
    (a) lacks an origin of replication and/or a drug resistance gene;
    (b) lacks a recombination site; and
    (c) comprises a terminal repeat sequence.

98. The isolated linear DNA molecule of any one of paragraphs 93-97, comprising a restriction enzyme site.

99. The isolated linear DNA molecule of paragraph 98, wherein the restriction enzyme site is positioned between the heterologous gene and a terminal repeat sequence.

100. A method of producing the isolated DNA vector of any one of paragraphs 1-90, the method comprising:
    (i) providing a sample comprising a circular DNA vector comprising an AAV genome, wherein the AAV genome comprises the heterologous gene;

(ii) amplifying the AAV genome using polymerase-mediated rolling-circle amplification to generate a linear concatamer;
(iii) digesting the concatamer using a restriction enzyme to generate multiple AAV genomes; and
(iv) allowing each of the multiple AAV genomes to self-ligate to produce an isolated DNA vector comprising the heterologous gene.

101. The method of paragraph 100, wherein the AAV genome comprises a terminal repeat sequence.

102. The method of paragraph 100 or 101, further comprising column purifying the isolated DNA vector comprising the heterologous gene to purify supercoiled DNA from the isolated DNA vector.

103. A method of producing the isolated DNA vector of any one of paragraphs 1-90, the method comprising:
(i) providing a sample comprising a circular DNA vector comprising an AAV genome, wherein the AAV genome comprises the heterologous gene and a terminal repeat sequence;
(ii) amplifying the AAV genome using a first polymerase-mediated rolling-circle amplification to generate a first linear concatamer;
(iii) digesting the first linear concatamer using a restriction enzyme to generate a first AAV genome;
(iv) cloning the first AAV genome into a plasmid vector;
(v) identifying a plasmid clone comprising a terminal repeat sequence;
(vi) digesting the plasmid clone comprising the terminal repeat sequence to generate a second AAV genome;
(vii) allowing the second AAV genome to self-ligate to produce a circular DNA template;
(viii) amplifying the circular DNA template using second polymerase-mediated rolling-circle amplification to generate a second linear concatamer;
(ix) digesting the second linear concatamer using a restriction enzyme to generate a third AAV genome; and
(x) allowing the third AAV genome to self-ligate to produce an isolated DNA vector comprising the heterologous gene and the terminal repeat sequence.

104. The method of any one of paragraphs 100-103, wherein the polymerase-mediated rolling-circle amplification is isothermal rolling-circle amplification.

105. The method of any one of paragraphs 100-104, wherein the polymerase is Phi29 DNA polymerase.

106. A cell-free method of producing the isolated DNA vector of any one of paragraphs 1-71, the method comprising:
(i) providing a sample comprising a circular DNA vector comprising an AAV genome, wherein the AAV genome comprises the heterologous gene;
(ii) amplifying the AAV genome using polymerase-mediated rolling-circle amplification to generate a linear concatamer;
(iii) digesting the concatamer using a restriction enzyme to generate an AAV genome; and
(iv) allowing the AAV genome to self-ligate to produce the isolated DNA vector comprising the heterologous gene.

107. The method of paragraph 106, further comprising column purifying the isolated DNA vector comprising the heterologous gene to purify supercoiled DNA from the isolated DNA vector.

108. The method of paragraph 106 or 107, wherein the polymerase-mediated rolling-circle amplification is isothermal rolling-circle amplification.

109. The method of any one of paragraphs 106-108, wherein the polymerase is Phi29 DNA polymerase.

110. A method of producing the isolated DNA vector of any one of paragraphs 1-90, the method comprising:
(i) providing a sample comprising a circular DNA vector comprising an AAV genome, wherein the AAV genome comprises the heterologous gene and a DD element;
(ii) amplifying the AAV genome using polymerase-mediated rolling-circle amplification to generate a linear concatamer;
(iii) digesting the concatamer using a restriction enzyme to generate multiple AAV genomes; and
(iv) allowing each of the multiple AAV genomes to self-ligate to produce an isolated DNA vector comprising the heterologous gene and the DD element.

111. A method of producing the isolated DNA vector of any one of paragraphs 1-90, the method comprising:
(i) providing a sample comprising a circular DNA vector comprising an AAV genome, wherein the AAV genome comprises the heterologous gene and a DD element;
(ii) amplifying the AAV genome using a first polymerase-mediated rolling-circle amplification to generate a first linear concatamer;
(iii) digesting the first linear concatamer using a restriction enzyme to generate a first AAV genome;
(iv) cloning the first AAV genome into a plasmid vector;
(v) identifying a plasmid clone comprising a DD element;
(vi) digesting the plasmid clone comprising the DD element to generate a second AAV genome;
(vii) allowing the second AAV genome to self-ligate to produce a circular DNA template;
(viii) amplifying the circular DNA template using second polymerase-mediated rolling-circle amplification to generate a second linear concatamer;
(ix) digesting the second linear concatamer using a restriction enzyme to generate a third AAV genome; and
(x) allowing the third AAV genome to self-ligate to produce an isolated DNA vector comprising the heterologous gene and the DD element.

112. The method of paragraph 110 or 111, wherein the polymerase-mediated rolling-circle amplification is isothermal rolling-circle amplification.

113. The method of any one of paragraphs 110-112, wherein the polymerase is Phi29 DNA polymerase.

114. A cell-free method of producing the isolated DNA vector of any one of paragraphs 1-90, the method comprising:
(i) providing a sample comprising a circular DNA vector comprising an AAV genome, wherein the AAV genome comprises the heterologous gene and a DD element;
(ii) amplifying the AAV genome using polymerase-mediated rolling-circle amplification to generate a linear concatamer;
(iii) digesting the concatamer using a restriction enzyme to generate an AAV genome; and
(iv) allowing the AAV genome to self-ligate to produce a therapeutic DNA vector comprising the heterologous gene and the DD element.

115. The method of paragraph 114, wherein the polymerase-mediated rolling-circle amplification is isothermal rolling-circle amplification.

116. The method of paragraph 114 or 115, wherein the polymerase is Phi29 DNA polymerase.

117. A method of inducing episomal expression of a heterologous gene in a subject in need thereof, the method comprising administering to the subject the isolated DNA vector of any one of paragraphs 1-90 or the composition of paragraph 91 or 92.

118. A method of treating a disorder in a subject, the method comprising administering to the subject the isolated DNA vector of any one of paragraphs 1-90 or the composition of paragraph 91 or 92 in a therapeutically effective amount.

119. The method of paragraph 117 or 118, wherein the isolated DNA vector or the composition is administered repeatedly.

120. The method of paragraph 117 or 118, wherein the isolated DNA vector or the composition is administered systemically.

121. The method of any one of paragraphs 117-120, wherein the isolated DNA vector or the composition is administered intravenously.

122. The method of any one of paragraphs 117-120, wherein the isolated DNA vector or the composition is administered locally.

123. The method of paragraph 122, wherein the isolated DNA vector or the composition is administered intravitreally.

124. The method of any one of paragraphs 117-123, wherein the disorder is an ocular disorder.

125. The method of paragraph 124, wherein the ocular disorder is a Mendelian-heritable retinal dystrophy.

126. The method of paragraph 124, wherein the ocular disorder is LCA, Stargardt Disease, pseudoxanthoma elasticum, rod cone dystrophy, exudative vitreoretinopathy, Joubert Syndrome, CSNB-1C, age-related macular degeneration, retinitis pigmentosa, stickler syndrome, microcephaly and chorioretinopathy, retinitis pigmentosa, CSNB 2, Usher syndrome, or Wagner syndrome.

127. The method of any one of paragraphs 117-126, wherein the isolated DNA vector or the composition is administered systemically.

128. The method of paragraph 127, wherein the disorder is a coagulation disorder.

129. The method of paragraph 128, wherein the coagulation disorder is hemophilia, von Willebrand's disease, factor XI deficiency, a fibrinogen disorder, or a vitamin K deficiency.

Other Embodiments

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and can be applied to the essential features hereinbefore set forth, and follows in the scope of the claims.

Other embodiments are within the claims.

The invention claimed is:

1. A pharmaceutical composition for delivery of a gene in a subject, wherein the pharmaceutical composition comprises a synthetic circular DNA vector comprising a promoter operably linked to the gene, wherein the synthetic circular DNA vector lacks an origin of replication, a drug resistance gene, and a site-specific recombination recognition site, wherein the promoter is capable of inducing expression of the gene in the subject.

2. The pharmaceutical composition of claim 1, further comprising a delivery vehicle selected from liposomes, nanoparticles, microparticles, microspheres, lipid particles, vesicles, polyaxamer, and polycationic material, and combinations thereof.

3. The pharmaceutical composition of claim 1, wherein the promoter is substantially devoid of CpG islands.

4. The pharmaceutical composition of claim 1, wherein the synthetic circular DNA vector further comprises a polyadenylation site downstream of the gene.

5. The pharmaceutical composition of claim 1, wherein the synthetic circular DNA vector is supercoiled.

6. The pharmaceutical composition of claim 1, wherein 70% to 99.9% of the synthetic circular DNA vector in the pharmaceutical composition is monomeric.

7. The pharmaceutical composition of claim 1, wherein the pharmaceutical composition is formulated to be administered intravenously, intramuscularly, intradermally, intracerebrally, intrathecally, intratumorally, intratracheally, intrapleurally, or by inhalation.

8. The pharmaceutical composition of claim 1, wherein the gene is at least 5 Kb in length.

9. The pharmaceutical composition of claim 1, wherein the synthetic circular DNA vector is substantially devoid of CpG islands.

10. The pharmaceutical composition of claim 1, wherein the pharmaceutical composition does not cause significant increases of cytokine levels when administered to a subject.

11. The pharmaceutical composition of claim 1, wherein the gene encodes a polypeptide.

12. The pharmaceutical composition of claim 11, wherein the polypeptide is a replacement polypeptide.

13. The pharmaceutical composition of claim 1, wherein the gene encodes a therapeutic nucleic acid.

14. The pharmaceutical composition of claim 1, wherein the pharmaceutical composition comprises a unit dose of the synthetic circular DNA vector of from 10 μg to 10 mg.

15. The pharmaceutical composition of claim 1, wherein the pharmaceutical composition is substantially devoid of an immunogenic component.

16. The pharmaceutical composition of claim 15, wherein the immunogenic component comprises endotoxin, bacterial contaminants, flagellin, lipoteichoic acid, peptidoglycan, or a combination thereof.

17. The pharmaceutical composition of claim 1, wherein the gene is a human gene.

* * * * *

SEQUENCE LISTING

```
Sequence total quantity: 42
SEQ ID NO: 1            moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 1
aggaacccct agtgatggag                                                   20

SEQ ID NO: 2            moltype = DNA  length = 41
FEATURE                 Location/Qualifiers
misc_feature            1..41
                        note = Synthetic Construct
source                  1..41
                        mol_type = other DNA
                        organism = synthetic construct
SEQUENCE: 2
ttggccactc cctctctgcg cgctdgctcg ctcactgagg c                           41

SEQ ID NO: 3            moltype =     length =
SEQUENCE: 3
000

SEQ ID NO: 4            moltype =     length =
SEQUENCE: 4
000

SEQ ID NO: 5            moltype =     length =
SEQUENCE: 5
000

SEQ ID NO: 6            moltype =     length =
SEQUENCE: 6
000
```

```
SEQ ID NO: 7              moltype = DNA   length = 41
FEATURE                   Location/Qualifiers
misc_feature              1..41
                          note = Synthetic Construct
source                    1..41
                          mol_type = other DNA
                          organism = synthetic construct
SEQUENCE: 7
gcctcagtga gcgagcgagc gcgcagagag ggagtggcca a                        41

SEQ ID NO: 8              moltype = DNA   length = 20
FEATURE                   Location/Qualifiers
misc_feature              1..20
                          note = Synthetic Construct
source                    1..20
                          mol_type = other DNA
                          organism = synthetic construct
SEQUENCE: 8
ctccatcact aggggttcct                                                20

SEQ ID NO: 9              moltype = DNA   length = 165
FEATURE                   Location/Qualifiers
misc_feature              1..165
                          note = Synthetic Construct
source                    1..165
                          mol_type = other DNA
                          organism = synthetic construct
SEQUENCE: 9
aggaacccct agtgatggag ttggccactc cctctctgcg cgctcgctcg ctcactgagg     60
ccgcccgggc aaagcccggg cgtcgggcga cctttggtcg cccggcctca gtgagcgagc    120
gagcgcgcag agagggagtg gccaactcca tcactagggg ttcct                    165

SEQ ID NO: 10             moltype = DNA   length = 165
FEATURE                   Location/Qualifiers
misc_feature              1..165
                          note = Synthetic Construct
source                    1..165
                          mol_type = other DNA
                          organism = synthetic construct
SEQUENCE: 10
aggaacccct agtgatggag ttggccactc cctctctgcg cgctcgctcg ctcactgagg     60
ccgggcgacc aaaggtcgcc cgacgcccgg gctttgcccg ggcggcctca gtgagcgagc    120
gagcgcgcag agagggagtg gccaactcca tcactagggg ttcct                    165

SEQ ID NO: 11             moltype = DNA   length = 143
FEATURE                   Location/Qualifiers
misc_feature              1..143
                          note = Synthetic Construct
source                    1..143
                          mol_type = other DNA
                          organism = synthetic construct
SEQUENCE: 11
aggaacccct agtgatggag ttggccactc cctctctgcg cgctcgctcg ctcactgagg     60
ccgcccgggc aaagcccggg cggcctcagt gagcgagcga gcgcgcagag agggagtggc    120
caactccatc actaggggtt cct                                            143

SEQ ID NO: 12             moltype = DNA   length = 143
FEATURE                   Location/Qualifiers
misc_feature              1..143
                          note = Synthetic Construct
source                    1..143
                          mol_type = other DNA
                          organism = synthetic construct
SEQUENCE: 12
aggaacccct agtgatggag ttggccactc cctctctgcg cgctcgctcg ctcactgagg     60
ccgggcgacc tttggtcgcc cggcctcagt gagcgagcga gcgcgcagag agggagtggc    120
caactccatc actaggggtt cct                                            143

SEQ ID NO: 13             moltype = DNA   length = 122
FEATURE                   Location/Qualifiers
misc_feature              1..122
                          note = Synthetic Construct
source                    1..122
                          mol_type = other DNA
                          organism = synthetic construct
```

```
SEQUENCE: 13
aggaacccct agtgatggag ttggccactc cctctctgcg cgctcgctcg ctcactgagg    60
cgcctcagtg agcgagcgag cgcgcagaga gggagtggcc aactccatca ctaggggttc   120
ct                                                                  122

SEQ ID NO: 14          moltype = DNA   length = 40
FEATURE                Location/Qualifiers
misc_feature           1..40
                       note = Synthetic Construct
source                 1..40
                       mol_type = other DNA
                       organism = synthetic construct
SEQUENCE: 14
aggaacccct agtgatggag ctccatcact aggggttcct                          40

SEQ ID NO: 15          moltype = DNA   length = 115
FEATURE                Location/Qualifiers
misc_feature           1..115
                       note = Synthetic Construct
source                 1..115
                       mol_type = other DNA
                       organism = synthetic construct
SEQUENCE: 15
aggaacccct agtgatggag ttggccactc cctctctgcg cgctcgctcg ctcactgagg    60
ccgcccgggc gagcgcgcag agagggagtg gccaactcca tcactagggg ttcct        115

SEQ ID NO: 16          moltype = DNA   length = 129
FEATURE                Location/Qualifiers
misc_feature           1..129
                       note = Synthetic Construct
source                 1..129
                       mol_type = other DNA
                       organism = synthetic construct
SEQUENCE: 16
aggaacccct agtgatggag ttggccactc cctctctgcg cgctcgctcg ctcactgagg    60
ccgcccgggc ctcagtgagc gagcgagcgc gcagagaggg agtggccaac tccatcacta   120
ggggttcct                                                           129

SEQ ID NO: 17          moltype = DNA   length = 73
FEATURE                Location/Qualifiers
misc_feature           1..73
                       note = Synthetic Construct
source                 1..73
                       mol_type = other DNA
                       organism = synthetic construct
SEQUENCE: 17
aggaacccct agtgatggag ttggccactc cctcgcagag agggagtggc caactccatc    60
actagggggtt cct                                                      73

SEQ ID NO: 18          moltype = DNA   length = 107
FEATURE                Location/Qualifiers
misc_feature           1..107
                       note = Synthetic Construct
source                 1..107
                       mol_type = other DNA
                       organism = synthetic construct
SEQUENCE: 18
aggaacccct agtgatggag ttggccactc cctctctgcg cgctcgctcg ctcactgagg    60
ccgagcgcgc agagagggag tggccaactc catcactagg ggttcct                 107

SEQ ID NO: 19          moltype = DNA   length = 18
FEATURE                Location/Qualifiers
misc_feature           1..18
                       note = Synthetic Construct
source                 1..18
                       mol_type = other DNA
                       organism = synthetic construct
SEQUENCE: 19
ttaccccctag tgatggag                                                 18

SEQ ID NO: 20          moltype = DNA   length = 18
FEATURE                Location/Qualifiers
misc_feature           1..18
                       note = Synthetic Construct
source                 1..18
                       mol_type = other DNA
                       organism = synthetic construct
SEQUENCE: 20
ctccatcact aggggtaa                                                  18
```

```
SEQ ID NO: 21            moltype = DNA  length = 21
FEATURE                  Location/Qualifiers
misc_feature             1..21
                         note = Synthetic Construct
source                   1..21
                         mol_type = other DNA
                         organism = synthetic construct
SEQUENCE: 21
gccataccct ctagtgatgga g                                                  21

SEQ ID NO: 22            moltype = DNA  length = 21
FEATURE                  Location/Qualifiers
misc_feature             1..21
                         note = Synthetic Construct
source                   1..21
                         mol_type = other DNA
                         organism = synthetic construct
SEQUENCE: 22
ctccatcact agaggtatgg c                                                   21

SEQ ID NO: 23            moltype = DNA  length = 21
FEATURE                  Location/Qualifiers
misc_feature             1..21
                         note = Synthetic Construct
source                   1..21
                         mol_type = other DNA
                         organism = synthetic construct
SEQUENCE: 23
gggcaaacct agatgatgga g                                                   21

SEQ ID NO: 24            moltype = DNA  length = 21
FEATURE                  Location/Qualifiers
misc_feature             1..21
                         note = Synthetic Construct
source                   1..21
                         mol_type = other DNA
                         organism = synthetic construct
SEQUENCE: 24
ctccatcatc taggtttgcc c                                                   21

SEQ ID NO: 25            moltype = DNA  length = 30
FEATURE                  Location/Qualifiers
misc_feature             1..30
                         note = Synthetic Construct
source                   1..30
                         mol_type = other DNA
                         organism = synthetic construct
SEQUENCE: 25
tacaaaacct ccttgcttga gagtgtggca                                          30

SEQ ID NO: 26            moltype = DNA  length = 30
FEATURE                  Location/Qualifiers
misc_feature             1..30
                         note = Synthetic Construct
source                   1..30
                         mol_type = other DNA
                         organism = synthetic construct
SEQUENCE: 26
tgccacactc tcaagcaagg aggttttgta                                          30

SEQ ID NO: 27            moltype = DNA  length = 20
FEATURE                  Location/Qualifiers
misc_feature             1..20
                         note = Synthetic Construct
source                   1..20
                         mol_type = other DNA
                         organism = synthetic construct
SEQUENCE: 27
aggaacccct agtgatggag                                                     20

SEQ ID NO: 28            moltype = DNA  length = 20
FEATURE                  Location/Qualifiers
misc_feature             1..20
                         note = Synthetic Construct
source                   1..20
                         mol_type = other DNA
                         organism = synthetic construct
```

```
SEQUENCE: 28
ctccatcact aggggttcct                                                    20

SEQ ID NO: 29           moltype = DNA  length = 22
FEATURE                 Location/Qualifiers
misc_feature            1..22
                        note = Synthetic Construct
source                  1..22
                        mol_type = other DNA
                        organism = synthetic construct
SEQUENCE: 29
cgcggtaccc ctagtgatgg ac                                                 22

SEQ ID NO: 30           moltype = DNA  length = 22
FEATURE                 Location/Qualifiers
misc_feature            1..22
                        note = Synthetic Construct
source                  1..22
                        mol_type = other DNA
                        organism = synthetic construct
SEQUENCE: 30
ctccatcact aggggtaccg cg                                                 22

SEQ ID NO: 31           moltype = DNA  length = 143
FEATURE                 Location/Qualifiers
misc_feature            1..143
                        note = Synthetic Construct
source                  1..143
                        mol_type = other DNA
                        organism = synthetic construct
SEQUENCE: 31
ttgcccactc cctctctgcg cgctcgctcg ctcggtgggg cctgcggacc aaaggtccgc        60
agacggcaga gctctgctct gccggcccca ccgagcgagc gagcgcgcag agagggagtg       120
ggcaactcca tcactagggg taa                                               143

SEQ ID NO: 32           moltype = DNA  length = 145
FEATURE                 Location/Qualifiers
misc_feature            1..145
                        note = Synthetic Construct
source                  1..145
                        mol_type = other DNA
                        organism = synthetic construct
SEQUENCE: 32
ttggccactc cctctctgcg cgctcgctcg ctcactgagg ccgggcgacc aaaggtcgcc        60
cgacgcccgg gctttgcccg ggcggcctca gtgagcgagc gagcgcgcag agagggagtg       120
gccaactcca tcactagggg ttcct                                             145

SEQ ID NO: 33           moltype = DNA  length = 146
FEATURE                 Location/Qualifiers
misc_feature            1..146
                        note = Synthetic Construct
source                  1..146
                        mol_type = other DNA
                        organism = synthetic construct
SEQUENCE: 33
ttggccactc cctctatgcg cactcgctcg ctcggtgggg cctggcgacc aaaggtcgcc        60
agacggacgt gctttgcacg tccggcccca ccgagcgagc gagtgcgcat agagggagtg       120
gccaactcca tcactagagg tatggc                                            146

SEQ ID NO: 34           moltype = DNA  length = 146
FEATURE                 Location/Qualifiers
misc_feature            1..146
                        note = Synthetic Construct
source                  1..146
                        mol_type = other DNA
                        organism = synthetic construct
SEQUENCE: 34
ttggccactc cctctatgcg cgctcgctca ctcactcggc cctggagacc aaaggtctcc        60
agactgccgg cctctggccg gcagggccga gtgagtgagc gagcgcgcat agagggagtg       120
gccaactcca tcatctaggt ttgccc                                            146

SEQ ID NO: 35           moltype = DNA  length = 167
FEATURE                 Location/Qualifiers
misc_feature            1..167
                        note = Synthetic Construct
source                  1..167
                        mol_type = other DNA
                        organism = synthetic construct
```

```
SEQUENCE: 35
ctctccccc tgtcgcgttc gctcgctcgc tggctcgttt gggggggtgg cagctcaaag    60
agctgccaga cgacggccct ctggccgtcg cccccccaaa cgagccagcg agcgagcgaa   120
cgcgacaggg gggagagtgc cacactctca agcaaggagg ttttgta               167

SEQ ID NO: 36           moltype = DNA   length = 145
FEATURE                 Location/Qualifiers
misc_feature            1..145
                        note = Synthetic Construct
source                  1..145
                        mol_type = other DNA
                        organism = synthetic construct
SEQUENCE: 36
ttggccactc cctctctgcg cgctcgctcg ctcactgagg ccgggcgacc aaaggtcgcc    60
cgacgcccgg gctttgcccg ggcggcctca gtgagcgagc gagcgcgcag agagggagtg   120
gccaactcca tcactagggg ttcct                                        145

SEQ ID NO: 37           moltype = DNA   length = 147
FEATURE                 Location/Qualifiers
misc_feature            1..147
                        note = Synthetic Construct
source                  1..147
                        mol_type = other DNA
                        organism = synthetic construct
SEQUENCE: 37
ttggccactc cctctatgcg cgctcgctcg ctcggtgggg cctgcggacc aaaggtccgc    60
agacggcaga gctctgctct gccggcccca ccgagcgagc gagcgcgcat agagggagtg   120
gccaactcca tcactagggg taccgcg                                      147

SEQ ID NO: 38           moltype = DNA   length = 22
FEATURE                 Location/Qualifiers
misc_feature            1..22
                        note = Synthetic Construct
source                  1..22
                        mol_type = other DNA
                        organism = synthetic construct
SEQUENCE: 38
cgcgctaccc ctagtgatgg ag                                            22

SEQ ID NO: 39           moltype = DNA   length = 22
FEATURE                 Location/Qualifiers
misc_feature            1..22
                        note = Synthetic Construct
source                  1..22
                        mol_type = other DNA
                        organism = synthetic construct
SEQUENCE: 39
ctccatcact aggggtagcg cg                                            22

SEQ ID NO: 40           moltype = DNA   length = 23
FEATURE                 Location/Qualifiers
misc_feature            1..23
                        note = Synthetic Construct
source                  1..23
                        mol_type = other DNA
                        organism = synthetic construct
SEQUENCE: 40
cgcgattacc cctagtgatg gag                                           23

SEQ ID NO: 41           moltype = DNA   length = 23
FEATURE                 Location/Qualifiers
misc_feature            1..23
                        note = Synthetic Construct
source                  1..23
                        mol_type = other DNA
                        organism = synthetic construct
SEQUENCE: 41
ctccatcact aggggtaatc gcg                                           23

SEQ ID NO: 42           moltype = DNA   length = 6100
FEATURE                 Location/Qualifiers
misc_feature            1..6100
                        note = Synthetic Construct
source                  1..6100
                        mol_type = other DNA
                        organism = synthetic construct
SEQUENCE: 42
ctaaattgta agcgttaata ttttgttaaa attcgcgtta aatttttgtt aaatcagctc    60
atttttaac caataggccg aaatcggcaa atcccttat aaatcaaaag aatagaccga   120
```

```
gatagggttg agtgttgttc cagtttggaa caagagtcca ctattaaaga acgtggactc    180
caacgtcaaa gggcgaaaaa ccgtctatca gggcgatggc ccactacgtg aaccatcacc    240
ctaatcaagt tttttggggt cgaggtgccg taaagcacta aatcggaacc ctaaagggag    300
cccccgattt agagcttgac ggggaaagcc ggcgaacgtg gcgagaaagg aagggaagaa    360
agcgaaagga gcgggcgcta gggcgcttggc aagtgtaggc gtcacgctgc gcgtaaccac    420
cacacccgcc gcgcttaatg cgccgctaca gggcgcgtcc cattcgccat tcaggctgcc    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta tagggcgaat tggagctcca    660
ccgcggtggc ggccgctcta gaactagtgg atccccgggg ctgcaggaat tcggtaccgg    720
atccagatct caattgacgc gtcccgggcc taccttaaga gagcgcgtat ttaaatcgct    780
accttaggac cgttatagtt atcgactgaa ttgccgcagg aaccctagt gatggagttg     840
gccactccct ctctgcgcgc tcgctcgctc actgaggccg cccgggcaaa gcccgggcgt    900
cgggcgacct ttggtcgccc ggcctcagtg agcgagcgag cgcgcagaga gggagtggcc    960
aactccatca ctaggggttc ctgcggcccg cgccattacc ctgttatccc taatttaaat   1020
ctcgatgcta ccttaagaga ggatatcccc ggtcagaagc catagagccc accgcatccc   1080
cagcatgcct gctattgtct tcccaatcct cccccttgct gtcctgcccc accccacccc   1140
ccagaataga atgacaccta ctcagacaat gcgatgcaat ttcctcattt tattaggaaa   1200
ggacagtggg agtggcacct tccagggtca aggaaggcac gggggagggg caaacaacag   1260
atggctggca actagaaggc acagtcgagg ctgatcagcg ggtttaaaact tacttgtaca   1320
gctcgtccat gccgagagtg atcccggcgg cggtcacgaa ctccagcagg accatgtgat   1380
cgcgcttctc gttgggtct ttgctcaggg cggactgggt gctcaggtag tggttgtcgg    1440
gcagcagcac ggggccgtcg ccgatggggg tgttctgctg gtagtggtcg gcgagctgca   1500
cgctgccgtc ctcgatgttg tggcggatct tgaagttcac cttgatgccg ttcttctgct   1560
tgtcggccat gatatagacg ttgtggctgt tgtagttgta ctccagcttg tgccccagga   1620
tgttgccgtc ctccttgaag tcgatgcct tcagctgacg gccggttcacc agggtgtcgg    1680
cctcgaactt cacctcggcg cgggtcttgt agttgccgtc gtccttgaag aagatggtgt   1740
gctcctggac gtagccttcg ggcatggcgg acttgaagaa gtcgtgctgc ttcatgtggt   1800
cggggtagcg gctgaagcac tgcacgccgt aggtcagggt ggtcacgagg gtgggccagg   1860
gcacgggcag cttgccggtg gtgcagatga acttcagggt cagcttgccg taggtggcat   1920
cgccctcgcc ctcgcggac acgctgaact tgtggccgtt tacgtcgccg tccagctcga   1980
ccaggatggg caccaccccg gtgaacagct cctcgccctt gctcaccatg gtggcgagct   2040
agactatgcg gccgctagtg tacaccaacc tgtcaggaga ggaaagagaa gaaggttagt   2100
acaattgtct agagccgccg gtcacacgcc agaagccgaa ccccgccctg cccgtcccc    2160
cccgaaggca gccgtcccc cgcggacagc cccgaggctg gagagggaga aggggacggc    2220
ggcgcggcga cgcacgaagg ccctccccgc ccatttcctt cctgccggcg ccgcaccgct   2280
tcgccccgcg cccgctagag ggggtgcggc ggcgcctccc agatttcggc tccgcacaga   2340
tttgggacaa aggaagtccc tgcgccctct cgcacgatta ccataaaagg caatggctgc   2400
ggctcgccgc gcctcgacag ccgccgcgc tccggggcc gccgccccc tccccgagc      2460
cctcccggc ccgaggcggc cccgccccgc ccggcacccc cacctgccgc caccccccg    2520
ccggcacggc gagcccgcg ccacgccccg tacgagcccc gcacccgaa gccgggccgt    2580
gctcagcaac tcggggaggg gggtgcaggg ggggttgcag cccgaccgac gcgcccacac   2640
ccctcgtca ccccccacg cacacacccc gcacgcagcc tttgttcccc tcgcagcccc    2700
ccccgcaccg cggggcaccg ccccccggcc gcctccccctc gcgcacactg cggagcgcac   2760
aaagccccgc gccgcgcccg cagcgctcac agccgccgggg cagcgcggag ccgcacgcgg   2820
cgctccccac gcacacacac acgcacgcac ccccgagcc gctcccccg cacaaagggc     2880
cctccggag ccccctcaagg cttttcacgca gccacagaaa agaaacaagc cgtcattaaa   2940
ccaagcgcta attacagccc ggaggagaag ggccgtcccg cccgctcacc tgtgggagta   3000
acgcggtcag tcagagccgg ggcgggcggc gcgaggcggc ggcggagcgg ggcacggggc   3060
gaaggcagcg tcgcagcgac tccccgcccg ccgcgcgctt cgcttttat agggccgcc    3120
ccgccgccgc ctcgccataa aaggaaactt tcggagcgcg ccgctctgat tggctgcgc    3180
cgcacctctc cgcctcgccc cgccccgccc ctcgccccgc cccgcccgc ctggcgcgcg    3240
ccccccccc cccccgccc ccatcgctgc acaaaataat taaaaaataa ataatacaa      3300
aattgggggt gggagggg gggagatggg gagagtgaag cagaacgtgg ggctcacctc     3360
gaccatgtta atagcgatga ctaatacgta gatgtactgc caagtaggaa agtcccataa   3420
ggtcatgtac tgggcataat gccaggcggg ccatttaccg tcattgacgt caataggggg   3480
cgtacttggc atatgataca cttgatgtac tgccaagtgg gcagtttacc gtaaatactc   3540
cacccattga cgtcaatgga aagtccctat tggcgttact atgggaacat acgtcattat   3600
tgacgtcaat gggcggggt cgttgggcgg tcagccagge gggccatta ccgtaagtta     3660
tgtaacgcgg aactccatat atgggctatg aactaatgac cccgtaattg attactatta   3720
ataactagtc aataatcaat gtcaacgcgt atatctggcc cgtacatcgc gaagcagcgc   3780
aaaacgccta accctaagca gattcttcat gcaacccggg tctagaagct tctcgaggcg   3840
gccgcgaatt cgatatcaag cttatcgata ccgtcgacct cgaggggggg cccggtaccc   3900
agcttttgtt ccctttagtg agggtaatt gcgcgcttgg cgtaatcatg gtcatagctg    3960
tttcctgtgt gaaattgtta tccgctcaca attccacaca acatacgagc cggaagcata   4020
aagtgtaaag cctggggtgc ctaatgagtg agctaactca cattaattgc gttgcgctca   4080
ctgcccgctt tccagtcggg aaacctgtcg tgccagctgc attaatgaat cggccaacgc   4140
gcggggagag gcggtttgcg tattgggcgc tcttccgctt cctcgctcac tgactcgctg   4200
cgctcggtcg ttcggctgcg gcgagcggta tcagctcact caaaggcggt aatacggtta   4260
tccacagaat caggggataa cgcaggaaag aacatgtgag caaaaggcca gcaaaaggcc   4320
aggaaccgta aaaaggccgc gttgctggcg tttttccata ggctccgccc cctgacgag    4380
catcacaaaa atcgacgctc aagtcagagg tggcgaaacc cgacaggact ataaagatac   4440
caggcgtttc ccctggaag ctccctcgtg cgctctcctg ttccgaccct gccgcttacc    4500
ggatacctgt ccgcctttct cccttcggga agcgtggcgc tttctcatag ctcacgctgt   4560
aggtatctca gttcggtgta ggtcgttcgc tccaagctgg gctgtgtgca cgaacccccc   4620
gttcagcccg accgctgcgc cttatccggt aactatcgtc ttgagtccaa cccggtaaga   4680
cacgacttat cgccactggc agcagccact ggtaacagga ttagcagagc gaggtatgta   4740
ggcggtgcta cagagttctt gaagtggtgg cctaactacg gctacactag aaggacagta   4800
tttggtatct gcgctctgct gaagccagtt accttcggaa aaagagttgg tagctcttga   4860
```

-continued

```
tccggcaaac aaaccaccgc tggtagcggt ggttttttg tttgcaagca gcagattacg  4920
cgcagaaaaa aaggatctca agaagatcct ttgatctttt ctacggggtc tgacgctcag  4980
tggaacgaaa actcacgtta agggattttg gtcatgagat tatcaaaaag gatcttcacc  5040
tagatccttt taaattaaaa atgaagtttt aaatcaatct aaagtatata tgagtaaact  5100
tggtctgaca gttaccaatg cttaatcagt gaggcaccta tctcagcgat ctgtctattt  5160
cgttcatcca tagttgcctg actccccgtc gtgtagataa ctacgatacg ggagggctta  5220
ccatctggcc ccagtgctgc aatgataccg cgagacccac gctcaccggc tccagattta  5280
tcagcaataa accagccagc cggaagggcc gagcgcagaa gtggtcctgc aactttatcc  5340
gcctccatcc agtctattaa ttgttgccgg gaagctagag taagtagttc gccagttaat  5400
agtttgcgca acgttgttgc cattgctaca ggcatcgtgg tgtcacgctc gtcgtttggt  5460
atggcttcat tcagctccgg ttcccaacga tcaaggcgag ttacatgatc ccccatgttg  5520
tgcaaaaaag cggttagctc cttcggtcct ccgatcgttg tcagaagtaa gttggccgca  5580
gtgttatcac tcatggttat ggcagcactg cataattctc ttactgtcat gccatccgta  5640
agatgctttt ctgtgactgg tgagtactca accaagtcat tctgagaata gtgtatgcgg  5700
cgaccgagtt gctcttgccc ggcgtcaata cgggataata ccgcgccaca tagcagaact  5760
ttaaaagtgc tcatcattgg aaaacgttct cggggcgaa aactctcaag gatcttaccg  5820
ctgttgagat ccagttcgat gtaacccact cgtgcaccca actgatcttc agcatctttt  5880
actttcacca gcgtttctgg gtgagcaaaa acaggaaggc aaaatgccgc aaaaaaggga  5940
ataagggcga cacggaaatg ttgaatactc atactcttcc ttttcaata ttattgaagc  6000
atttatcagg gttattgtct catgagcgga tacatatttg aatgtattta gaaaaataaa  6060
caaatagggg ttccgcgcac atttccccga aaagtgccac                        6100
```